(12) United States Patent
Ebright et al.

(10) Patent No.: US 7,282,373 B2
(45) Date of Patent: *Oct. 16, 2007

(54) ULTRA-HIGH SPECIFICITY FLUORESCENT LABELING

(75) Inventors: Richard H. Ebright, North Brunswick, NJ (US); Yon W. Ebright, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/257,292

(22) Filed: Oct. 24, 2005

(65) Prior Publication Data

US 2006/0141531 A1 Jun. 29, 2006

Related U.S. Application Data

(60) Provisional application No. 60/638,528, filed on Dec. 23, 2004.

(51) Int. Cl.
| | |
|---|---|
| G01N 33/533 | (2006.01) |
| G01N 21/76 | (2006.01) |
| G01N 21/00 | (2006.01) |
| G01N 33/53 | (2006.01) |
| C07K 1/13 | (2006.01) |
| C07D 209/04 | (2006.01) |

(52) U.S. Cl. .................. 436/546; 436/544; 436/172; 436/164; 436/800; 436/805; 435/7.1; 435/968; 435/69.7; 530/402; 530/408; 548/102; 548/402

(58) Field of Classification Search ............... 436/544, 436/546, 172, 164, 800, 805; 435/7.1, 968, 435/69.7; 530/402, 408; 548/102, 402

See application file for complete search history.

(56) References Cited

U.S. PATENT DOCUMENTS 4,981,977 A 1/1991 Southwick et al.

(Continued)

FOREIGN PATENT DOCUMENTS

EP 0 747 448 A2 11/1996

(Continued)

OTHER PUBLICATIONS

Zhang et al. Creating new fluorescent probes for cell biology. Nature reviews/Molecular cell biology 2002, vol. 3, pp. 906-918.*

(Continued)

*Primary Examiner*—Long V. Le
*Assistant Examiner*—Shafiqul Haq
(74) *Attorney, Agent, or Firm*—Hoffman & Baron, LLP

(57) ABSTRACT

A self-assembled relay probe for detecting a target material is provided including: a first peptide tag bound to the target material; and a first fluorescent conjugate including a first fluorochrome and a first tag binding group; wherein the first fluorescent conjugate selectively associates with the first tag. The probe further includes a second peptide tag bound to the target material; and a second fluorescent conjugate including a second fluorochrome having a longer wavelength and distinct excitation and emission maxima from the first fluorochrome and a second tag binding group. Upon exposure to the target material, the first and second fluorescent conjugates independently associate with the first and second peptide tags, respectively, so as to be a distance apart represented by about 0.1 times $R_0$ to about 2 times $R_0$, such that upon excitation of the first fluorescent conjugate, fluorescence resonance energy transfer results in excitation of the second fluorescent conjugate, yielding detectable emission from the second fluorescent conjugate.

30 Claims, 13 Drawing Sheets

U.S. PATENT DOCUMENTS

| | | | |
|---|---|---|---|
| 5,627,027 | A | 5/1997 | Waggoner |
| 5,932,474 | A | 8/1999 | Tsien et al. |
| 6,008,378 | A | 12/1999 | Tsien et al. |
| 6,054,271 | A | 4/2000 | Tsien et al. |
| 6,086,737 | A | 7/2000 | Patonay et al. |
| 6,130,094 | A | 10/2000 | Waggoner et al. |
| 6,133,445 | A | 10/2000 | Waggoner et al. |
| 6,197,928 | B1 | 3/2001 | Tsien et al. |
| 6,225,050 | B1 | 5/2001 | Waggoner |
| 6,451,569 | B1 | 9/2002 | Tsien et al. |
| 2005/0130167 | A1* | 6/2005 | Bao et al. ............. 435/6 |

FOREIGN PATENT DOCUMENTS

| | | |
|---|---|---|
| EP | 0 747 700 A2 | 11/1996 |
| EP | 0 747 700 B1 | 5/2001 |
| WO | WO99/31181 | 6/1999 |
| WO | WO 03/091689 A2 | 11/2003 |
| WO | WO 03/091689 A3 | 11/2003 |

OTHER PUBLICATIONS

Gaietta et al. Multicolor and electron microscopic imaging of connexin trafficking.Science 2002, vol. 296, pp. 503-507.*

Miyawaki et al. Lighting up cells: labeling proteins with fluorophores. Nature cell biol. 2003, vol. 5, Suppl S1-S7.*

Andresen et al. Short tetracysteine tags to b-tubulin demonstrate the significance of small labels for live cell imaging. Molecular Bioloby of the Cell 2004, vol. 15, pp. 5616-5622.*

Klostermeier et al. A three-fluorophore FRET assay for high-throughput screening of small-molecule inhibitors of ribosome assembly. Nucleic Acids Res. 2004, vol. 32, No. 9, pp. 2707-2715.*

Birch, Martyn et al., 'Dark' Cyanine Dyes §: Their Synthesis And Use As Quenching Partners In Fluorescence Based Assays, Amersham Pharmacia Biotech, The Fourth International Symposium On Functional Dyes, May 31-Jun. 4, 1999, Osaka, Japan, 1 page.

Clegg, Robert M., "Fluorescence Resonance Energy Transfer and Nucleic Acids", Methods in Enzymology, vol. 211, 1992, pp. 353-388.

Kapanidis et al., "Mean DNA Bend Angle and Distribution of DNA Bend Angles in the CAP-DNA Complex in Solution", Journal of Molecular Biology, (2001) 312, pp. 453-468.

Park, H. et al., "Nanometre localization of single ReAsH molecules", Journal of Microscopy, vol. 216, Pt Dec. 3, 2004, pp. 199-205.

Adams, et al., "New Biarsenical Ligands and Tetracysteine Motifs for Protein Labeling in Vitro and in Vivo: Synthesis and Biological Applications", Journal of American Chemical Society, 2002, vol. 124, No. 21, pp. 6063-6076.

Stroffekova et al., "The protein-labeling reagent FLASH-EDT$_2$ binds not only to CCXXCC motifs but also non-specifically to endogenous cysteine-rich proteins", Pflügers Arch—Eur J. Physiol (2001) 442: pp. 859-866.

Mujumdar et al., "Cyanine Dye Labeling Reagents: Sulfoindocyanine Succinimidyl Esters", Bioconjuage Chemistry, Mar./Apr. 1993, vol. 4, No. 2, pp. 106-111.

Nakanishi et al., "Imaging of conformational Changes of Proteins with a New Environment-Sensitive Fluorescent Probe Designed for Site-Specific Labeling of Recombinant Proteins in Live Cells", Analytical Chemistry, vol. 73, No. 13, Jul. 1, 2001, pp. 2920-2928.

Kapanidis et al., Site-Specific Incorporation of Fluorescent Probes into Protein: Hexahistidine-Tag-Mediated Fluroescent Labeling with ($Ni^{2+}$: Nitrilotriacetic Acid)$_n$-Fluorochrome Conjugates, Journal of American Chemical Society 2001, 123, pp. 12123-12125.

Griffin et al., "Specific Covalent Labeling of Recombinant Protein Molecules Inside Live Cells", Science, Jul. 10, 1998, vol. 281, No. 5374, pp. 269-272.

Wu et al., "Resonance Energy Transfer: Methods and Applications", Analytical Biochemistry—Methods in the Biological Sciences, vol. 218, No. 1, Apr. 1994, pp. 1-13.

Chen et al., "Fluorescence Polarization: Measurement with Ultraviolet-Polarizing Filters in a Spectrophotofluorometer", Science, Feb. 12, 1965, vol. 147, pp. 729-732.

* cited by examiner

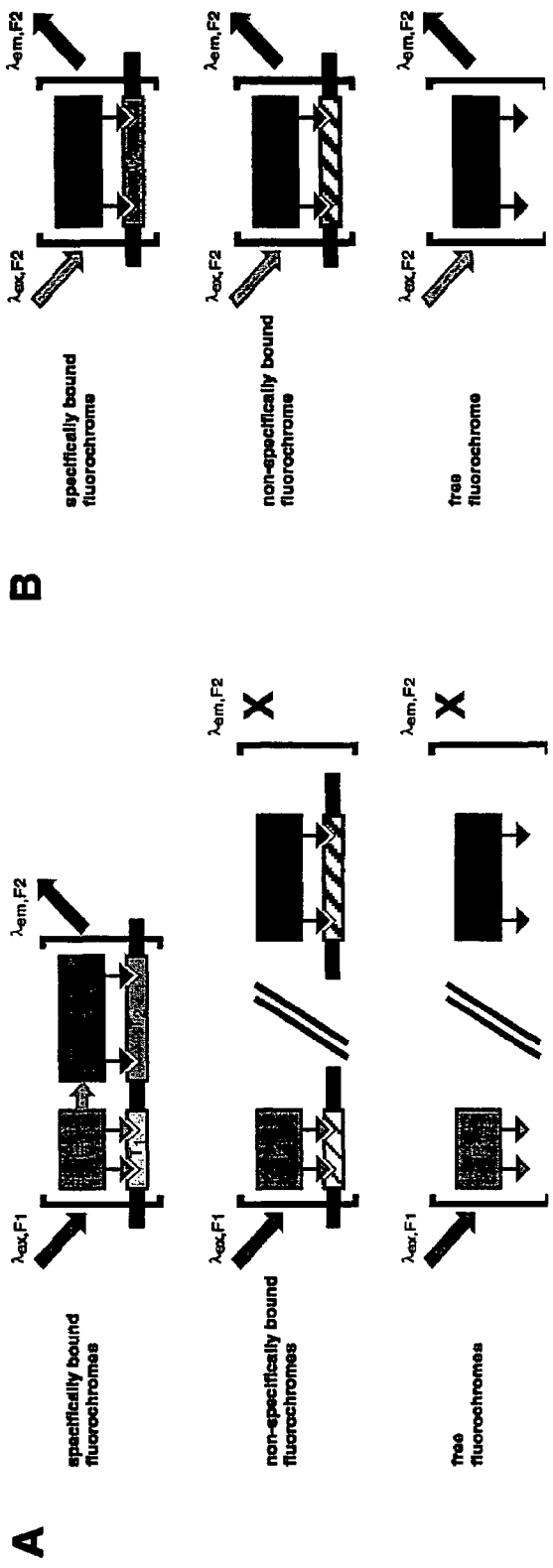

Figure 1 Fluorescence labelling technology: self-assembled relay probes (SARP's). A, SARP. A SARP is a composite probe formed by self-assembly of two biarsenical fluorochromes, $F_1$ and $F_2$, with a target material containing two tetracysteine tags, $T_1$ and $T_2$, and detected by providing excitation at the excitation maximum of $F_1$ ($\lambda_{ex,F1}$) and monitoring emission at the emission maximum of $F_2$ ($\lambda_{em,F2}$), said emission arising from $F_1$-$F_2$ FRET. A SARP exhibits minimal interference from background due to non-specifically incorporated fluorochrome and free fluorochrome—due to insufficient proximity for $F_1$-$F_2$ FRET (middle and bottom panels). B, Conventional fluorochrome.

A SARP detection
DTT: 5 mM  25 mM  50 mM
  
Cy5 + FlAsH   Cy5 + FlAsH   Cy5 + FlAsH
α-SARP-P3/G1-PP9
B SARP detection
DTT: 5 mM  25 mM  50 mM
  
Cy5 + FlAsH   Cy5 + FlAsH   Cy5 + FlAsH
α-SARP-P4/G1-PP9
FIGURE 13

US 7,282,373 B2

ULTRA-HIGH SPECIFICITY FLUORESCENT LABELING

CROSS-REFERENCE TO RELATED APPLICATIONS

The present application claims the benefit of U.S. Provisional Application No. 60/638,528, filed Dec. 23, 2004, which is incorporated herein by reference.

This invention was made with Government support under Grant No. NIH R01-GM41376, awarded by the National Institutes of Health. Therefore, the Government has certain rights in this invention.

FIELD OF THE INVENTION

This invention relates generally to compositions and methods for labeling molecules. More particularly, the present invention relates to methods of using self-assembled relay probes (SARPs), capable of binding with specificity to peptide tags on target materials and emitting a FRET based detectable signal, that are especially useful for detection of polypeptide activity, in cells, in situ, and in direct reading applications.

BACKGROUND OF THE INVENTION

Characterization of proteins often requires the ability to incorporate detectable groups—e.g., fluorochromes, chromophores, spin labels, radioisotopes, paramagnetic atoms, heavy atoms, haptens, crosslinking agents, and cleavage agents—at specific, defined sites. For proteins that do not contain pre-existing cysteine residues, site-specific labeling can be accomplished by use of site-directed mutagenesis to introduce a cysteine residue at the site of interest, followed by cysteine-specific chemical modification to incorporate the labeled probe. However, for proteins that contain pre-existing cysteine residues, site-specific labeling is difficult. Multiple strategies have been reported: (i) intein-mediated labeling ("expressed protein ligation"), (Muir, et al., *Proc. Nat'l. Acad. Sci. USA*, 95:6705-6710 (1998)); (ii) transglutaminase-mediated labeling (Sato et al., *Biochem.* 35:13072-13080 (1996)); (iii) oxidation-mediated labeling (Geoghegan, et al., *Bioconj. Chem.*, 3:138-146 (1992)); (iv) transition-metal-chelate-mediated labeling (Hapanidis et al., *J. Amer. Chem. Soc.*, 123:12123 (2001)) and (v) trivalent-arsenic-mediated labeling (Griffin et al., *Science* 281:269-272, 1998) (U.S. Pat. No. 6,008,378). Strategies (i)-(iii) do not permit in situ labeling (i.e., direct labeling of proteins in cuvettes, gels, blots, or biological samples—without the need for a subsequent purification step) or in vivo labeling (i.e., direct labeling of proteins in cells). Strategy (iv) does not permit labeling and analysis at subnanomolar concentrations. Strategy (iv) requires a structural scaffold presenting two trivalent-arsenic atoms in a precisely defined spatial relationship and therefore relates only to a limited number of detectable groups (such as those having an isoxanthenone/resorufin structural nucleus).

The ability to observe proteins in living systems in cells or in situ can provide important information on expression and activity of the proteins. This information is useful in such wide applications as molecular biology research to histological diagnostics and identification of useful drug candidates. It is well known to use dyes of various types to impart a detectable property to a target material. For example, the technique of bonding a detectable compound, such as a fluorescent dye, to a substituent which is reactive with the target material is used to render the target compound detectable by methods such as fluorescence microscopy, fluorescence immunology and flow cytometry.

Various fluorescent dyes are known, including those based on fluorescein (green fluorescence), rhodamine (orange fluorescence), and coumarin and pyrene chromophores (blue fluorescence). However, use of these dyes may at times be problematic. For example, dyes based on fluorescein have a tendency to photobleach when illuminated with strong excitation sources. The rapid loss of image over time can interfere with detection and quantification of targets labeled using these dyes. Furthermore, fluorescein derivatives have a pH sensitive absorption spectrum with a marked decrease in signal below a pH of 8. Rhodamine derivatives are hydrophobic and are difficult to use in aqueous media. They often show strong fluorescence quenching when bound to proteins. Molecular Probes—*Handbook of Fluorescent Probes and Research Chemicals*, Haugland, R. Ed., (1996). Cyanine dyes possess superior photostability as compared to fluoroscein, better water solubility than the rhodamine dyes, and are stable in the range of pH 3 to 10. For this reason, cyanine dyes have been found particularly useful in labeling biological targets.

When the target material is a biological compound, in cells or in situ, a number of challenges are introduced which limits the utility of many of the known fluorescent dyes. In these applications, in order for a particular dye to be effective, it must first cross the cell membrane. As a result, large dyes, such as phycobiliproteins (molecular weights of from 33,000 to 240,000) are not useful because they are unable to enter the cell to bind with the target material. In addition, when the target is a metabolite, a drug, a hormone, or the like, the dye may be so large that it either interferes with the activity of the target or possesses steric limitations which prohibit it from binding to the target at all.

A further challenge when detecting biological compounds in situ is the need for specificity of association with the target material. Since excess probe cannot be "rinsed off" in these applications, unbound or non-specifically bound probe will introduce noise into the system. Some dyes are known to have a certain degree of specificity for certain endogenous reactive groups or tags in the target material. For example, U.S. Pat. No. 6,225,050 B1 to Waggoner discloses use of certain luminescent cyanine dyes containing a group which is covalently reactive with amine or hydroxyl groups and is used to label biological compounds possessing these groups such as proteins, nucleic acids, cells, sugars, and the like. The fact that amine and hydroxyl groups are numerous and widely dispersed on a protein target is used to facilitate detection of the fluorescent probe or luminescent cyanine dye because it becomes attached at multiple sites on the protein therefore generating a strong signal.

The method of Waggoner may be used to quantify a biological compound such as a protein, if the number of reactive sites thereon is known, by dividing the total luminescence intensity by the number of reactive groups to determine the total amount of protein. However, if the sample contains any other biological compounds having the reactive amine or hydroxyl groups, then the probe will bind to these compounds as well. Thus, in a mixed sample, the measured luminescence will not reflect the concentration of the target but rather will reflect the presence of any and all compounds having these groups. Since most biological compounds do contain these groups, the method is not useful in detecting the presence of a protein in a mixed sample, in a cell, or in situ. In some applications it is possible to first separate the proteins from the rest of the sample and then detect luminescence. However, this requires an additional step, and removes the protein from the sample. As a result, this method is impractical for measurement of protein in situ, protein-protein interactions, and the like.

The Waggoner patent also discloses a two step labeling procedure. First, a primary component such as an antibody is labeled with the dye. Next, the labeled antibody is used as a probe for the secondary component, such as an antigen for which the antibody is specific. Monoclonal antibodies, which bind with specificity to cell surfaces and the like, are particularly useful in this regard. In fact, fluorescein, Texas Red, rhodamine and phycoerythrin labeled monoclonal antibodies are now commercially available. However, application of this method is limited to those secondary components or target materials which bind specifically to a particular monoclonal antibody. Thus, these dyes can only be specific to certain compounds and are therefore limited in their application.

Rather than rely on endogenous reactive groups or antigens as binding sites, it is known to engineer a small receptor motif into the protein as a tag. A dye or probe can then selectively bind to these motifs or targets. Intein mediated labeling or expressed protein ligation and oxidation mediated labeling methods are known methods for labeling receptor motifs at protein termini. However, these methods cannot be used to label internal sites within a protein. In addition, these methods suffer the same drawbacks as the Waggoner probes, as they require removal of excess probe for accurate detection of proteins. As a result, these methods also fail to achieve direct labeling of proteins in cuvettes, gels, blots or biological samples without a further purification step. Furthermore, these probes are unsuitable for in situ detection schemes.

U.S. Pat. No. 6,008,378 to Tsien et al. discloses a bis-arsenical compound useful in detecting the presence of a biological target material. The bis-arsenical compound (known as FlAsH) is used to label proteins by reacting with a target sequence of a thiol containing tetracysteine motif ($Cys_4$). FlAsH may be modified to contain a detectable group such as a fluorescent group. The FlAsH label may be further modified to include dithiol groups for protection against binding to low affinity sites, such as endogenous cysteine residues or dihydrolipoic acid moieties. A preferred dithiol is 1,2-ethanedithiol (EDT). The FlAsH-EDT complex can be non-fluorescent when it is not bound to a target sequence, which can aid in reduction of background noise caused by unbound FlAsH.

The FlAsH compound reacts with a certain amount of specificity to a $Cys_4$ motif target sequence that has been incorporated into the target material. Specifically, the thiol groups of the cysteines in the target sequence react with the arsenical moieties of FlAsH. However, there is significant noise in the system. Although an improvement over other dyes in that unbound probe can avoid contributing to background noise when it is non-fluorescent, the FlAsH-EDT complex has been found to have less specificity to the $Cys_4$ motif than originally thought. In one study, FlAsH-EDT was found to fluoresce significantly when added to protein homogenates from non-transfected cells that lacked the $Cys_4$ motif. Stroffekova, K., *European J. of Physio.*, 442:859-866 (2001). Thus, this system produces background noise whereby the biarsenical compound binds to other sulfur molecules, such as those contained in other cysteine or lysine amino acids, besides those in the target sequence.

In protein analysis, it is often important to not only detect the presence of a protein, but also to determine spatial relationships within a protein or to detect protein-protein interactions.

Fluorescence resonance energy transfer (FRET) is a physical phenomenon that permits measurement of molecular distances. FRET occurs in a system having a fluorescent probe serving as a donor and a second fluorescent probe serving as an acceptor, where the emission spectrum of the donor overlaps the excitation spectrum of the acceptor. In such a system, upon excitation of the donor with light of the donor excitation wavelength, energy can be transferred from the donor to the acceptor, resulting in excitation of the acceptor and emission at the acceptor emission wavelength. With fluorochromes and chromophores known in the art, FRET is useful over distances of about 1 nm to about 15 nm, which are comparable to the dimensions of biological macromolecules and macromolecule complexes. Thus, FRET is a useful technique for investigating a variety of biological phenomena that produce changes in molecular proximity. When FRET is used as a detection mechanism, colocalization of proteins and other molecules can be imaged with spatial resolution beyond the limits of conventional optical microscopy.

Among the most widespread donor acceptor pairs are luminescent cyanine dyes including Cy3/Cy5, and Cy5/Cy7. The pairs typically include a target bonding group capable of forming a covalent bond with a target sequence or target compound.

U.S. Pat. No. 6,130,094 to Waggoner discloses a FRET method using pairs of fluorescent dyes for use as probes which bind to cellular constituents. Low molecular weight fluorescent labeling complexes are used having large wavelength shifts between absorption of one dye and emission from another dye in the complex. The dyes are attached through linkers to form donor-acceptor complexes. FRET from an excited donor to a fluorescent acceptor provide the detectable signal. The dyes contain reactive groups for labeling functional groups on target compounds. A disadvantage of this invention is that the reactive group may not be specific to just the functional group on the target compound. Furthermore, the dyes must first be pre-assembled using the linker before they are added to the sample, and therefore will emit a detectable signal even if not bound to a target material. As a result, less than complete bonding of each complex to targets may generate false positive signals or background noise unless unbound complex is first removed from the sample. This is particularly problematic when attempting to identify small amounts of protein, as is typically the case when observing proteins in living cells. As in the previously described probes, this method is impractical for detection of proteins in cells, in situ or for any direct reading applications.

There is a present need for detectable probes capable of selectively binding to biological target materials in cells, in situ or other indirect reading applications. Accordingly, a need exists for a fluorescent probe which exhibits distinguishable fluorescent characteristics when attached to a target material as opposed to when unattached to target material. A further need exists for a fluorescent probe in which background noise, generally, and non-selective binding to unintended sites, in particular, is reduced. These and further objectives are provided by the methods and probes of the present invention.

SUMMARY OF THE INVENTION

It is an advantage of the present invention that the probe is capable of creating donor acceptor pairs in cells or in situ without the need to first bind the pair together.

It is a further advantage of the present invention that unbound probe will reduce undesirable background noise in detection of bound probe.

In another advantage of the present invention, a probe is provided which may be used in a mixed sample to detect a target material without generating a detectable signal from binding to unintended sites. As a result, there is no need to separate the target material from a sample, either before or after introduction of a probe according to the invention, in order to accurately measure the target material.

As used herein, the terms "target sequence" or "peptide tag" or simply "tag" refer to an amino acid sequence in a target material to which a probe of the present invention selectively associates or binds.

As used herein, the term "target material," "target," or "analyte" refers to a compound of interest that is to be labeled with a probe according to the present invention. Non-limiting examples of targets include a protein, a particular conformation of a protein, a protein-protein interaction, a peptide, a peptide-nucleic acid (PNA), a memetic, an antibody, an antigen, a ligand, a receptor, a hapten, a saccharide, a polysaccharide, and a nucleic acid. Furthermore, the analyte can be part of a cell, such as a bacteria, or a cell bearing a blood group antigen or an HA antigen or a microorganism. The terms "target," "target material," "analyte" and "compound of interest" may be used interchangeably.

As used herein, the term "fluorescent conjugate" refers to a part of the SARP. A first fluorescent conjugate includes a fluorescent compound having a distinct emission and excitation emission from a second fluorescent conjugate in the SARP. The fluorescent conjugates also each include a reactive moiety which is capable of selectively associating with a tag on a target material.

As used herein, the term "self-assembled relay probe" or "SARP" refers to a probe according to the invention. Each SARP includes a pair of fluorescent conjugates. Each of the fluorescent conjugates associates with the target compound via a peptide tag. The paired fluorescent conjugates independently assemble on the target compound in sufficient proximity to perform a detectable energy transfer.

The present invention relates generally to novel methods of detecting a target material in a sample by using a pair of fluorescent conjugates which will each independently associate with the target material. The association results in the fluorescent conjugates being sufficiently proximate to permit a measurable energy transfer therebetween. The tags may be incorporated in any position in any sequence context, provided that the distance between the tags is appropriate for FRET. Preferably, the distance will be in the range of $R_0=0.1$ to $R_0=2$.

In one aspect of the invention, a self-assembled relay probe for detecting a target material is provided. The probe includes a first peptide tag bound to the target material; and a first fluorescent conjugate including a first fluorochrome and a first tag binding group. The first fluorescent conjugate selectively associates with the first peptide tag. Further included in the probe is a second peptide tag bound to the target material; and a second fluorescent conjugate including a second fluorochrome having a longer wavelength excitation and emission maxima than the first fluorochrome and a second tag binding group. The second fluorescent conjugate selectively associates with the second peptide tag. Upon exposure to the target material, the first and second fluorescent conjugates independently associate with the first and second peptide tags, respectively, so as to be a distance apart represented by about $0.1\ R_0$ to about 2 times $R_0$, such that upon excitation of the first fluorescent conjugate, fluorescence resonance energy transfer results in excitation of the second fluorescent conjugate, yielding detectable emission from the second fluorescent conjugate.

In another aspect of the invention, a method of detecting a target material is provided. The method includes the step of: tagging the target material with at least a first peptide tag and a second peptide tag, which is at a distance of about $0.1\ R_0$ to about 2 times $R_0$ from the first peptide tag to form a tagged target material. The method also includes: exposing the sample to a first fluorescent conjugate including a first fluorochrome, the first conjugate being capable of selectively associating with the first peptide tag; and exposing the sample to a second fluorescent conjugate including a second fluorochrome having a distinct excitation and emission maxima from the first fluorochrome, the second conjugate being capable of selectively associating with the second peptide tag. The method further includes allowing the first and second fluorescent conjugates to associate with the tagged target material, wherein the first and second fluorescent conjugates independently assemble on the target material by associating with the first and second peptide tags, respectively, so as to form a self assembled relay probe (SARP), such that upon excitation of the first fluorescent conjugate, fluorescence energy transfer results in excitation of the second fluorescent conjugate. Also included in the method are the steps of: exposing the sample containing the SARP to light of a suitable wavelength for the excitation of the first fluorescent conjugate to occur; and detecting the energy transfer.

In another aspect of the present invention, a method for monitoring a reaction between analytes in a sample is provided. The method includes the steps of: providing a first analyte in a sample, the first analyte having bound thereto at least a first and second peptide tag, wherein a distance between the tags is from about 0.1 to about 2 times $R_0$; and exposing the sample to a first fluorescent conjugate which selectively associates with the first tag. The method also includes allowing the first analyte to react with a second analyte labeled with a second fluorescent conjugate which selectively associates with the second tag, wherein the second conjugate is capable of participating in fluorescence energy transfer with the first fluorescent conjugate. Further included in the method are the steps of: exposing the sample to light of a suitable wavelength to allow the energy transfer to occur between the fluorescent conjugates; and monitoring the reaction between the analytes by monitoring a detectable signal generated as a result of the energy transfer between the fluorescent conjugates.

The present invention also provides a composition including a first peptide tag/spacer/second peptide tag module, wherein: (i) the first peptide tag is of the form $C(X_i)C$, wherein X is any amino acid, C is Cysteine and i is 0-6; (ii) the second peptide tag is of the form: $C(X)_iC(X)_jC(X)_kC$, where C is Cysteine, X is an amino acid, and i, j, and k are each independently 0 or an integer of from 1 to 8; and (iii) the spacer, which separates the first and second peptide tags is of the form $(X)_n$, where X is any amino acid and n is an integer from about 6 to about 26.

Further provided herein is a recombinant nucleic acid sequence encoding a first peptide tag/spacer/second peptide tag module, wherein: (i) the first peptide tag is of the form $C(X_i)C$, wherein X is any amino acid, C is Cysteine, and i is 0-6; (ii) the second peptide is of the form: $C(X)_iC(X)_jC(X)_kC$, wherein C is Cysteine, X is an amino acid, and i, j, and k are each independently 0 or an integer of from 1 to 8; and (iii) the spacer, which separates the first and second peptide tags is of the form $(X)_n$, where X is any amino acid and n is an integer from about 6 to about 26. Such a recombinant nucleic acid sequence can be included within a kit.

Moreover, the present invention provides a composition including an isolated or recombinant nucleic acid sequence encoding (a) at least one target material; and (b) a first peptide tag/spacer/second peptide tag module, wherein (i) the first peptide tag is of the form: $C(X_i)C$, wherein X is any amino acid, C is Cysteine and i is 0-6; (ii) the second peptide tag is of the form $C(X)_iC(X)_jC(X)_kC$, wherein C is Cysteine, X is an amino acid, and i, j, and k are each independently 0 or an integer of from 1 to 8; and (iii) the spacer, which separates the first and second peptide tags, is of the form $(X)_n$, where X is any amino acid and n is an integer from about 6 to about 26.

Other features and advantages of the invention will become apparent from the following detailed description and accompanying drawings in which like numerals represent like elements throughout the several views.

BRIEF DESCRIPTION OF THE DRAWINGS

FIG. 1 shows one embodiment of the fluorescence labeling technology of the present invention.

FIG. 13 A. shows the results for multicolor, multisite labeling with probes FlAsH and Cy5-$(SO_3)_2$-$(PAEDT)_2$ and doubly-tetracysteine-tagged protein "α-SARP-P3/G1-PP9"; B. shows the results for multicolor, multisite labeling with probes FlAsH and Cy5-$(SO_3)_2$-$(PAEDT)_2$ and doubly-tetracysteine-tagged protein "α-SARP-P4/G1-PP9".

DETAILED DESCRIPTION OF THE PREFERRED EMBODIMENTS

Figure 2:
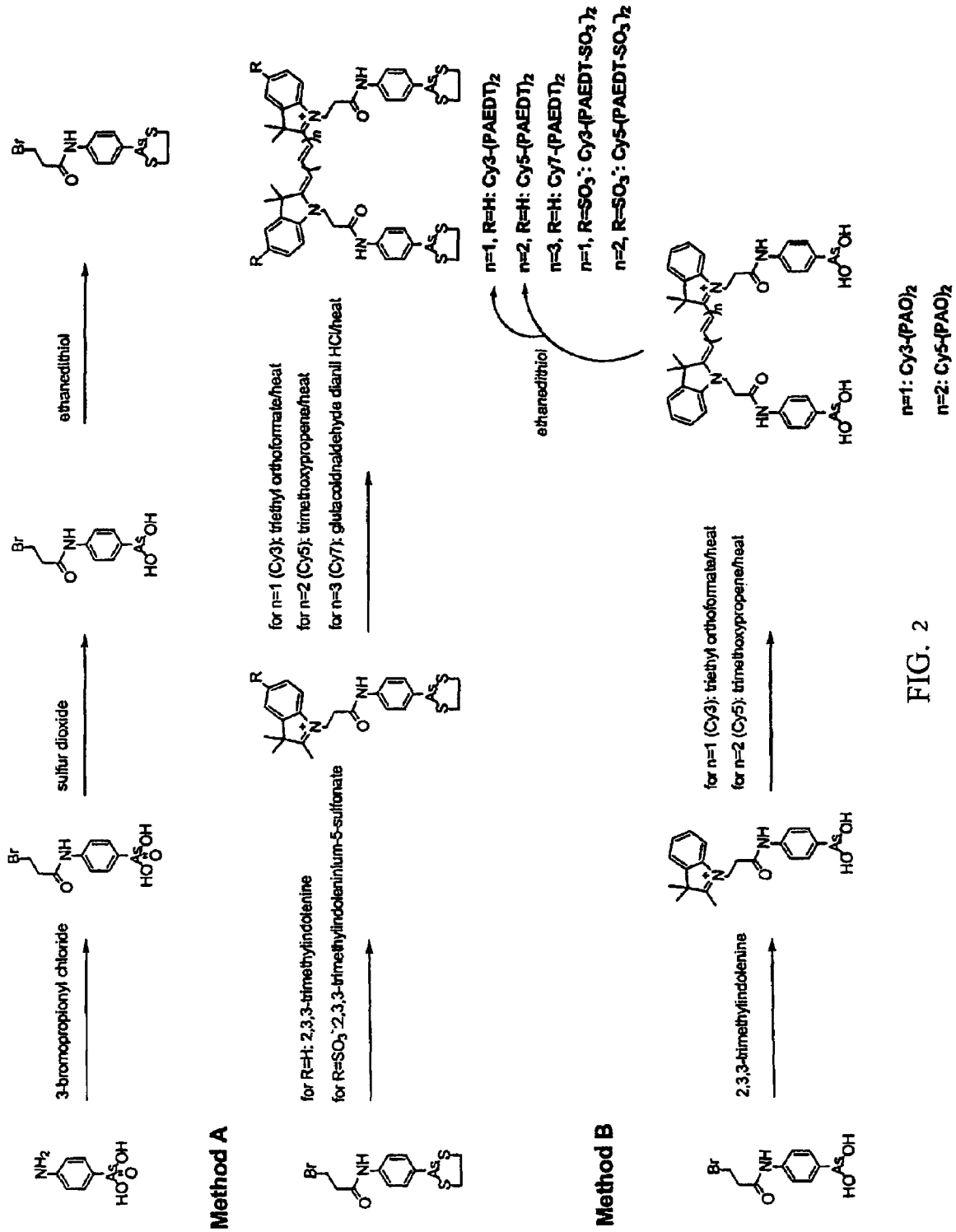
FIG. 2 shows methods for synthesizing certain bis arsenical containing fluorescent conjugates of the probe of the present invention.

The principle of operation of SARPs is to apply the principles of FRET to obtain a detectable signal from two fluorescent conjugates arranged in sufficient proximity to one another on a target material. Two peptide tags are therefore provided on the target material in sufficient proximity, so that when the first and second fluorescent conjugates associate with their respective tags, a detectable energy transfer occurs. In desired embodiments, the first and second peptide tags are different. A variety of fluorescent conjugates, as well as the tags to which they selectively associate, are further discussed infra.

FIG. 1A shows one embodiment of the fluorescence labeling technology of the present invention, as compared to fluorescent labeling with conventional fluorochromes (1B). In FIG. 1A, the SARP is a composite probe formed by self-assembly of two biarsenical fluorochromes $F_1$, and $F_2$, with a target material containing two tetracysteine tags, $T_1$ and $T_2$. The probe is detected by providing excitation maximum of $F_1(\lambda_{exc,F1})$ and monitoring emission at the emission maximum of $F_2$ ($\lambda_{exc,F2}$)FRET. A SARP in FIG. 1A exhibits minimal interference from background due to non-specifically incorporated fluorochrome and free fluorochrome-due to insufficient proximity for $F_1$-$F_2$ FRET (middle and bottom panels of 1A). This is in contrast to conventional fluorochromes (1B),which exhibit substantial interference from non-specifically-bound and free fluorochrome (middle and bottom panels of 1B).

As described above, the target material contains (or is modified to contain) at least two peptide tags. However, it is well within the contemplation of this invention that a target material can include more than two tags. For example, the probe of the present invention can include a third peptide tag, and a third fluorescent conjugate wherein the third fluorescent conjugate selectively associates with the third tag and is capable of participating in a relay energy transfer with one of the first and second fluorescent conjugates. The first, second and third tags can be different.

As discussed above, FRET occurs in a system having a fluorescent material serving as a donor and a second fluorescent material serving as an acceptor, where the emission spectrum of the donor overlaps the excitation spectrum of the acceptor. In such a system, upon excitation of the donor with light of the donor excitation wavelength, energy can be transferred from the donor to the acceptor, resulting in excitation of the acceptor and emission at the acceptor emission wavelength.

FRET readily can be detected—and the efficiency of FRET readily can be quantified—by exciting with light of the donor excitation wavelength and monitoring emission of the donor, emission of the acceptor, or both. The efficiency of energy transfer, E, is a function of the Förster parameter, $R_0$, and of the distance between the donor and the acceptor, R:

$$E=[1+(R/R_o)^6]^{-1}$$

wherein the Förster parameter (in angstroms, Å), is:

$$R_0(\text{in Å})=(0.211\times 10^{-5})(n^{-4}Q_{DK}{}^2J)^{1/6}$$

wherein n is the refractive index of the medium, $Q_D$ is the donor quantum yield in the absence of the acceptor, $\kappa^2$ is the orientation factor relating the donor acceptor transition dipoles, and J is the spectral overlap integral of the donor emission spectrum and the acceptor excitation spectrum.

If one performs FRET experiments under conditions where $R_0$ is constant, measured changes in E permit detection of changes in R, and, if one performs experiments under conditions where $R_0$ is constant and known, the measured absolute magnitude of E permits determination of the absolute magnitude of R.

Self-Assembled Relay Probes (SARP)

A SARP according to the invention will generate a detectable signal when the fluorescent conjugates of the probe are within from about 0.1 $R_0$ to about 2 times $R_0$ from one another. In desired embodiments, the tags are within less than about 100 angstroms (Å) from one another, preferably from about 10 Å to about 100 Å from one another. The fluorescent conjugates possess distinct emission and excitation spectra. Preferably, the signals generated by the conjugates are discernible from one another, and bound conjugates are discernible from unbound conjugates. Also, preferably, the conjugates generate a signal discernible from background autofluorescence of the biological target material. When used in applications involving living cells, the fluorescent conjugates of the SARP are preferably capable of traversing a biological membrane. To this end, it is preferred that the individual fluorescent conjugates are each less than 800 Daltons in diameter.

The Förster parameter or energy transfer radius, $R_0$, is the distance between the fluorescent pairs necessary to achieve 50% efficiency in performing FRET. As the pairs become more distant, efficiency of energy transfer decreases. Although it is possible for some signal to be generated at any point in excess of 0%, an optimal distance for fluorescent conjugates of the invention is from about 0.1 to about 2 times $R_0$, which is equal to an energy transfer efficiency of from about 10% to about 100%. More desirably, the distance between fluorescent conjugates of the invention is equal to or greater than about $R_0$, representing an energy transfer efficiency of equal to or greater than about 50%.

Generally, the fluorescent conjugates are one of two types. In one type, the conjugate includes a fluorescent compound and a non-peptide binding group which is capable of selectively associating with a peptide tag. In this case, the tag may be an exogenous cysteine- or histidine-containing sequence. The selectivity of association of the tag binding group to the tag is related to the distance between available reactive sites on the tag. Desirably, the available binding sites on the exogenous sequence are distinct from those of endogenous peptide sequences. The tag binding group is relatively non-selective for endogenous peptide sequences and other biological components while being selective for the exogenous tag.

The other type of fluorescent conjugate includes a fluorescent compound and a peptide binding group, which is capable of selectively associating with a peptide tag. The tag may be a peptide or polypeptide having a high affinity to and selectivity for the binding group. The selectivity of association of this tag binding group to the binding group is related to presence of a recognition site on the tag for the hapten. Examples of peptide binding groups and tags with which they selectively associate include: biotin/anti-biotin, biotin/avidin, biotin/streptavidin, digoxigenin (DIG)/anti-DIG, and the like. These binding groups are relatively non-selective for endogenous peptide sequences and other biological components while being selective for the recognition site on their tags. Selection of appropriate fluorescent conjugates and their associated tag is determined by a variety of factors including the target material, the environment in which the target material may be found, the intended method of detection, and so on.

The probes of the present invention self-assemble in situ, avoiding the limitations of the prior art of Waggoner, in which probes include pre-assembled FRET pairs joined by a linker and are detected regardless of whether or not they are associated with a target material. Furthermore, the probes of the present invention are more versatile as compared to prior art probes such as monoclonal antibodies used in typical FRET applications, which rely on their association in specific binding pairs (SBPs) to be arranged a proper distance from one another. The fluorescent conjugates of the present invention assemble independently on the target material. As a result, SARPs can be used to detect virtually any biological analyte or analytes to which two or more tags may be bound.

In the foregoing description, SARPs have been discussed as performing a detectable energy transfer when the fluorescent conjugates of the probe are arranged in sufficient proximity to perform FRET. However, it is well within the contemplation of the inventors to use a donor/quencher dye pair in which the fluorescent signal is quenched when the pair is in sufficient proximity. In this case, when the pair is separated, then a detectable signal is generated. This can be used, for example, in conformation change experiments, where the conformational change separates the SARP resulting in a detectable signal upon separation of the paired fluorescent conjugates.

The selectivity of the SARP to the target material is twofold. First, the fluorescent conjugates must selectively associate with their respective tags. Second, the tags must be in sufficient proximity to one another in order to allow the SARP to perform a detectable energy transfer. As a result, even if one or both of the fluorescent conjugates does not possess high selectivity for its tag, it will generate a discernable signal when it is in sufficient proximity to the other fluorescent conjugate. Thus, the likelihood that an unbound or non-selectively bound fluorescent conjugate will be in sufficient proximity to the other fluorescent conjugate in the pair is very low.

Furthermore, a chance arrangement of unbound or non-selectively bound fluorescent conjugate coming in sufficient proximity to another unbound or non-selectively bound fluorescent conjugate in the pair will normally be a transient event and therefore generate a signal temporally discernable from that of the properly situated probe. For example, steady state and nanosecond time resolved fluorescence anisotropy measurements may be used to differentiate efficiency of energy transfer related to donor-acceptor distances as opposed to rapid reorientation of donor and acceptor. Accordingly, SARPs according to the present invention provide a compound reduction in background noise as compared to probes and methods of the prior art.

The reduction of noise in this system eliminates the necessity to purify or separate a target material from a sample prior to analysis. Thus, the probe and methods of the invention are particularly suited for mix and read assays. The SARP may be contacted with a tagged target material located, for example, in a test tube, a microtiter-plate well, or immobilized on a surface or other solid phase. The probe and methods of the invention are also particularly suited for detecting real time events in cells or in situ. It is to be understood, therefore, that many of the methods of using SARPs as herein described, are applicable for use on or in living cells, tissues, organs and organisms.

In an advantageous aspect of the invention, a first fluorescent conjugate includes a donor dye and a second fluorescent conjugate includes an acceptor dye having a distinct excitation and emission maxima from the donor dye. More desirably, the tags are two different tags, with a first fluorescent conjugate selectively associating with the first tag, and a second fluorescent conjugate selectively associating with the second tag.

When used in applications involving detection of the presence of nucleotides, the target nucleotide may be derivatized to a peptide nucleotide which contains a peptide marker, the lac operator. A particularly desirable conjugate for use in detecting nucleotides in cells or in situ is a fluorescently labeled lac repressor. The lac repressor will selectively associate on a nucleotide strand at a position in which lac operator is present. Using this system, it is possible to visualize chromosomes in vivo using lac operator-repressor binding. For a discussion of using lac operator/repressor in chromosomes, see Belmont and Straight, *Cell Biology*, 8:121-123 (1988).

Arsenic-Containing Fluorescent Conjugates

Suitable fluorescent conjugates for use in SARPs according to the present invention include those which bind with selectivity to certain cysteine-containing tags. Useful arsenic-containing fluorescent conjugates include those of the following general structural Formulae (IA) and (IB):

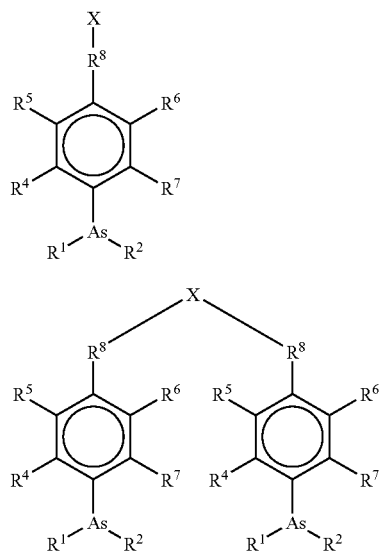

wherein:
(i) each $R^1$ or $R^2$, independently, is $O^-$, $S^-$, $OR^c$ or $SR^c$ with the provision that if either $R^1$ or $R^2$ is absent, the other remaining group is =O or =S; or $R^1$ and $R^2$, together with the arsenic atom, form a ring according to one of the general structural Formulae (II), (III), (IV), or (V):

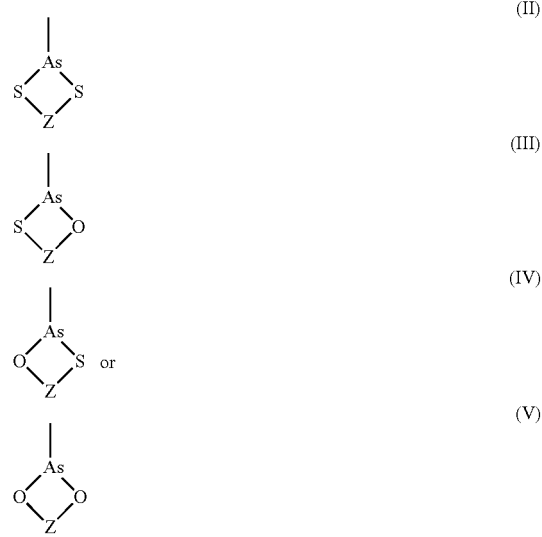

wherein $R^c$ is H, $CH(OH)CH_2OH$ or $(CH_2)_q$—Y, wherein q is 1-4, and Y is H, OH, $NH_2$, SH, COOH, OAc, $CONH_2$ or CN;

and Z represents a hydrocarbon chain comprising 2-4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thio, halo (fluoro, chloro, bromo, or fluoro) and $(CH_2)_{n''}SO_3$, wherein n" is 1 or 2;

(ii) $R^4$, $R^5$, $R^6$ and $R^7$ are each independently H, F, $OR^c$, $R_c$, OAc, $NR^c$, $NH_2$, $N(C_{1\ alkyl})_2$, $R^1$; or $R^4$ with $R^5$, or $R^6$ together with $R^7$, or both, form a ring;

(iii) $R^8$ is a linear or branched optionally substituted spacer having a minimum length of approximately 1.5 and a maximum length of approximately 15 Angstroms; and (iv) X is a fluorochrome.

Some examples of Z include: 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl.

In a desired embodiment, $R^1$ and $R^2$, together with the arsenic atom, form a ring according to one of the general Formulae (II), (III), (IV), or (V) when Z is $CH_2SO_3$.

Desirably, $R^8$ is a linear or branched linker having a minimum length (when fully extended) of about 1.5, preferably 2.5, more preferably 3.5 and most preferably 4.5 angstroms (Å) and having a maximum length (when fully extended) of about 15, preferably 12.5, more preferably 10, and most preferably 7.5 angstroms (Å). Desirably, $R^8$ is about 2-4 atoms long. Examples of desirable chains for $R^8$ include: $-(CH_2)_{1-7}-C(O)NH-$, preferably $-(CH_2)_2C(O)NH$.

Details of how to synthesize the bis-arsenical molecule according to Formula (IB) are described in FIG. 2 and in the Examples. Additionally, details regarding synthesis of this compound are included in the U.S. Patent Application filed under the title: "Reagents And Procedures for High Specificity Labeling" to Ebright, R. et al., filed on Jun. 14, 2002, application No. 60/388,699, attorney docket No. 744-34P, which is hereby incorporated by reference in its entirety. Details regarding the synthesis of the compound of Formula (IB) can also be found in U.S. application Ser. No. 10/461,224, filed Jun. 13, 2003, and published on Jan. 29, 2004 under Publication No. US 2004/0019104A1, which is also incorporated herein by reference in its entirety.

Other Arsenic-Containing Fluorescent Conjugates

Other suitable fluorescent conjugates for use in SARPs include biarsenical compounds known in the art as FlAsH or ReAsH compounds. These may be used as one of the SARP fluorescent conjugates according to the invention. A FlAsH or ReAsH biarsenical molecule has the following general structural Formula (VI), including tautomers, anhydrides, and salts thereof:

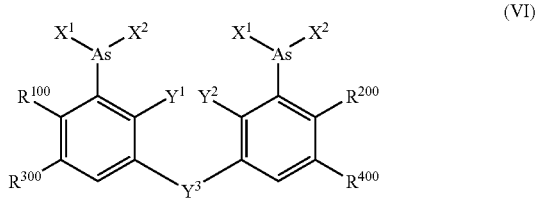

wherein each $X^1$ or $X^2$, independently is Cl, Br, I, $OR^a$, or $SR^a$, or $X^1$ and $X^2$ together with the arsenic atom form a ring having the structure:

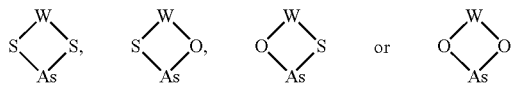

$R^a$ is H, $C_1$-$C_4$ alkyl, $CH_2CH_2OH$, $CH_2COOH$, or CN;
W is 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl;
$Y^1$ and $Y^2$, independently, are H or $CH_3$; or
$Y^1$ and $Y^2$, together form a ring such that the biarsenical molecule has the general structure formula:

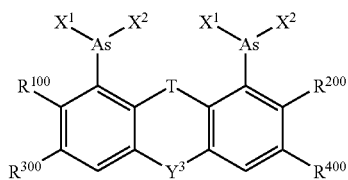

wherein T is O, S, $CH_2$, $C(CH_3)_2$, or NH;
$R^{100}$ and $R^{200}$, independently, are $OR^a$, OAc, $NR^aR^b$, or H;
$R^{300}$ and $R^{400}$, independently, are H, F, Cl, Br, I, $OR^a$, or $R^a$; or
$R^{100}$ together with $R^{300}$ or $R^{200}$ together with $R^{400}$, or both, form a ring in which
  (i) one of $R^{100}$ or $R^{300}$ is $C_2$-$C_3$ alkyl and the other is $NR^a$ and
  (ii) one of $R^{200}$ and $R^{400}$ is $C_2$-$C_3$ alkyl and the other is $NR^a$;
$R^b$ is H, $C_1$-$C_4$ alkyl, $CH_2CH_2OH$, $CH_2COOH$, or CN;
$Y^3$ is $CR^aR^b$, $CR^aOR^b$, C=O, or a spirolactone having one of the structures:

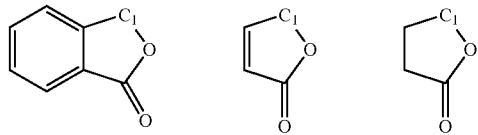

wherein the spiro linkage is formed at $C_1$.

The conjugate according to Formula (VI) for use with the present invention is substituted at one or more positions of Formula (VI) so as to add a signal-generating detectable group. In some embodiments, the detectable group is selected from fluorescein, resorufin and derivatives thereof. Desirably, the detectable group at one or more positions of Formula (VI) is fluorescein (FlAsH) or resorufin (ReAsH)

Examples of these bis-arsenical compounds for purposes of the present invention may be found, for example, in U.S. Pat. No. 6,008,378 to Tsien et al. or U.S. Pat. No. 6,451,569 B1 to Tsien, et al., the entirety of each of which is incorporated herein by reference. A suitable ReAsH compound for purposes of the present invention is described by Adams, et al. in J. Am. Chem. Soc. (2002) 124, 6063-6076, which is incorporated herein by reference.

Transition Metal-Containing Fluorescent Conjugates

Additionally, certain mono-transition metal fluorochrome molecules are useful conjugates. A molecule according to the following general structural Formula (VII) is useful:

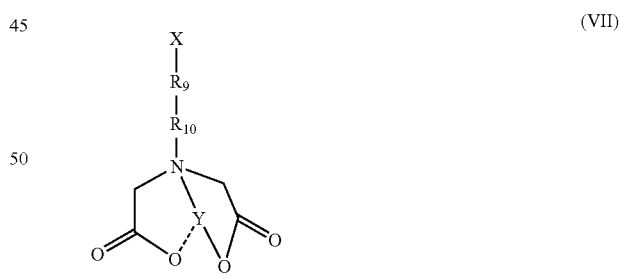

wherein: (a) Y is a transition metal, (b) $R_9$ is $C(COO^-)$, CH(COOH), or absent; (c) $R_{10}$ is a linker having a length of from about >0 to about 20 angstroms (Å); and (d) X is a detectable group. The linker may linear or branched, may contain aromatic moieties, and optionally may be further substituted.

Preferred is a bidentate $Ni^{2+}$:nitrilotriacetic acid (($Ni^{2+}$:$NTA)_2$) complex according to the following general structural Formula (VIII):

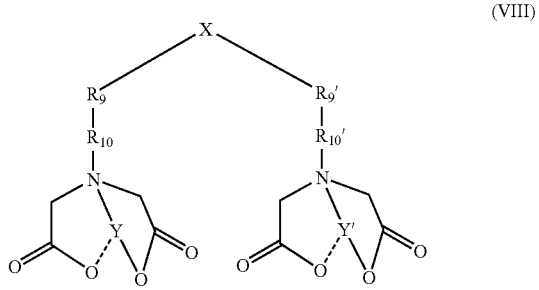

(VIII)

wherein: (a) Y and Y' are each a transition metal, (b) $R_9$ and $R_9'$ are each independently $C(COO^-)$, $CH(COOH)$, or absent; (c) $R_{10}$ and $R_{10'}$ are linkers each having a length of from about >0 to about 20 angstroms (Å); and (d) X is a detectable group. Preferably, the linkers are identical in length, and are from about 3 to about 15 Å long. The linkers may be linear or branched, may contain aromatic moieties, and optionally may be further substituted.

Figure 3:
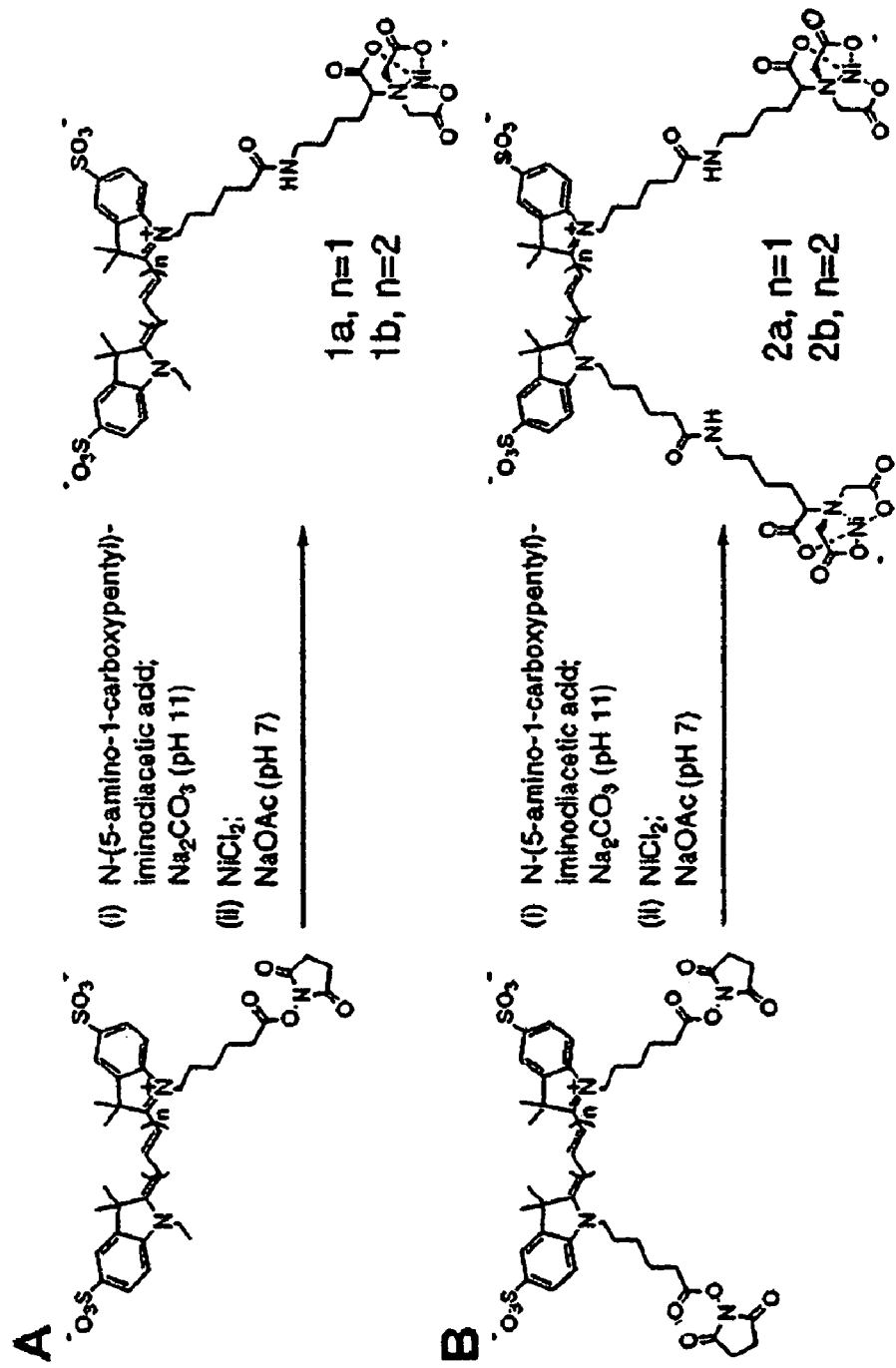
FIG. 3 shows methods for synthesizing certain transition metal containing fluorescent conjugates of the probe of the present invention. Part A of this figure shows the synthesis of $(Ni^{2+}-NTA)_1$-Cy3 (1a) and $(Ni^{2+}-NTA)_1$-Cy5 (1b). Part B of this figure shows the synthesis of $(Ni^{2+}-NTA)_2$-Cy3 (2a) and $(Ni^{2+}-NTA)_2$-Cy5 (2b). Part B of this figure shows the FIGS. 4 and 5 show results of fluorescence anisotropy experiments verifying specific interactions between bis-transition metal containing fluorescent conjugates of the invention with hexahistidine-tagged polypeptides.

Generally, the transition metal containing conjugates may be made by coupling a fluorescent compound having a bis-activated ester derivative with an amine or hydrazine derivative of a chelator, and adding a transition metal. Such fluorescent compounds are available commercially, and may be derivatized according to methods generally known to those having skill in the art. Refer to FIG. 3 for a synthesis scheme for making a transition metal containing fluorescent conjugate according to general structural Formulae (VII and VIII).

In one particularly advantageous synthesis route, a bidentate transition metal conjugate (including a non-sulfonated cyanine or squarine moiety) is formed by first coupling: (a) a synthon selected from a mono-chelator-functionalized 2,3,3-trimethylindole, a mono-chelator-functionalized 2,3,3-trimethylbenzindole, a mono-chelator-functionalized 2-methyl-pyridine, a mono-chelator-functionalized 2-methyl-benzothiazole, a mono-chelator-functionalized 2-methyl-napthothiazole, a mono-chelator-functionalized 2-methyl-benzoxazole, and a mono-chelator-functionalized 2-methyl-napthoxazole with (b) a synthon identical or nonidentical to the synthon in (a), and (c) a synthon containing at least one carbon atom; and then adding a transition metal.

In a further advantageous synthesis route, a conjugate including a disulfonated cyanine or squaraine moiety is formed by first coupling (a) a synthon selected from a mono-chelator-functionalized 2,3,3-trimethyl-5-sulfanato-indole, a mono-chelator-functionalized 2,3,3-trimethyl-6-sulfanato-benzindole, a mono-chelator-functionalized 2-methyl-5-sulfanato-pyridine, a mono-chelator-functionalized 2-methyl-5-sulfanato-benzothiazole, a mono-chelator-functionalized 2-methyl-6-sulfanato-napthothiazole, a mono-chelator-functionalized 2-methyl-5-sulfanato-benzoxazole, and a mono-chelator-functionalized 2-methyl-6-sulfanato-napthoxazole; with (b) a synthon identical or nonidentical to the synthon in (a); and (c) a synthon containing at least one carbon atom; and then adding a transition metal.

Additional methods of synthesis of monosulfonated cyanine or squaraine compounds of the present invention include coupling of: (a) a synthon selected from mono-chelator-functionalized 2,3,3-trimethylindole, mono-chelator-functionalized 2,3,3-trimethylbenzindole, mono-chelator-functionalized 2-methyl-pyridine, mono-chelator-functionalized 2-methyl-benzothiazole, mono-chelator-functionalized 2-methyl-napthothiazole, mono-chelator-functionalized 2-methyl-benzoxazole, and mono-chelator-functionalized 2-methyl-napthoxazole; (b) a synthon selected from mono-chelator-functionalized 2,3,3-trimethyl-5-sulfanato-indole, mono-chelator-functionalized 2,3,3-trimethyl-6-sulfanato-benzindole, mono-chelator-functionalized 2-methyl-5-sulfanato-pyridine, mono-chelator-functionalized 2-methyl-6-sulfanato-benzothiazole, mono-chelator-functionalized 2-methyl-6-sulfanato-napthothiazole, mono-chelator-functionalized 2-methyl-5-sulfanato-benzoxazole, and mono-chelator-functionalized 2-methyl-6-sulfanato-napthoxazole; and (c) a synthon containing at least one carbon atom; and then adding a transition metal.

Coupling of the synthons referred to herein can be accomplished in a single step, or in two steps. For example, for symmetric compounds (i.e., where (a) and (b) are identical), coupling of the reactants (a), (b), and (c) desirably is carried out in a single step. For asymmetric compounds (i.e., where (a) and (b) are non-identical), coupling of the reactants (a), (b), and (c) desirably is carried out in two steps: i.e., reaction of (a) with (c), followed by reaction of the resultant product with (c); or, alternatively, reaction of (b) with (c), followed by reaction of the resultant product with (a).

Coupling of the synthons referred to herein can be performed in solution, or with one or more synthons attached to a solid support.

Coupling of the synthons referred to herein can be performed with the chelator in an unprotected form, or with the synthon in a protected form initially and deprotected thereafter.

The invention also provides methods of synthesis of xanthene, xanthanone, or phenoxazine compounds of the present invention which include reaction of a xanthene, xanthanone, or phenoxazine detectable group, a secondary-amine derivative of a chelator, and formaldehyde, according to the Mannich reaction (Mannich, C. et al. *Arch. Pharm.* 250:647, 1912); followed by addition of a transition metal. The Mannich reaction referred to herein can be performed with the chelator in an unprotected form, or with the chelator in a protected form initially and deprotected thereafter.

Further details regarding synthesis of these conjugates can be found in PCT Patent Application by Dr. Richard Ebright et al. entitled "Bis-Transition-Metal Chelate Probes" filed on Nov. 12, 2002, having serial no. PCT/US 02/36180, the entirety of which is hereby incorporated by reference.

Fluorescent Conjugates

The fluorescent conjugates of the present invention include compounds that emit detectable light, are luminescent, or fluorescent. A luminescent dye may, for example, include cyanine and related dyes, such as merocyanine, styryl and oxonol dyes, which are strongly light-absorbing and highly luminescent. Fluorescein may also be used.

In one desired embodiment, each of the first and second fluorochromes of the probe of the present invention is selected from the following: a fluoroscein dye, a cyanine dye, a squaraine dye, a rhodamine dye and a near infrared dye. The first and second fluorochromes can be different.

Any compound including a fluorochrome capable of performing FRET may be used as a fluorescent conjugate as long as the SARP fluorescent conjugates are able to associate with some selectivity to a target material. The only limitation is that the fluorescent conjugates may not be so large as to interfere with their ability to associate with their tags or to be arranged in sufficient proximity to one another to perform a detectable energy transfer.

The fluorochrome represented by "X" in the general structural Formulae (IA), (IB), (VI), (VI) and (VIII), or the FlAsH or ReAsH molecule, is detected by monitoring a light emission or energy transfer signal. Some signals which may be monitored due to the presence of a detectable group include, for example, fluorescence (fluorescence emission intensity, fluorescence lifetime, fluorescence polarization, fluorescence anisotropy or fluorescence correlation), fluorescence quenching, or exciton formation. The signal may result from association of the SARP to adjacent tags or association of the SARP to further relay probes. The signal may be generated as a result of receptor-binding, protein-protein or protein-nucleic acid crosslinking, and protein or nucleic acid cleavage.

Preferred detectable groups for X include fluorescent moieties. In one preferred embodiment, cyanine fluorescent moieties are used. These include, but are not limited to: Cy3: 1-R-2-[3-[1-R-1,3-dihydro-3,3-dimethyl-5-sulfo-2H-indol-2-ylidene]-1-propeny l]-3,3-dimethyl-5-sulfo-3H-indolium, Cy5: 1-R-2-[5-[1-R-1,3-dihydro-3,3-dimethyl-5-sulfo-2H-indol-2-ylidene]-1,3-penta dienyl]-3,3-dimethyl-5-sulfo-3H-indolium, Cy7: 1-R-2-[7-[1-R-1,3-dihydro-3,3-dimethyl-5-sulfo-2H-indol-2-ylidene]-1,3,5-heptatrienyl]-3,3-dimethyl-5-sulfo-3H-indolium, indocyanine green and IRDye (1-R-2-[2-[2-R'-3-[(1-R-1,3-dihydro-3,3-dimethyl-5-sulfo-2H-indol-2-ylidene) ethylidene]-1-cyclohexen-1-yl] ethenyl]-3,3-dimethyl-5-sulfo-3H-indolium), and mono- and non-sulfonated derivatives thereof. In another preferred embodiment, squaraine fluorescent moieties are used. In another preferred embodiment, xanthene, xanthanone, and phenoxazine fluorescent moieties are used.

Examples of cyanine, squaraine, xanthene, xanthanone, and phenoxazine detectable groups fluorescent moieties are described, inter alia, in Southwick et al., 1990, *Cytometry* 11:418-430; Mujumdar et al., 1993, *Bioconjugate Chemistry* 4:105-111; Waggoner and Ernst, *Fluorescent Regents for Flow Cytometry, Part 1: Principles of Clinical Flow Cytometry* (1993) and Haugland, *Molecular Probes Handbook of Fluorescent Probes and Research Chemicals, Molecular* Inc. 6th edition (1996) and Berling and Reiser, *Methoden der Organischer Chemie*, p 231-299 (1972), Oswald et al., *Analytical Biochemistry* 280: 272-277 (2000), Oswald et al. *Photochemistry and Photobiology* 74(2): 237-245 (2001), Oswald et al. *Bioconjugate Chemistry* 10: 925-931 (1999), U.S. Pat. No. 6,086,737. The structures in these publications are all incorporated herein by reference.

In a preferred embodiment, X may be selected from the following cyanine detectable groups:

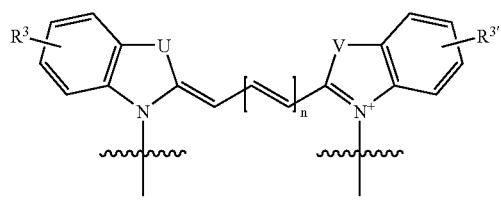

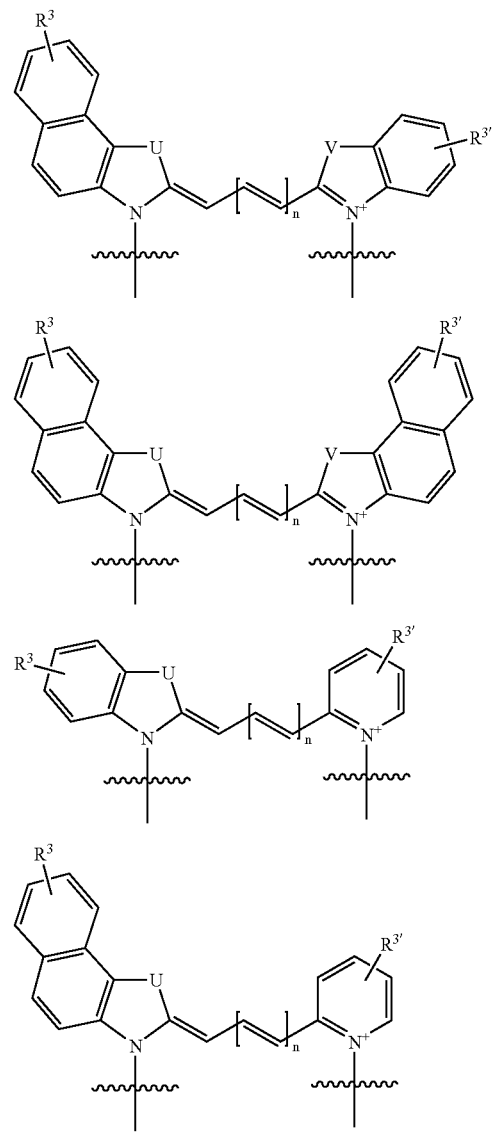

wherein U and V are each independently $C(R^f)_2$, NH, O, S, or $(CH)_2$; $R^3$ and $R^{3'}$ are each independently H or sulfonate; $R^f$ is H, $CH_3$, $CH_2CH_3$, or $(CH_2)_2CH_3$; and n is 0 or an integer of from 1 to 6.

In another preferred embodiment, X may be selected from the following squaraine detectable groups:

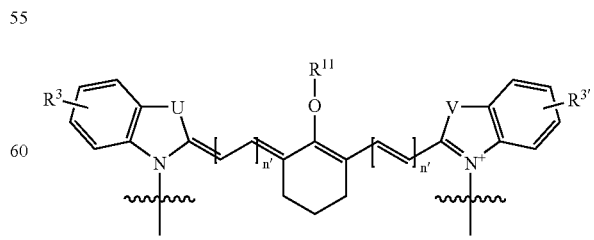

-continued

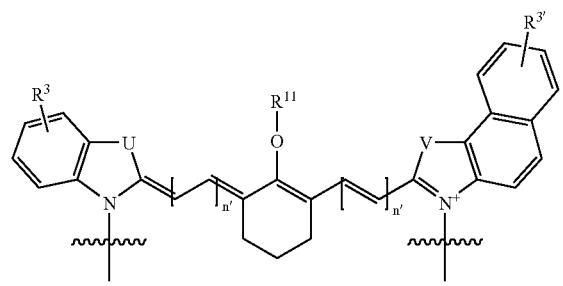

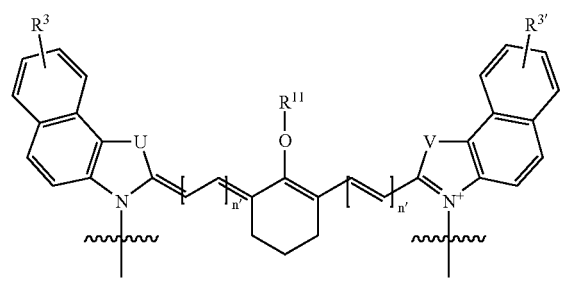

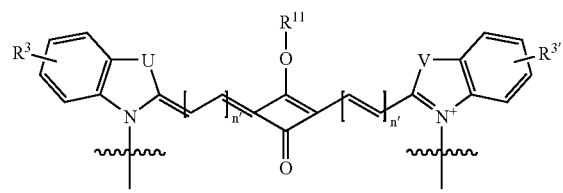

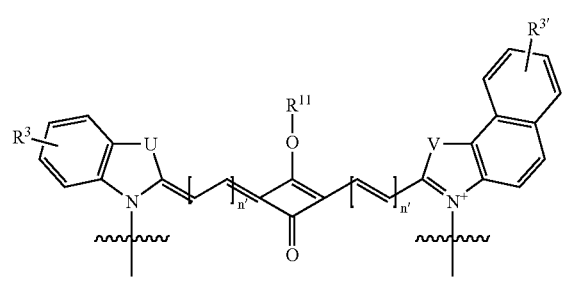

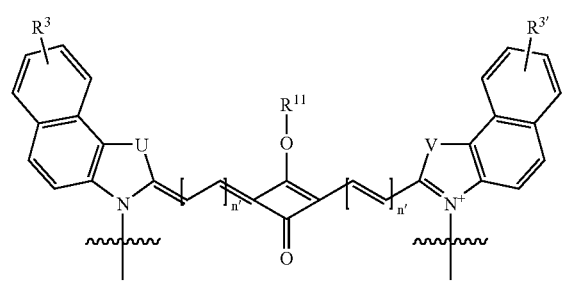

-continued

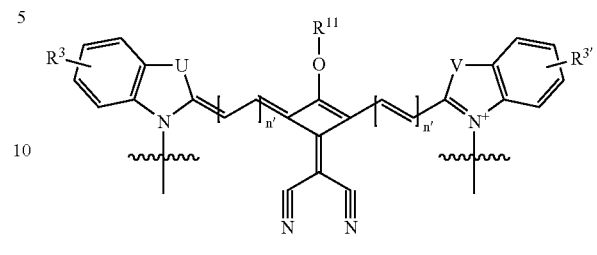

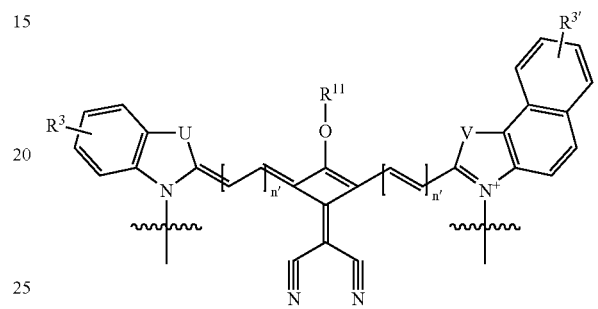

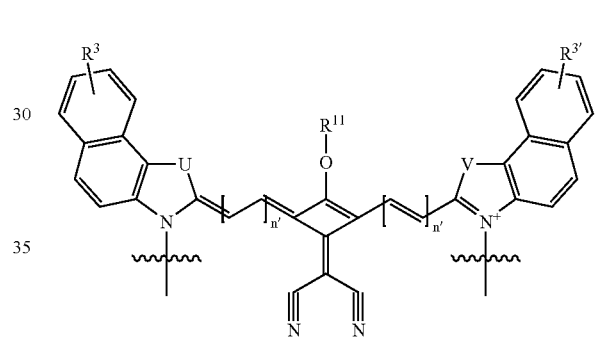

wherein U and V are each independently $C(R^g)_2$, NH, O, S, or $(CH)_2$; $R^3$ and $R^{3'}$ are each independently H or sulfonate; $R^g$ is H, $CH_3$, $CH_2CH_3$, or $(CH_2)_2CH_3$; $R^{11}$ is absent or is selected from the group consisting of H, an alkyl group, and an aryl group; and n' is 0 or an integer of from 1 to 3.

In another preferred embodiment, X may be selected from the following xanthene, xanthanone, and phenoxazine detectable groups:

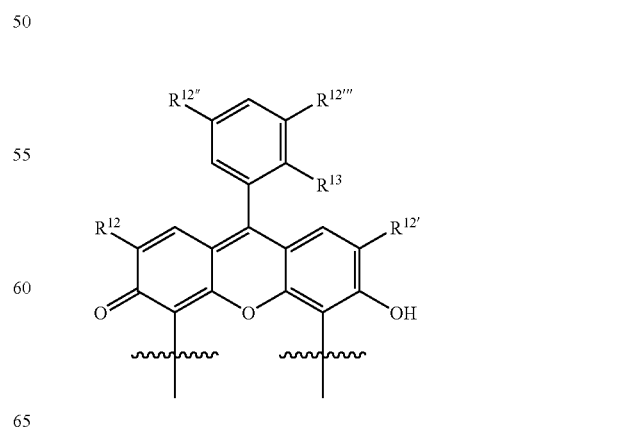

-continued

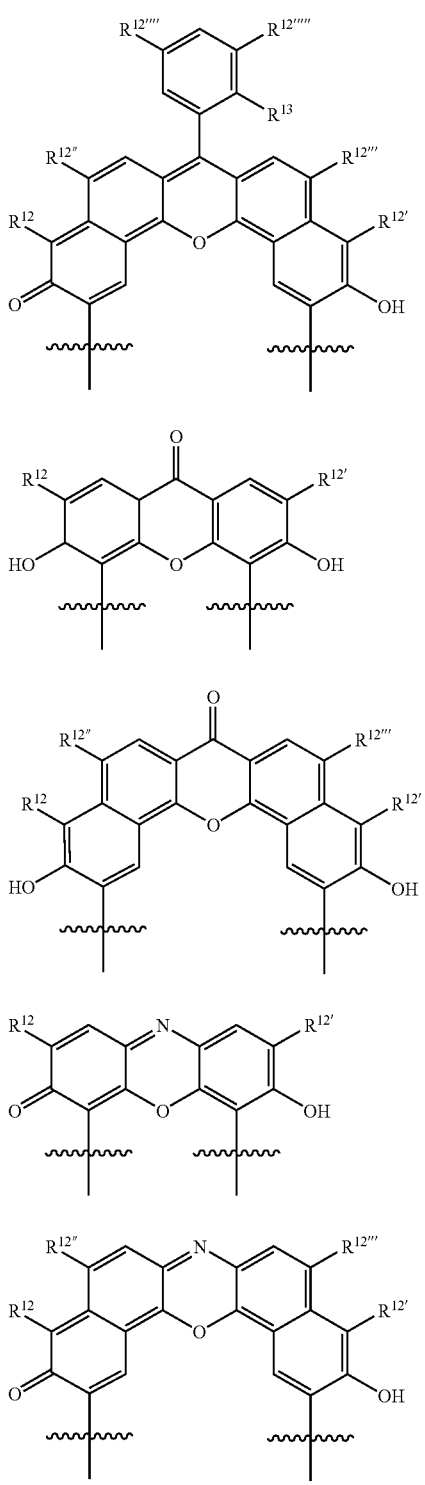

wherein $R^{12}$, $R^{12'}$, $R^{12''}$, $R^{12'''}$, $R^{12''''}$, and $R^{12'''''}$ are each independently hydrogen, halogen, hydroxyl, or alkoxyl; and $R^{13}$, when present, is hydrogen, carboxyl, carboxylate or sulfonate.

Regardless of whether cyanine, squarine, fluorescein, or other fluorochromes are used, it is desirable to select pairs of fluorochromes capable of generating a detectable energy transfer, such as fluorescence resonance energy transfer (FRET), fluorescence quenching, or excition formation. Particularly preferred pairs are capable of performing FRET. One of ordinary skill in the art will appreciate criteria necessary for selecting FRET pairs which emit frequencies in desirable ranges. See Li et al., *Bioconjugate Chem.* 10:242 and 245 (1999). Typical donor/acceptor pairs are given in Wu & Brand *Anal. Biochem.* 218, 1-13 (1994). Spectroscopic characteristics of indocyanine (Cy3, Cy3.5, Cy5, Cy7) donor/acceptor pairs are given in Bastiaens & Jovin in *Cell Biology, A Laboratory Handbook*, Celis, J. E. ed., Academic Press, Vol. 3, 136-146 (1998), both of which are herein incorporated by reference in their entireties. Preferably, the acceptor fluorescent compounds have a high quantum yield and a large extinction coefficient so that one dye can be used to detect small quantities of the target material.

Preferred Fluorescent Conjugates

Fluorescent conjugates that are small enough and permeable enough so as to be capable of traversing a biological membrane are particularly desirable. Thus, when permeating a biological membrane is important, each of the fluorescent conjugates must be able to permeate the membrane.

Modifying groups that aid in the use of the fluorescent conjugates may also be incorporated. For example, the fluorescent conjugates may be substituted at one or more positions to add a solid-phase binding group or a crosslinking group.

For applications involving labeling of target materials within living cells, the fluorescent conjugates are preferably capable of traversing a biological membrane. Smaller molecules are generally able to traverse a biological membrane better than larger derivatives. Fluorescent conjugates of less than 2000 Daltons are preferable for membrane traversal.

The polarity of the fluorescent conjugates used in the SARP can also determine the ability of the fluorescent conjugates to traverse a biological membrane. Generally, a hydrophobic fluorescent conjugate is more likely to traverse a biological membrane. The presence of polar groups can reduce the likelihood of a molecule to traverse a biological membrane. A fluorescent conjugate that is unable to traverse a biological membrane may be derivatized by addition of groups that enable or enhance the ability of the molecule to traverse a biological membrane. Preferably, such derivatization does not significantly alter the ability of the fluorescent conjugate to subsequently react with a target sequence. The fluorescent conjugate may also be derivatized transiently. In such instances, after traversing the membrane, the derivatizing group is eliminated to regenerate the original fluorescent conjugate. Examples of derivatization methods that increase membrane traversability include ether formation with acyloxyalkyl groups. Jansen, A. and Russell, T. J., *J. Chem. Soc.*, 2127-2132 (1965). Also, pivaloyl ester is useful in this regard. Madhu et al., *J. Occul. Pharmaco. Ther.*, 14:389-399 (1998).

Alternatively, when the target material is, for example, a protein bound to a cellular surface, the fluorescent conjugates may be derivitized so as to render it impermeable to a cellular membrane. One of ordinary skill will appreciate the variability of the cell permeability of the compounds of the present invention and be able to routinely adjust and test for same.

It is desirable to detect the SARP outside the normal light spectrum of biological autofluorescence. For this purpose, longer wavelength red and near infrared (NIR) fluorophores are useful. Recent developments in coupling these fluorophores, which have desirable emission spectra but unsatisfactorily low quantum yields (O) and short lifetimes have enabled their use in FRET detection schemes. Specifically, NIR fluorophores acceptors have been coupled with longer lived donors resulting in longer lived detectable emissions. These FRET pairs generate signals that possess satisfactory quantum yields as well as longer lifetime emissions. The signal to noise ratio is also reduced as a result of the longer lived acceptor emissions. Lakowicz, et al., *Analytical Biochem.*, 288:62-75 (2001). Thus, acridine orange, ethidium bromide and Ru-BD donors and nile blue A perchlorate, and TOTO-3 and TO-PRO-3 (Molecular Probes, Eugene, Oreg.) as acceptors are suitable donor acceptor pairs for use in the probes of the present invention.

Selection of fluorescent compounds useful in relay systems in which a first energy transfer is followed by a or a plurality of subsequent second energy transfer, is also within the contemplation of the inventors. This cascading technique, similar to the aforementioned NIR FRET technique, can be used to select desirable emissions wavelengths as well as optimize the parameters of quantum yields and lifetimes of the final acceptor dye.

In an advantageous aspect, one or more of the fluorescent conjugates of the SARPs are derived from one of the two general structural formulae as follows:

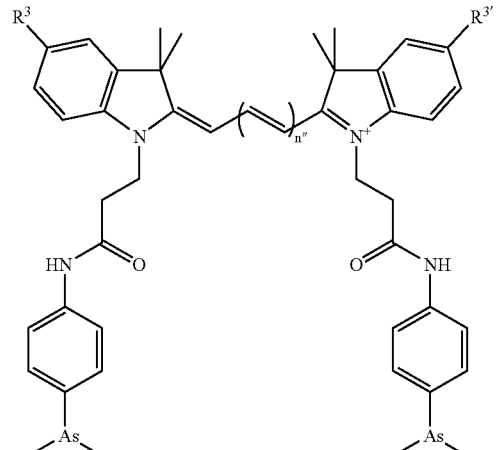

n″ = 1: Cy3-(PAO)$_2$;
n″ = 2: Cy5-(PAO)$_2$

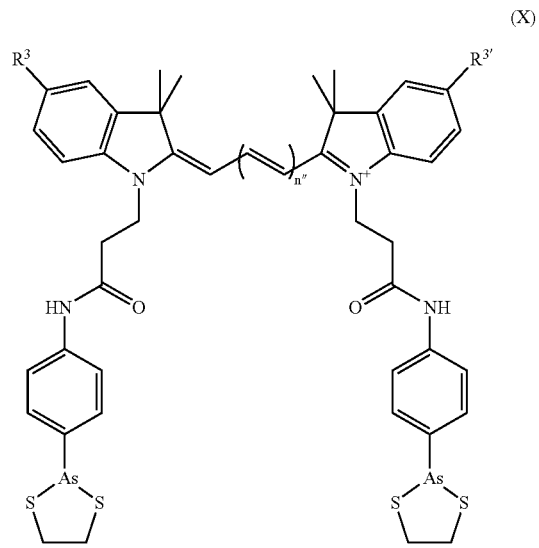

n″ = 1, R$^3$ and R$^{3'}$ = H: Cy3-(PAEDT)$_2$
n″ = 2, R$^3$ and R$^{3'}$ = H: Cy5-(PAEDT)$_2$
n″ = 1, R$^3$ and R$^{3'}$ = SO$_3^-$: sulfo-Cy3(PAEDT)$_2$
n″ = 2, R$^3$ and R$^{3'}$ = SO$_3^-$: sulfo-Cy5(PAEDT)$_2$ Another preferred fluorescent conjugate is a mono nitrilotriacetic acid chelate having the following general structural formula:

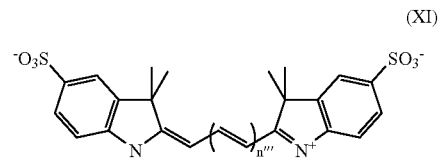

wherein: n‴ is 1 or 2, which are referred to herein as (Ni$^{2+}$:NTA)$_1$-Cy3 and (Ni$^{2+}$:NTA)$_1$-Cy5, respectively.

Yet another preferred fluorescent conjugate is a bidentate nitrilotriacetic acid (NTA) chelate having the following general structural formula:

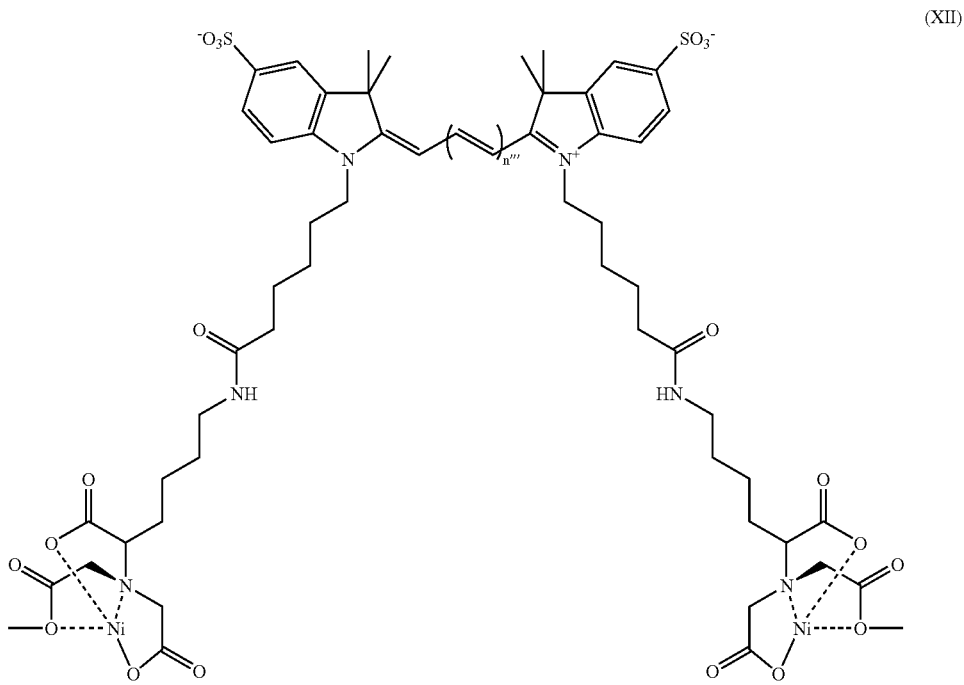

(XII)

wherein: n''' is 1 or 2, which are referred to herein referred to herein as $(Ni^{2+}:NTA)_2$-Cy3 and $(Ni^{2+}:NTA)_2$-Cy5, respectively.

It is also possible to use a molecule according to general Formula (VI) as described supra, as one of the fluorescent conjugates. A particularly advantageous compound according to Formula (VI), substituted at one or more positions of Formula (VI) with a detectable group, is a FlAsH compound, such as: 4',5'-bis(1,3,2-dithioarsolan-2-yl)fluorescein-(1,2-ethanedithiol)$_2$. This structure is referred to as FlAsH-EDT$_2$ and is shown below:

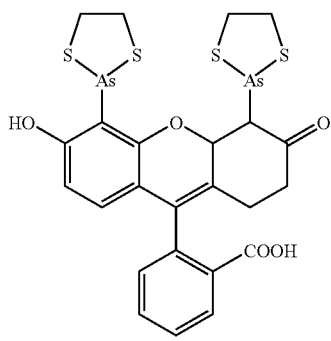

Another particularly advantageous molecule according to general Formula (VI), substituted at one or more of the positions of Formula (VI) with a detectable group, is a ReAsH compound. A suitable ReAsH compound for use with the present invention is ReAsH-EDT$_2$, which is described by Adams, et al., in J. Am. Chem. Soc. (2002) 124, 6063-6076. ReAsH has the following formula:

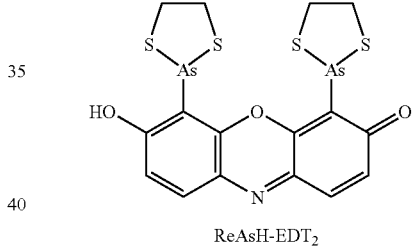

ReAsH-EDT$_2$

Peptide Containing Fluorescent Conjugates

In addition, fluorescent conjugates of the present invention may be a fluorescently labeled antibody or hapten. Details of how to make and use haptenylated probes, for example biotinylated probes are well known in the art, and are disclosed, for example, in U.S. Pat. No. 6,268,133. Alternatively, fluorescently labeled haptens are also commercially available. See, for example, B-10570 (Broton-4 fluorescein) available from Molecular Probes, Inc., Eugene, Oreg.).

Preferred Combinations of Fluorescent Conjugates

An advantage of the present invention is that it is possible to select fluorescent conjugates having improved selectivity in association with their tags than is presently available. For example, bis arsenical molecules according to general structural Formula (IB) possess greater selectivity to certain cysteine containing sequences than do the FlAsH molecules.

In particular, as will be described in further detail below, the present inventors have found that fluorescent conjugates according to general structure Formula (II) selectively associated with target sequences of the form $C(X)_iC(X)_jC(X)_kC$, wherein C is Cysteine, X is any amino acid, and i, j and k are each independently 0 or 1 to 8. In contrast, FlAsH-EDT$_2$ does not interact substantially with a tag of this form. FlAsH-EDT$_2$ possessed greater selectivity to tags of the general form C(X$_i$)C, wherein X is any amino acid, C is Cysteine and i is 0-6.

In view of the foregoing, a particularly desired combination of first and second fluorescent conjugates, respectfully, is the combination of a molecule of Formula (II) with a molecule of Formula (VI), wherein one or more positions of Formula (VI) have been substituted with a detectable group, such as fluorescein (e.g., FlAsH) or resorufin (e.g., ReAsH).

Desirable combinations of first and second fluorescent conjugates include:
  (a) Cy3-(PAEDT)$_2$ or sulfo-Cy3-(PAEDT)$_2$/Cy5-(PAEDT)$_2$ or sulfo-Cy5-(PAEDT)$_2$,
  (b) Cy3-(PAEDT)$_2$ or sulfo-Cy3-(PAEDT)$_2$/FlAsH-EDT$_2$;
  (c) Cy5-(PAEDT)$_2$ or sulfo-Cy5-(PAEDT)$_2$/FlAsH-EDT$_2$;
  (d) Cy3-(PAEDT)$_2$ or sulfo-Cy3-(PAEDT)$_2$/Cy5-(NTA:Ni$^{2+}$)$_2$;
  (e) Cy3-(PAEDT)$_2$ or sulfo-Cy3-(PAEDT)$_2$/ReAsH-EDT$_2$; and
  (f) Cy5-(PAEDT)$_2$ or sulfo-Cy5-(PAEDT)$_2$/ReAsH-EDT$_2$.

Notably, one of the fluorescent conjugates in a pair may be a known fluorescent probe which associates with less selectivity to its tag than the other fluorescent conjugate in the pair. In this case, the lack of selectivity of one conjugate in association with its tag is compensated for by having the other fluorescent conjugate associate with superior selectivity to its tag. Since detection occurs when both of the paired fluorescent conjugates successfully associate in sufficient proximity to perform FRET, then the fluorescent conjugate with greater selectivity effectively dictates when the detectable event occurs, thereby improving overall selectivity and reducing noise in detection of FRET. Furthermore, even if both fluorescent conjugates do not have high selectivity in associating with their tags, noise will still be substantially less than either conjugate used alone, because the detectable energy transfer occurs only when the conjugates are in sufficient proximity to perform FRET.

Target Materials and Target Sequences of the Invention

The target sequence or tag is an exogenous amino acid sequence tailored to the particular probe with which it is designed to bind or associate. Suitable peptide tags and the probes that will selectively associate therewith are summarized in Table I below.

The target sequences may be incorporated at any desired sites within a target material, provided that the distance between the target sequences are within sufficient proximity to allow the assembled probe to perform a detectable energy transfer. Preferably the target sequences are incorporated at a site that is: (a) accessible and (b) not essential for structure and function of the target material.

Target materials can be selected from, but are not limited to, the following: a protein, a peptide, a polypeptide, an antibody, a Lac repressor, and a protein nucleic acid (PNA).

For example, when the target material is a protein, the target sequence preferably is incorporated at the N-terminal region, at the C-terminal region, at an internal loop region, at a surface exposed non-essential loop, at an internal linker region, or at combinations thereof. The specific site, or set of sites, can be chosen to accommodate the functional requirements of a protein. For example, it is known that N-terminal modification of chemokines can affect their activity; therefore, in applications with chemokines, either C-terminal modification or internal modification would be preferable. Since labeling is performed at defined, user-selected sites, adventitious effects on the activity of labeled polypeptides can be avoided. When it is important to preserve the tagged protein's activity, specific activity testing of the tagged as compared to the untagged protein may be conducted to verify activity. See, for example, Mas et al,. *Science,* 233: 788-790 (1986).

Preferably, the distance between the target sequences will be that distance in which R$_0$ is from about 0.1 to about 2, more preferably the distance will be that distance in which R$_0$=1. Examples of possible arrangements of tags include two adjacent tags or two tags separated by a spacer. Spacers may be endogenous or exogenous residues. When the spacer includes endogenous residues they may be selected from a plurality of residues within a monomeric or oligomeric target molecule. When in oligomeric target molecules, the spacer residues may be within the same or different promoters of the oligomeric target material. In one desired embodiment, at least one of the tags is an exogenous amino acid sequence. When the spacer is an exogenous residue, it may be a flexible or rigid or assume an alpha-helix configuration or be a protein domain residue.

In preferred embodiments, the target sequence includes a first peptide tag/spacer/second peptide tag module wherein, (i) the first peptide tag is of the form C(X$_i$)C, wherein X is any amino acid, C is Cysteine and i is 0-6; (ii) the second peptide tag is of the form: C(X)$_i$C(X)$_j$C(X)$_k$C, wherein C is Cysteine, X is an amino acid, and i, j, and k are each independently 0 or an integer of from 1 to 8; and (iii) the spacer, which separates the first and second peptide tags is of the form (X)$_n$, where X is any amino acid and n is an integer from about 6 to about 26.

The SARP first tag/spacer/second tag module can be encoded by recombinant nucleic acid sequences, which can be included within a kit along with one or more other kit components. Furthermore, an isolated or recombinant nucleic acid sequence encoding (a) at least one target material; and (b) the SARP tag/spacer/tag module is provided herein, and can be included within a kit.

In one desired embodiment, the spacer is of the form (P)$_n$, where P, is Proline and n is an integer from about 6 to about 18. In another desired embodiment, the spacer is of the form A(HL)$_n$A, where HL is EAAAK (SEQ ID NO:7) and n is an integer from about 3 to about 6. Examples of suitable spacers include, but are not limited to, the following: PPPPPPPP (SEQ ID NO:27); PPPPPPPPPPPP (SEQ ID NO:28); AEAAAKEAAAKEAAAKEAAAKA (SEQ ID NO:29); and AEAAAKEAAAKEAAAKEAAAKEAAAKA (SEQ ID NO:30).

In one desired embodiment, the SARP first tag/spacer/second tag module is selected from one of the following: SEQ ID NO:31; SEQ ID NO:32; SEQ ID NO:33; SEQ ID NO:34; SEQ ID NO:35; SEQ BD NO:36; SEQ ID NO:37; and SEQ ID NO:38.

In another desired embodiment, the SARP first tag spacer/second tag module is selected from one of the following: SEQ ID NO:39; SEQ ID NO:40; SEQ ID NO:41; SEQ ID NO:42; SEQ ID NO:43; SEQ ID NO:44; SEQ ID NO:45; and SEQ ID NO:46.

Suitable target materials include, but are not limited to, polypeptides and polypeptide memetics (such as peptide nucleic acid). Preferably, the target material is a polypeptide.

As used herein, "polypeptide" refers to both short chains, commonly referred to as "peptides", "oligopeptides" or "oligomers", and to longer chains, generally referred to as "proteins". Polypeptides may contain amino acids other than the 20 gene-encoded amino acids. Polypeptides may include amino acid sequences modified either by natural processes, such as posttranslational processing, or by chemical modification techniques which are well-known in the art. Such modifications are well described in basic texts and in more detailed monographs, as well as in research literature. Thus, "polypeptide" includes peptides, oligopeptides, polypeptides and proteins, all of which terms are used interchangeably herein.

In one desired embodiment, the target material is a polypeptide and each of the tags is selected from the following: a tetra cysteine-containing sequence, an oligo histidine-containing sequence, a hapten-binding sequence, an antibody-binding sequence and a fluorochrome-binding sequence. In one embodiment, at least one of the first and second fluorescent conjugates is a bis-arsenical fluorochrome compound, which selectively associates with a tag including a tetra-cysteine-containing sequence. Examples of target sequences that can selectively associate with haptens are: anti-digoxinenin (DIG)scFV anti-biotin, streptavidin, avidin or the like, depending on the hapten selected. For example, streptavidin is known to bind tightly to biotin. In yet another embodiment, at least one of the first and second fluorescent conjugates is a fluorescently-labeled antibody, which selectively associates with a tag including an antibody-binding sequence. In still yet another embodiment, at least one of the first and second fluorescent conjugates is a transition metal fluorochrome compound, which selectively associates with a tag including an oligo histidine-containing sequence.

The target material contains, or is modified to contain at least two target sequences. Alternatively, the target material and a material to which it selectively associates, are both modified to contain a single target sequence.

The following are preferred pairs of suitable fluorescent conjugate-target sequence combinations for use in SARPs:

a. a mono-arsenical molecule according to the general structural Formula (IA), which selectively associates with a cysteine containing peptide tag of the form: CCXCC, wherein C is cysteine, X is any amino acid;

b. a bis-arsenical molecule according to the general structural Formula (IB), which selectively associates with a cysteine-containing peptide tag of the form: $C(X)_iC(X)_jC(X)_kC$ wherein C is Cysteine, X is any amino acid, and i, j, and k are each independently 0 or an integer of from 1 to 8. The following sequences are particularly desirable: CCPPPCC (SEQ ID NO:19); CCPPPPCC (SEQ ID NO: 20); CCPPPPPCC (SEQ ID NO:21); CCPPPPPPCC (SEQ ID NO: 22); CCPGPCC (SEQ ID NO:18); CCGPCC (SEQ ID NO:2); CGCGCGC SEQ ID NO: 23); and CGPCCGPC (SEQ ID NO:4). Particularly advantageous is the use of any of these tags with a bis-arsenical compound according to general structural Formula (IB) as described supra;

c. a DIG hapten with an anti-DIG, a biotin with one of an anti-biotin, a streptavidin, or an avidin;

d. a mono-transition metal molecule according to general structural Formula (VII), with a polyhistidine preferably including 3 residues (SEQ ID NO:9); and e. a bidentate transition metal molecule according to general structural Formula (VIII) with hexahistidine (SEQ ID NO:8).

In general, the transition metal molecules can bind to polyhistidine tags having from about 3 to about 10 residues. These include SEQ ID NOS: 9, 10, 11, 8, 12, 13, 14 and 15.

With respect to bis-arsenical molecules, wherein the bis-arsenical molecule is Cy3-bis-sulfonato bis-propionamido-phenylarsine or Cy3 bis-propionamido-phenylarsine, the corresponding target sequence is more preferably selected from the following: CCPPPCC (SEQ ID NO:19); CCPPPPCC (SEQ ID NO:20); CCPPPPPCC (SEQ ID NO:21); CCPPPPPPCC (SEQ ID NO:22); CCPGPCC (SEQ ID NO:18) and CCGPCC (SEQ ID NO:2).

Moreover, where the bis-arsenical molecule is Cy5-bis-sulfonato bis-propionamido-phenylarsine or Cy5 bis-propionamido-phenylarsine, the corresponding target sequence is more preferably selected from the following: CCPPPCC (SEQ ID NO:19); CCPPPPCC (SEQ ID NO:20); CCPPPPPCC (SEQ ID NO:21); CCPPPPPPCC (SEQ ID NO:22); CCPGPCC (SEQ ID NO:18); CGCGCGC (SEQ ID NO: 23) and CGPCCGPC (SEQ ID NO:4).

In one embodiment, a first fluorescent bis-arsenical includes Cy3 and the second bis-arsenical fluorescent conjugate includes Cy5. For example, in one embodiment, the first fluorescent conjugate is Cy3-bis-sulfonato bis-propionamido-phenylarsine or Cy3 bis-propionamido-phenylarsine; and the second fluorescent conjugate is Cy5-bis-sulfonato bis-propionamido-phenylarsine or Cy5 bis-propionamido-phenylarsine. In this instance, a suitable first tag is CCGPCC (SEQ ID NO:2); and a suitable second tag is of the form $CGPC(G)_j CGPC$, where C is Cysteine, G is glycine and P is Proline, and j is 0 or an integer from 1 to 8. For example, the second tag can be selected from: CGPCCGPC (SEQ ID NO:4); CGPCGCGPC (SEQ ID NO:5) and CGPCGGCGPC (SEQ ID NO:6).

In particularly desired embodiments, the first fluorescent conjugate is a conjugate represented by the general structure Formula (IB) and tautomers acids and salts thereof, and the second conjugate is a conjugate represented by Formula (VI) and tautomers anhydrides and salts thereof. In such embodiments, the first peptide tag is preferably of the form: $C(X)_iC(X)_jC(X)_kC$, wherein C is Cysteine, X is an amino acid, and i, j, and k are each independently 0 or an integer of from 1 to 8; and the second tag is preferably of the form $C(X_i)C$, wherein X is any amino acid, C is Cysteine and i is 0-6. Whereas a first fluorescent conjugate of Formula (IB) can selectively bind a first peptide tag of the form $C(X)_iC(X)_jC(X)_kC$, wherein i, j and k are each 0 or 1 to 8, the second conjugate of Formula (VI) does not interact substantively with a tag of this form. Examples of conjugates of Formula (IB) include Cy3 bis-sulfonato bis-propionamido-phenylarsine, Cy3 bis-propionamido-phenylarsine, Cy5 bis-sulfonato bis-propionamido-phenylarsine and Cy5 bis-propionamido-phenylarsine.

In one desired embodiment, a conjugate of Formula (IB) selectively associates with a tag of the form: $CC(P)_nCC$, where C is Cysteine, P is Proline, and n is an integer from 3 to 8. In another desired embodiment, a conjugate of Formula (IB) selectively associates with a tag of the form: $CGPC(G)_jCGPC$, where C is Cysteine, G is glycine, P is Proline, and j is 0 or an integer from 1 to 8.

For example, conjugates of Formula (IB) have been found by the present inventors to selectively associate with the following tetra-cysteine containing tags: CCPPPCC (SEQ ID NO:19); CCPPPPCC (SEQ ID NO:20); CCPPPPPCC (SEQ ID NO:21); CCPPPPPPCC (SEQ ID NO:22); CCPGPCC (SEQ ID NO:18); CGCGCGC (SEQ ID NO:23) and CGPCCGPC (SEQ ID NO:4).

In embodiments where the first conjugate is according to Formula (IB), and the second conjugate is according to Formula (VI), the second peptide tag is preferably of the form C(X$_i$)C, wherein X is any amino acid, C is Cysteine and i is 0-6. For example, suitable tags of this form include CCGCC (SEQ ID NO:25) and CCCC (SEQ ID NO:24).

In one embodiment of the present invention, at least one of the tags and the fluorescent conjugate that selectively associates therewith are respectively selected from the following:

| Target Sequence(s) | Fluorescent Conjugate |
|---|---|
| a. HHH (SEQ ID NO: 9) | 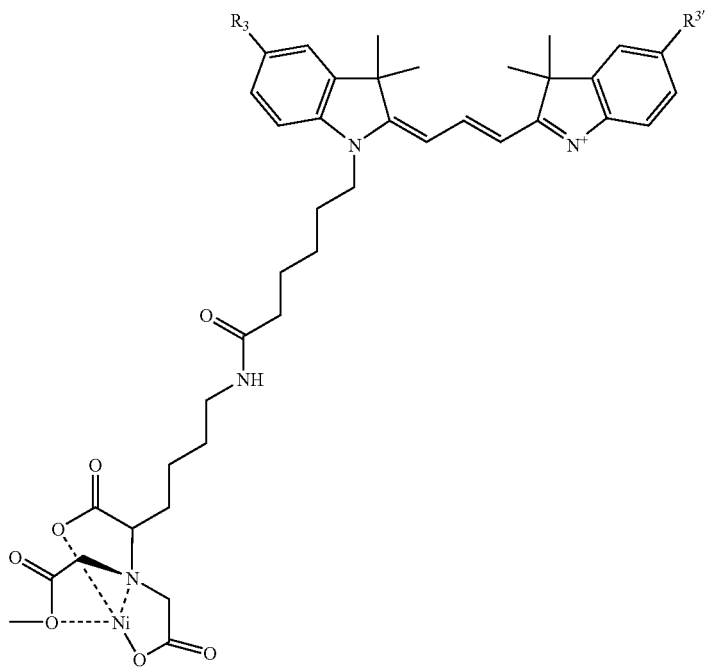 |
| b. HHHHHH (SEQ ID NO: 8) | 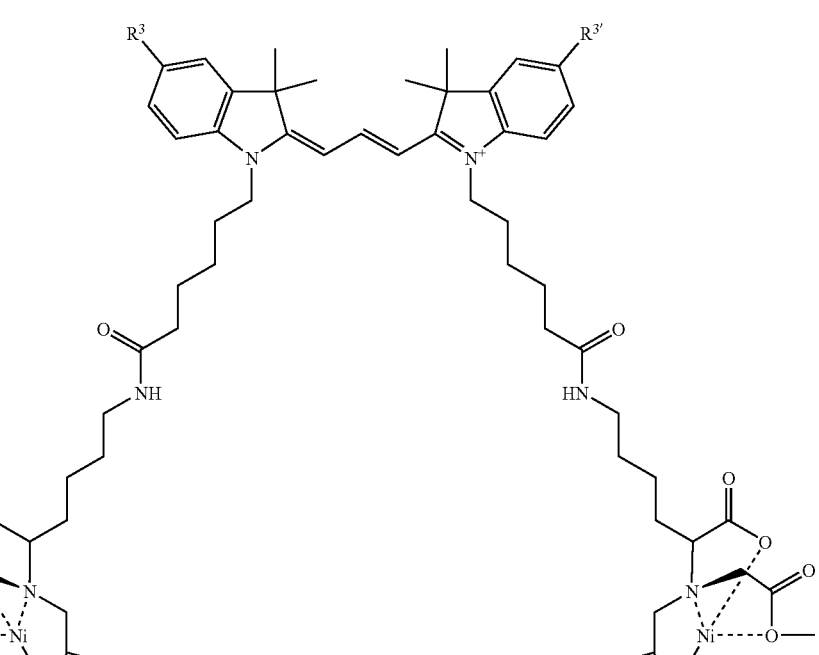 |

-continued
| Target Sequence(s) | Fluorescent Conjugate |
|---|---|
| c. CCGPCC (SEQ ID NO: 2) | 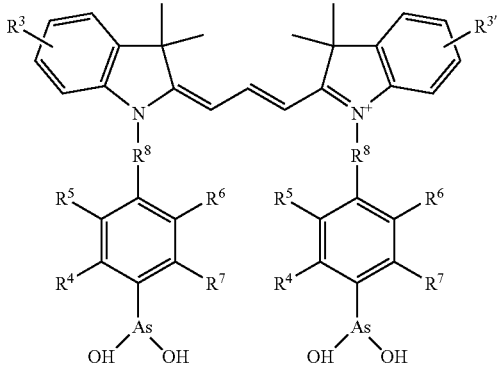 |
| d. CCPGCC (SEQ ID NO: 3) | 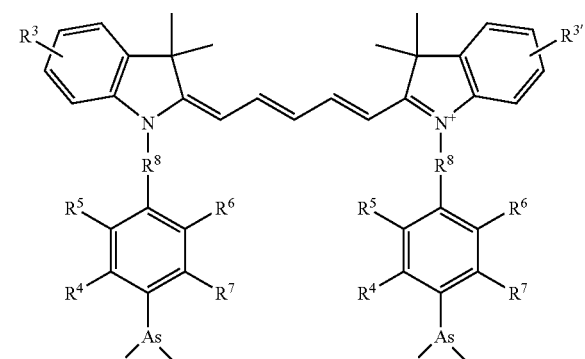 |
| e. CCGPCC (SEQ ID NO: 2); CCPPPCC (SEQ ID NO: 19); CCPPPPCC (SEQ ID NO: 20); CCPPPPPCC (SEQ ID NO: 21); CCPGPCC (SEQ ID NO: 18) | 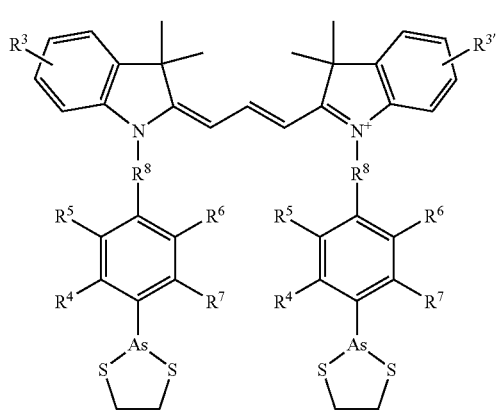 |
| f. CGPCCGPC (SEQ ID NO: 4); CGPCGCGPC (SEQ ID NO: 5); CGPCGGCGPC (SEQ ID NO: 6); CCPPPCC (SEQ ID NO: 19); CCPPPPCC (SEQ ID NO: 21); CCPPPPPCC (SEQ ID NO: 22); CCPPPPPPCC (SEQ ID NO: 22); CCPGPCC (SEQ ID NO: 18); CGCGCGC (SEQ ID NO: 23) | 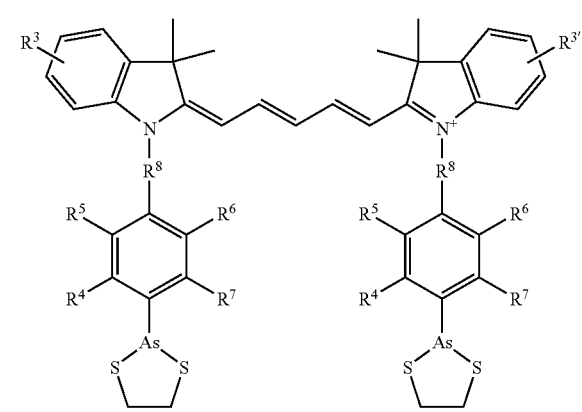 |

-continued

| Target Sequence(s) | Fluorescent Conjugate |
|---|---|
| g. CCCC (SEQ ID NO: 27); CCGCC (SEQ ID NO: 28) | 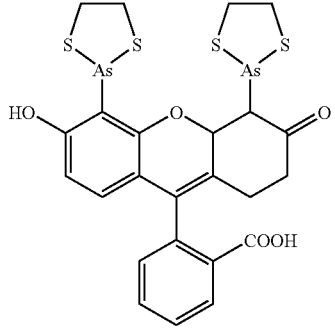 | wherein $R^4$, $R^5$, $R^6$ and $R^7$ are each independently H, F, $OR^c$, $R^c$, OAc, $NR^c$, $NH_2$, or $N(C_1-C_4 alkyl)_2$; $R^c$ is H, CH(OH)CH$_2$OH, or $(CH_2)_q$—Y, wherein q is 1-4 and Y is H, OH, NH$_2$, SH, COOH, OAc, CONH$_2$, or CN; $R^8$ is a linear or branched optionally substituted spacer from about 3 angstroms (Å) to about 15 Å long; and $R^3$ and $R^{3'}$ are each independently H or sulfonate.

Figure 4:
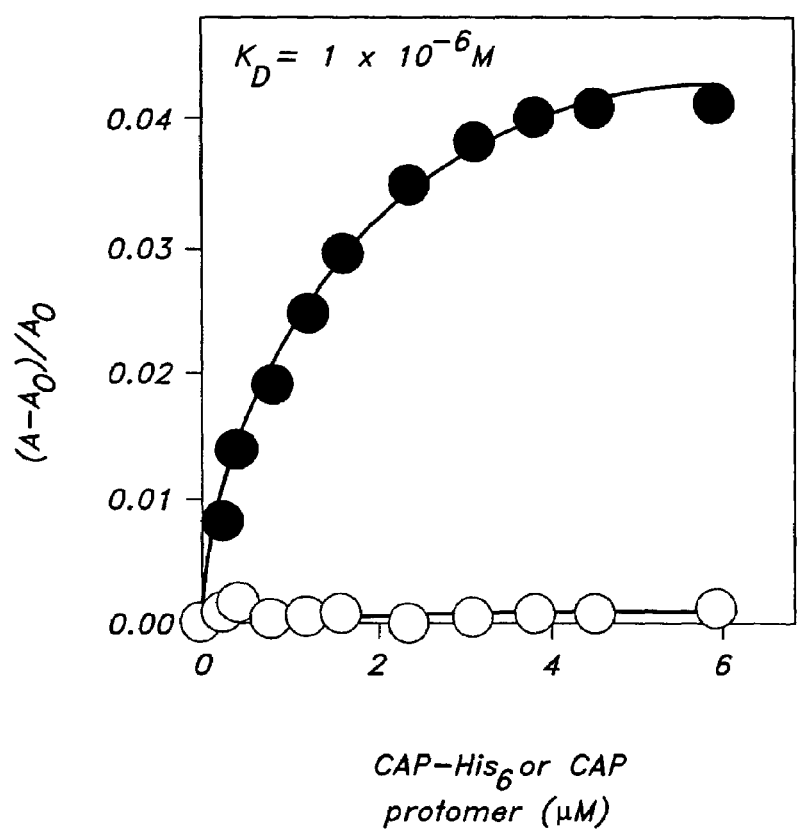
Figure 5:
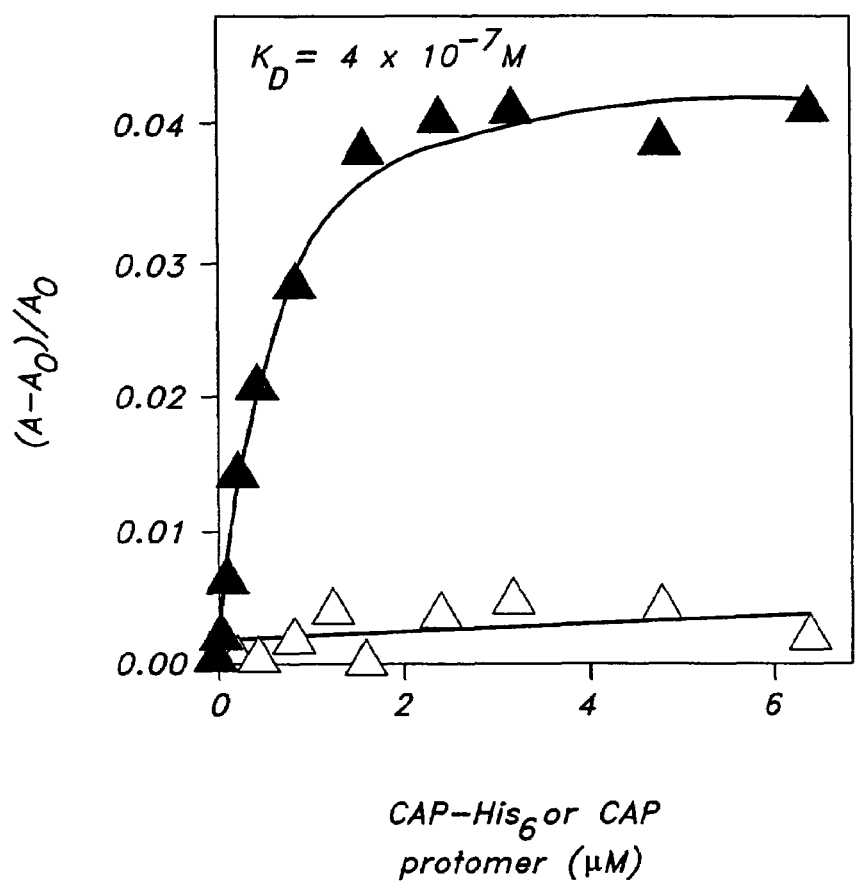
Figure 6:
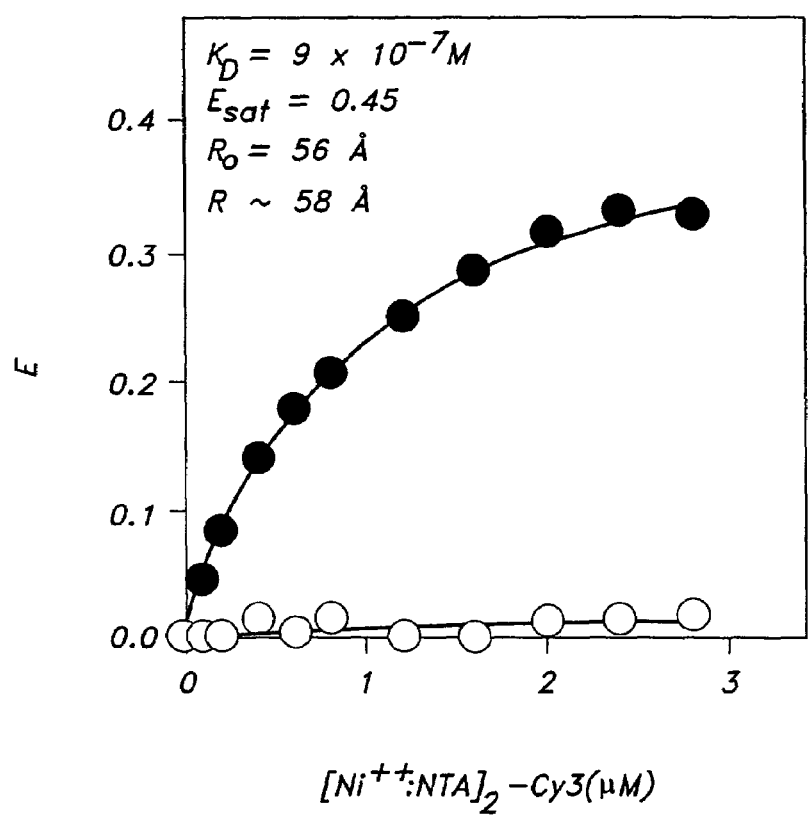
FIGS. 6 and 7 show results of FRET experiments verifying high-affinity, specific interactions of bis-transition-metal containing fluorescent conjugates according to the invention with hexahistidine-tagged protein.
Figure 7:
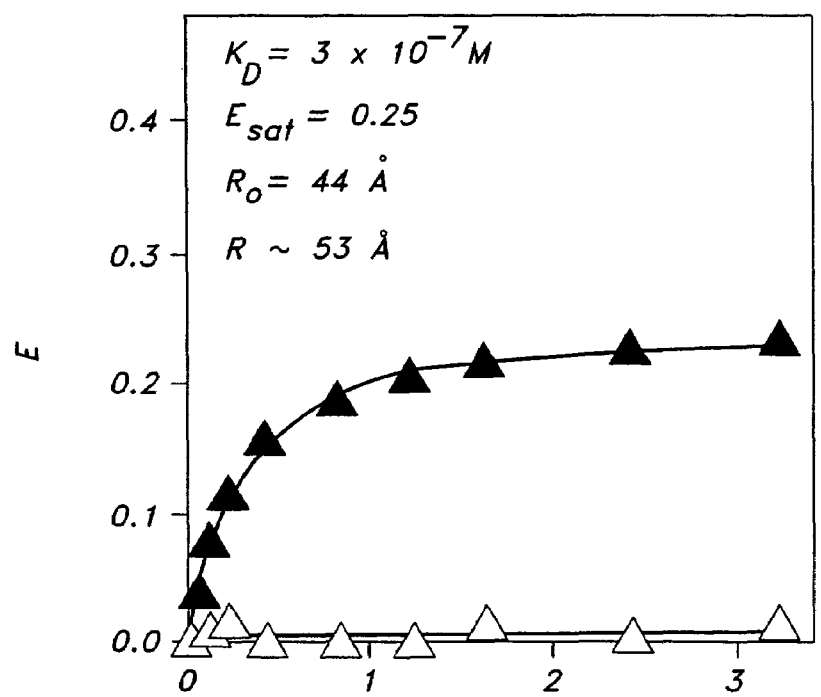
Figure 8:
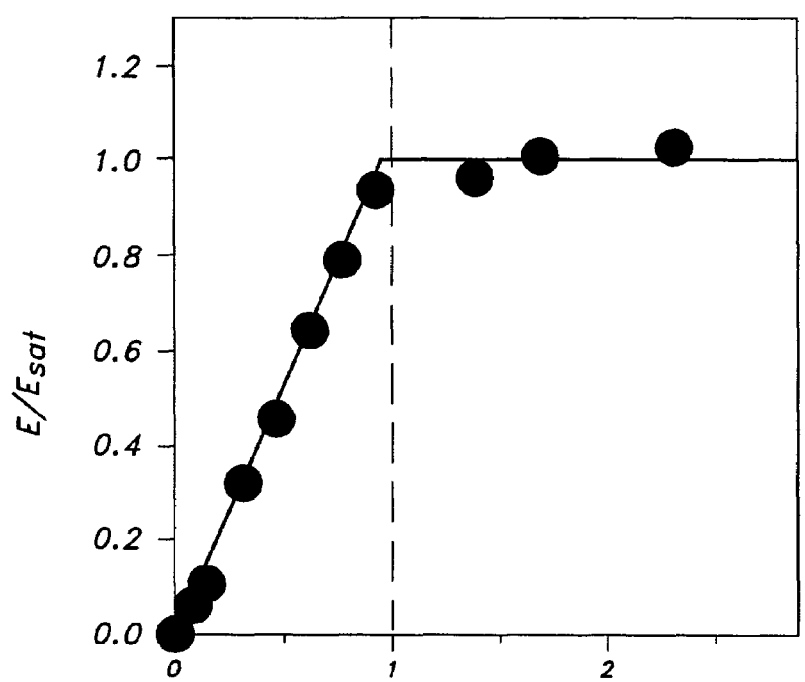
FIGS. 8 and 9 show results of FRET experiments verifying stoichiometric interactions of nickel containing fluorescent conjugates according to the present invention with a hexahistidine tag.
Figure 9:
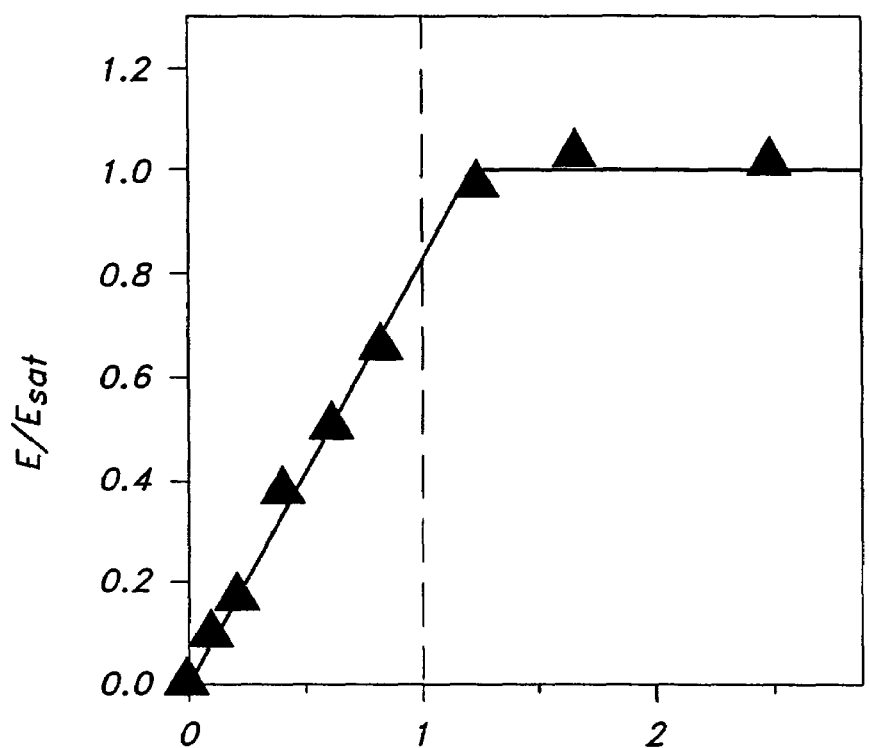

FIGS. 4 and 5 show results of fluorescence anisotropy experiments verifying specific interactions between certain bidentate transition metal containing fluorescent conjugates with hexahistidine-tagged proteins. FIGS. 6 and 7 show results of FRET based experiments verifying high-affinity specific interactions of bidentate metal containing fluorescent conjugates according to the invention with hexahistidine-tagged protein. FIGS. 8 and 9 show results of FRET based experiments verifying stoichiometric interactions of bidentate metal containing fluorescent conjugates with a hexahistidine-tagged protein.

Target-sequence-containing polypeptides may be generated by total synthesis, partial synthesis, in vitro translation, or in vivo bacterial, archaeal, or eukaryotic expression production.

In one embodiment, the target sequences and/or target-sequence-containing polypeptides used in the invention are prepared using solid-phase synthesis (see, e.g., Merrifield et al. *J. Am. Chem. Soc.,* 85:2149, (1962) Steward and Young, *Solid Phase Peptides Synthesis,* Freeman, San Francisco, (1969), and Chan and White, *Fmoc Solid Phase Peptide Synthesis—A Practical Approach,* Oxford Press (2000)).

In a preferred embodiment, the target-sequence-containing polypeptides used in the invention are prepared using native chemical ligation (Dawson et al., *Science,* 266, 1994).

In another preferred embodiment, the target sequences and/or target-sequence-containing polypeptides are generated by in vivo bacterial, archaeal, or eukaryotic expression of a recombinant nucleic acid sequence encoding the target-sequence-containing polypeptide. Methods for the construction of recombinant nucleic acid sequences encoding a tag-containing polypeptide are well known in the art (Sambrook and Russel, *Molecular Cloning A Laboratory Manual,* 3$^{rd}$ Ed., Cold Spring Harbor Laboratory, New York (2001), the entirety of which is herein incorporated by reference. In addition, techniques for transient or stable introduction of recombinant nucleic acid sequences into cells (see, for example, Ausubel et al., *Current Protocols In Molecular Biology,* John Wiley & Sons, Inc. (1995)), for replacement of native nucleic acid sequences by recombinant nucleic acid sequences in cells (see, for example, Ausubel et al., *Current Protocols In Molecular Biology,* John Wiley & Sons, Inc. (1995)), and for expression of recombinant nucleic acid sequences in cells (see e.g., Lee and Arthans, H. J. *Biol. Chem.,* 263:3521, (1988); Rosenberg, et al., *Gene,* 56:125 (1987)), are well known in the art.

SARP Assembly

Labeling of a target material is accomplished by contacting fluorescent conjugates of the invention with a target-sequence-containing target material. The fluorescent conjugates may be contacted with a target-sequence-containing target material located in, for example, a test tube, a microtiter-plate well, a cuvette, a flow cell, or a capillary, or immobilized on, for example, a surface or other solid support. Alternatively, the fluorescent conjugates may be contacted with a target-sequence-containing target material located within a cell, tissue, organ, or organism. In this embodiment, the fluorescent conjugates are preferably capable of traversing an intact biological membrane. Binding of the fluorescent conjugates to their associated tags results in assembly of the SARP. The resulting labeled target-sequence-containing target material may be readily used in a variety of applications.

In one preferred embodiment, the fluorescent conjugates of the invention are used to label target-sequence-containing molecules within cells. The fluorescent conjugates of the invention may be introduced into cells by diffusion (for fluorescent conjugates of the invention capable of traversing biological membranes) or by microinjection, electroporation, or vesicle fusion (for any fluorescent conjugates of the invention). The target-sequence-containing molecules may be introduced into cells by microinjection, electroporation, or vesicle fusion, or by expression of recombinant genes in situ.

In another preferred embodiment, a target-sequence-containing protein produced by expression of a recombinant gene within cells is labeled with a SARP of this invention by incubating cells in medium containing the fluorescent conjugates. Following labeling, and optionally following further manipulations, the cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

Preferably, the target sequences are different. Preferably, the tags are different and the first fluorescent conjugate will have selectivity for a first tag while being relatively non-specific for the second tag and other biological constituents. Also, the second fluorescent conjugate will have selectivity for a second tag while being relatively non-specific to the first tag and other material. In this case, the FRET signal will be directly related to the presence and amount of the target material of interest.

Advantageously, attachment of the fluorescent conjugates to the tagged target material can be made reversible by addition of an appropriate buffer. For the transition metal containing conjugates, it is possible to add an excess of nitrilotriacetic acid (NTA). In the case of the bisarsenical molecules, it is possible to add an excess of 1,2-ethanedithiol (EDT) to the sample to release the fluorescent conjugates from the tags.

Preferably, the SARPs of the present invention may be used under normal physiological conditions, and will not require conditions such as low pH or the like to perform the energy transfer function. The fluorescent conjugates including bis arsenical binding groups are particularly useful in this regard.

Table I below summarizes suitable fluorescent conjugates and the corresponding tags to which they selectively bind.

TABLE I

Fluorescent Conjugates and Tags to which they Selectively Bind

| Fluorescent Conjugates | Preferred Conjugates | Tags | Preferred Tags |
|---|---|---|---|
| FlAsH[1] | (4',5'-bis(1,3,2-dithioarsolan-2-yl)fluorescein-(1,2-ethanedithiol)$_2$ | C(X$_i$)C, wherein X is any amino acid, C is Cysteine and i is 0-6 | SEQ ID NO:24<br>SEQ ID NO:25 |
| Bis-phenylarsine Molecules[2] | Cy3-(PAEDT)$_2$ or sulfo-Cy3-(PAEDT)$_2$ | C(X)$_i$C(X)$_j$C(X)$_k$C, wherein X is any amino acid and i, j, and k are each independently 0 to 8. | SEQ ID NO:1 CCXXCC<br>SEQ ID NO:2 CCGPCC<br>SEQ ID NO:3 CCPGCC<br>SEQ ID NO:16 CCXXXCC<br>SEQ ID NO:17 CCGPCCC<br>SEQ ID NO:18 CCPGPCC<br>SEQ ID NO:26 CCPPCC<br>SEQ ID NO:19 CCPPPCC<br>SEQ ID NO:20 CCPPPPCC<br>SEQ ID NO:21 CCPPPPPCC<br>SEQ ID NO:22 CCPPPPPPCC |
| Transition metal molecules | Ni$^{2+}$:nitrilotriacetic acid (Ni$^{2+}$:NTA)$_2$ | His$_{3-10}$ | SEQ ID NO:8 HHHHHH (His$_6$) |
| Bis-phenylarsine Molecules[2] | Cy5-(PAEDT)$_2$ or sulfo-Cy5-(PAEDT)$_2$ | C(X)$_i$C(X)$_j$C(X)$_k$C, wherein X is any amino acid and i, j, and k are each independently 0 to 8. | SEQ ID NO:4 CGPCCGPC<br>SEQ ID NO:5 CGPCGCGPC<br>SEQ ID NO:6 CGPCGGCGPC<br>SEQ ID NO:26 CCPPCC<br>SEQ ID NO:19 CCPPPCC<br>SEQ ID NO:20 CCPPPPCC<br>SEQ ID NO:21 CCPPPPPCC<br>SEQ ID NO:22 CCPPPPPPCC<br>SEQ ID NO:18 CCPGPCC<br>SEQ ID NO:23 CGCGCGC |
| Haptens[3] | Biotin-Cy3<br>DIG-Cy3 | Anti-biotin scFv<br>Streptavidin<br>Avidin derivative | Biotin<br>Anti-biotin scFv (Roche)<br>Streptavidin, Avidin derivative |
| Digoxigenin (DIG)[4] | DIG | Anti-digoxigenin scFv | Anti-digoxigenin scFv[5] |
| Oligoprimers[5] | M13 universal forward sequencing primer | 5'-GTTTTCCCAGTCACGACG-3' | 5'-GTTTTCCCAGTCACGACG-3' |

TABLE I-continued

Fluorescent Conjugates and Tags to which they Selectively Bind

| Fluorescent Conjugates | Preferred Conjugates | Tags | Preferred Tags |
|---|---|---|---|
| ReAsH[6] | ReAsH-EDT$_2$ | C(X$_i$)C, wherein X is any amino acid, C is cysteine and i is 0-6 | SEQ ID NO:24 |

[1]See U.S. Pat. Nos. 6,008,378 and 6,451,569B1 to Tsien et al, for FlAsH molecules, the entirety of each of which is hereby incorporated by reference; P3004 (FlAsH) from PanVera, Madison, WI.
[2]See U.S. Patent Application entitled "Reagents And Procedures for High Specificity Labeling" by Dr. Ebright et al., filed on Jun. 14, 2002, Serial No. 60/388,699 under attorney Docket No. 744-34P or U.S. Application No. 10/461,224, filed Jun. 13, 2003 and published on Jan. 29, 2004 under Publication No. US2004/0019104A. These are each hereby incorporated in their entirety, for disclosure of suitable bis-arsenical compounds.
[3]See Handbook of Fluorescent Probes and Research Products, Eighth Edition (May 2001), Molecular Probes, Inc., Eugene, OR, the entirety of which is herein incorporated by reference. See also, B-10570 Biotin 4-fluorescein available from Molecular Probes, Inc., Eugene, OR; A-11243 mouse monoclonal 2F5 antibody to biotin, S-888 streptavidin, A-887 avidin, available from Hoffmann-La Roche Ltd, Diagnostics Division, Roche Molecular Biologicals, Basel, Switzerland. See also reagents and procedures available from Light Cycler System, Roche Diagnostics Corporation, Roche Applied Science, and Amersham. See also, U.S. Pat. No. 6,268,133 for disclosure of suitable hapten/streptavidin compounds. See also, Roche website: http://biochem.roche.com.
[4]See, for example, B-23460, BODIPY FL DIG from Molecular Probes, Inc. Eugene, OR.
[5]Jingyue, et al., Proc. Natl. Acad. Sci. USA, 92:4347-4351(1995). See article for design of four FRET pair labeled primers labeled with four different FRET pairs for use in performing multiplex four color sequencing of DNA for determination of nucleic acid base sequences.
[6]See Adams, et al. (2002) J. Am. Chem. Soc. 124, 6063-6076. ReAsH is available from Pan Vera, Madison, WI.

As seen above in Table I, choice of desirable target sequences depends on the particular fluorescent conjugate to which they are intended to associate or bind. For bis arsenical molecules, although certain preferred tags have been disclosed, one of ordinary skill may use alternative tags to which particular arsenical compounds will selectively associate. Methods for identifying such tags are included in U.S. Patent Application entitled "Reagents And Procedures for High Specificity Labeling" by Dr. Ebright et al., Ser. No. 60/388,699, filed on Jun. 14, 2002, under attorney docket no. 744-34P; and *Nature*, 354:82 (1991); and *Meth. Enzymol.* 267:211 (1996), the entireties of which are herein incorporated by reference.

Use of the Inventive Probes

It is contemplated that the fluorescent conjugates of the invention may be used in a variety of in vitro and in vivo applications. Such applications can be readily adapted for high-throughput screening, using formats, equipment, and procedures apparent to persons skilled in the art. These applications find use in many areas of biology and biological research including drug screening, diagnostics, and academic research.

The SARPs of the invention may be used in numerous standard assay formats, as are well known in the art. For example, in one embodiment, the assay is selected from the group consisting of an immunoassay, a DNA-protein binding assay, a protein-protein assay, a protein conformational assay, an enzyme assay, and rate studies thereof. Some examples of assay formats include fluorescence emission intensity, fluorescence polarization (FP), fluorescence anisotropy (FA), fluorescence resonance energy transfer (FRET), fluorescence correlation spectroscopy (FCS), fluorescence-activated cell—or particle—sorting (FACS), x/y-fluorescence scanning (FluorImaging), epi-illumination optical microscopy, confocal optical microscopy, total-internal-reflection optical microscopy, absorbance spectroscopy, enzyme-linked immunosorbent assay (ELISA) and assays formats that involve use of biotin or other hapten incorporation to provide a recognition event for binding or immobilization of one or more components.

Some examples, which are intended to be illustrative and not limiting of possible assay formats and applications that could use SARPs according to the invention to label target materials, are set forth below.

FRET Assays, Generally

As discussed previously, Fluorescence resonance energy transfer (FRET) is a physical phenomenon that permits measurement of molecular distances. Specifically, FRET experiments performed under conditions where the Förster parameter ($R_o$) is constant, measured changes in efficiency of energy transfer (E) permit detection of changes in distance (R). If FRET experiments are performed under conditions where the Förster parameter ($R_o$) is constant and known, the measured absolute magnitude of E permits determination of the absolute magnitude of R.

With fluorochromes and chromophores known in the art, FRET is useful over distances of about 0.1 nm to about 0.15 nm, which are comparable to the dimensions of biological macromolecules. Thus, FRET is a useful technique for investigating a variety of biological phenomena that produce changes in molecular proximity. When FRET is used as a detection mechanism, colocalization of proteins and other molecules can be imaged with spatial resolution beyond the limits of conventional optical microscopy.

Imaging assays using FRET are useful for such varied applications as detection of Hapten-IgE in single cells, MHC II-peptides, MHC I associations, epitope mapping, peptides association in membranes, lipid order in vesicles, membrane organization, lipid distribution, protein folding kinetics, transport systems, in vivo protein-protein interactions, protein subunit exchanges, DNA-protein interactions, tRNA-ribosomes, DNA triple helixes, and nucleic acid hybridization.

In general, the SARPs of the present invention may be used to detect and/or quantify a target material of interest containing, or derivatized to contain, at least two target sequences, as shown in FIG. 1A The target-sequence-containing target material is incubated with fluorescent conjugates of the invention for a time period sufficient to allow labeling of the target material. FRET from the SARP is detected, thereby detecting the target material. The target material may be detected in any material, including, but not limited to, cuvettes, microtiter plates, capillaries, flow cells, test tubes, gels, blots, and biological samples.

For example, the present invention provides a method of detecting a target material in a sample that includes the step of: tagging the target material with at least a first peptide tag and a second peptide tag, which is at a distance of about 0.1 $R_0$ to about 2 times $R_0$ from the first peptide tag to form a tagged target material. The method further includes exposing the sample to a first fluorescent conjugate including a first fluorochrome, the first conjugate being capable of selectively associating with the first peptide tag; and exposing the sample to a second fluorescent conjugate including a second fluorochrome having a distinct excitation and emission maxima from the first fluorochrome, the second conjugate being capable of selectively associating with the second peptide tag. The method also includes allowing the first and second fluorescent conjugates to associate with the tagged target material, wherein the first and second fluorescent conjugates independently assemble on the target material by associating with the first and second peptide tags, respectively, so as to form a self assembled relay probe (SARP), such that upon excitation of the first fluorescent conjugate, fluorescence energy transfer results in excitation of the second fluorescent conjugate. Finally, the method includes exposing the sample containing the SARP to light of a suitable wavelength for the excitation of the first fluorescent conjugate to occur; and detecting the energy transfer.

Suitable target materials, tags, spacers and fluorescent conjugates for use in the methods of the present invention are the same as those described above. For example, combinations of first and second conjugates, the tags to which they can selectively bind, and some preferred SARP first tag/spacer/second tag modules for use in the methods of this invention are described above.

With fluorochromes and chromophores as described infra, FRET is useful over distances of about 1 nm to about 15 nm, which are comparable to the dimensions of biological macromolecules and macromolecule complexes. Thus, FRET is a useful technique for investigating a variety of biological phenomena that produce changes in molecular proximity. When FRET is used as a detection mechanism, colocalization of proteins and other molecules can be imaged with spatial resolution beyond the limits of conventional optical microscopy.

A FRET assay can be used to monitor a reaction between analytes. For example, a method of the present invention includes: providing a first analyte in a sample, the first analyte having bound thereto at least a first and second peptide tag, wherein a distance between the tags is from about 0.1 to about 2 times $R_0$; and exposing the sample to a first fluorescent conjugate which selectively associates with the first tag. The method also includes allowing the first analyte to react with a second analyte labeled with a second fluorescent conjugate which selectively associates with the second tag, wherein the second conjugate is capable of participating in fluorescence energy transfer with the first fluorescent conjugate. Further included in the method are the steps of: exposing the sample to light of a suitable wavelength to allow the energy transfer to occur between the fluorescent conjugates; and monitoring the reaction between the analytes by monitoring a detectable signal generated as a result of the energy transfer between the fluorescent conjugates. The monitoring step can be at least one of a steady state florescence energy transfer measurement, a time resolved florescence anisotropy measurement, and a time resolved fluorescence lifetime measurement.

The reaction can be, for example, a protein folding event, a cleavage event, a protein self-association event, or rates thereof. The method can be an immunoassay, a DNA-protein binding assay, a protein-protein assay, a protein conformational assay, an enzyme assay, and rate studies thereof.

In preferred embodiments of the methods of this invention, the first tag and the first fluorescent conjugate, respectively, are selected from the following: (a) SEQ ID NO: 8/Cy5-(NTA:$Ni^{2+}$)$_2$; (b) SEQ ID NO: 2 or 18 or 19 or 20 or 21 or 22/Cy3 bis-sulfonato bis -propionamido-phenylsrsine or Cy3 bis-propionamido-phenylarsine; and (c) SEQ ID NO:4 or 5 or 6 or 18 or 19 or 20 or 21 or 22 or 23/Cy5 bis-sulfonato bis-propionamido-phenylarsine or Cy5bis-propionamido-phenylarsine. In other preferred embodiments of the methods of this invention, the second tag and the second fluorescent conjugate, respectively, are SEQ ID NO: 24 or 25/FlAsH-$EDT_2$ (4',5'-bis(1,3,2-dithioarsolan-2-yl)fluorescein-(1,2-ethanedithiol)$_2$.

A FRET assay can be used to detect and quantify binding between two molecules, molecule 1 and molecule 2. Molecule 1 can be an analyte containing at least two tags. The FRET assay may be configured as follows: A reaction mixture is prepared by combining: molecule 1 labeled with the first fluorescent conjugate of a SARP with molecule 2 labeled with a second fluorescent conjugate of the SARP. The first conjugate selectively associates with one of the tags and the second conjugate selectively associates with the other of the tags. The conjugates are able to participate in FRET. Complex formation results in self assembly of the SARP, and, correspondingly, in increased FRET. The progress of the reaction is monitored by observing the increase in FRET. Equilibrium association and dissociation constants may be extracted from the concentration-dependence of the reaction.

The invention also provides an assay method for monitoring a binding process. In this method, a first component of a specific reaction pair containing at least two peptide tags is labeled with a first conjugate and is reacted with a second component of the pair labeled with a second conjugate. The reaction can be monitored by monitoring a FRET energy transfer event. Examples of specific reaction pairs include, but are not restricted to, antibodies/antigens, hormone/receptor, enzyme/substrate, and protein/analyte.

A FRET assay to detect and quantify proteolytic activity may be configured as follows: A reaction mixture is prepared by combining a) a substrate molecule labeled at site 1 with a first fluorescent conjugate of a SARP and labeled at site 2 with a second fluorescent conjugate of SARP, wherein sites 1 and 2 are on opposite sides of the proteolytic-cleavage site, and wherein the conjugates are able to participate in FRET, and b) a sample containing a proteolytic enzyme. Cleavage of the substrate molecule by the proteolytic enzyme results in decreased proximity the conjugates, and, correspondingly, in decreased FRET. The progress of the reaction is monitored by observing the decrease in FRET.

A FRET assay to detect conformation change within molecule 1 induced upon interaction with molecule 2, may be configured as follows: A reaction mixture is prepared by combining (a) molecule 1 labeled at one site (X) with a first fluorescent conjugate of a SARP and labeled at another site (Y) with a second conjugate of the SARP, wherein the conjugates are able to participate in FRET, and (b) molecule 2. Conformation change within molecule 1 induced upon interaction with molecule 2 results in a change in proximity between X and Y, and, correspondingly, a change in FRET. The progress of the reaction is monitored by observing the change in FRET.

If the SARP is being used to detect a conformational change in a protein, a third tag and fluorescent conjugate may be used. In this case, the SARP is situated on the protein so as to generate a first signal in a first conformation. The third tag and a third fluorescent conjugate is arranged on the protein so as to be too distant to relay energy with the SARP in the first conformation but able to relay energy with one the fluorescent conjugates of the pair when the protein is in a second conformation. The conformational charge is detected by measuring a signal generated by the relay event.

Conformational changes detectable using these methods include a protein binding event, a protein folding event, a cleavage event, or a protein self-association event.

A FRET assay to measure the distance between two sites, 1 and 2, within a molecule of interest, may be configured as follows: the molecule of interest is labeled at site 1 with a first conjugate of a SARP and is labeled at site 2 with a second conjugate of the SARP, wherein the conjugates are able to participate in FRET; fluorescence excitation and emission spectra are collected for the assembled SARP; and the distance, R, is calculated as described supra.

Equilibrium association and dissociation constants may be extracted from the concentration-dependence of the reaction in the aforementioned assays.

Fluorescence Polarization or Fluorescence Anisotropy Assays, Generally

In a fluorescence-polarization (FP) or fluorescence-anisotropy (FA) assay, a sample is exposed to polarized light of a first wavelength (able to be absorbed by a fluorescent moiety), and fluorescence-emission polarization or anisotropy is monitored at a second wavelength (emitted by said fluorescent moiety). Fluorescence-emission polarization or anisotropy is inversely related to the rotational dynamics, and thus to the size, of said fluorescent moiety (or, if said fluorescent moiety is attached to a molecule or complex, to the rotational dynamics, and thus to the size, of the molecule or complex). FP or FA assays permit detection of reactions that result in changes in size of molecules or complexes, including especially, macromolecule-association and macromolecule-dissociation reactions.

An FP or FA assay to detect and quantify binding between two molecules, molecule 1 and molecule 2, may be configured as follows: A reaction mixture is prepared by combining molecule 1 labeled with a SARP according to the current invention and molecule 2. Complex formation results in formation of a higher-molecular-weight, higher-FP, higher-FA species. The progress of the reaction is monitored by observing the decrease in FP or FA. Equilibrium association and dissociation constants are extracted from the concentration-dependence of the reaction.

A further FP or FA assay may be used to detect and quantify proteolytic activity and may be configured as follows: A reaction mixture is prepared by combining a substrate molecule labeled with a SARP according to the present invention and a sample containing a proteolytic enzyme. Cleavage of the substrate molecule by the proteolytic enzyme results in the production of lower-molecular-weight, lower-FP, lower-FA fragments. The progress of the reaction is monitored by observing the decrease in FP or FA.

Fluorescence emission intensity, lifetime, polarization, anisotropy and FRET are further described in the following references: Brand, L. and Johnson, M. L., Eds., *Fluorescence Spectroscopy* (Methods in Enzymology, Volume 278), Academic Press (1997), Cantor, C. R. and Schimmel, P. R., *Biophysical Chemistry Part 2*, W. H. Freeman (1980) pp. 433-465. Dewey, T. G., Ed., *Biophysical and Biochemical Aspects of Fluorescence Spectroscopy*, Plenum Publishing (1991). Guilbault, G. G., Ed., *Practical Fluorescence, Second Edition*, Marcel Dekker (1990). Lakowicz, J. R., Ed., *Topics in Fluorescence Spectroscopy: Techniques* (Volume 1, 1991); *Principles* (Volume 2, 1991); *Biochemical Applications* (Volume 3, 1992); *Probe Design and Chemical Sensing* (Volume 4, 1994); *Nonlinear and Two-Photon Induced Fluorescence* (Volume 5, 1997); *Protein Fluorescence* (Volume 6, 2000), Plenum Publishing.

Time Dependent Analyses

The progress of the reactions of the aforementioned assays may be monitored by observing the change in fluorescence emission intensity of the SARP over time. It is also possible to detect the orientation of FRET pairs over time. For example, steady state and time resolved studies can be used to monitor equilibrium unfolding of proteins. See Lillo, M. et al., *Biochemistry*, 36:11261-11272 (1997). Time-Resolved Emission Spectroscopy uses an emission spectrum in a user-selectable wavelength range with the intensity being measured at a defined time after the excitation pulse. By running a series of spectra with varying measurement times, a time profile of the system can be constructed. Time-Resolved Emission Spectra can quickly reveal complexities in a sample. For example, a mixture of two SARPs with different lifetimes will exhibit a distinct difference in the Time-Resolved Emission Spectrum as the measurement time is varied.

The presence of excited state reactions and charge transfer complexes, for example, can be discerned using Time-Resolved Emission Spectra. Furthermore, time-resolved detection systems can be used to minimize interfering sample autofluorescence. By assembly of long lifetime low Q probe fluorescent compounds with short lifetime high Q probe fluorescent compounds, a long lifetime high Q SARP, can be formed which will emit in the NIR range and therefore be discernible from the autofluorescence.

Available instrumentation includes the StrobeMaster and the LaserStrobe (Photon Technology International, South Brunswick, N.J.). The time window for the fluorescence intensity measurement is fixed. An intensity measurement is made at each wavelength as the emission monochromator is stepped through the specified wavelength range. Changes in spectra collected at different time windows reflect processes taking place in the excited state. In this way, changes in conformation over time may be determined. It is also possible to combine anisotropy and time resolved measurements to obtain more detailed information regarding conformational changes and the like.

In Vitro, In Vivo, and Single Cell Assays

Fluorescence imaging using the aforementioned assays permits characterization of the quantities, locations, and interactions of fluorochrome-labeled target materials within living cells.

The SARPs of the present invention can be used, in vitro or in vivo, in single-molecule fluorescence assays with single-molecule detection, wherein fluorescence emission intensity, fluorescence correlation, FP/FA, or FRET is analyzed from individual single molecules. Edman et al., *Proc. Natl. Acad. Sci. USA,* 93:6710 (1996).

Assays using the SARP of the present invention can be used in flow cytometry or fluorescence activated cell sorting (FACS). This is a process in which measurements of physical and/or chemical characteristics of cells are made while the cells pass, in single file, through the measuring apparatus in a fluid stream. FACS instruments allow for rapid counts and sorting of heterogeneous suspensions of small particles or cells. In particular, fluorescence-based flow cytometry in which the physical and/or chemical characteristics are measured indirectly by fluorochrome-labeled molecular probes that selectively associates with a target molecule may be used. The sensitivity of these instruments currently allows detection of up to several thousand particles per second. Among flow cytometry systems currently available are the EPICS Elite ESP (Coulter Corp., Miami, Fla.) and FACS-Calibur (Becton Dickinson Immunocytometry Systems, San Jose, Calif.).

For single molecule detection, an observable event such as a reaction may be monitored using such single molecule detection schemes. This aspect of the invention can be practiced using optical set-ups including near-field scanning microscopy, far-field confocal microscopy, wide-field epi-illumination, internal reflection fluorescence (TIRF) microscopy. Suitable photon detectors include, but are not limited to, photodiodes and intensified CCD cameras. Fluorescence imaging using epi-illumination, confocal, or total-internal-reflection optical microscopy permits characterization of the quantities, locations, and interactions of fluorochrome-labeled target materials within living cells. All fluorescence observables that can be analyzed in vitro—emission intensity, emission lifetime, fluorescence correlation, FP/FA, and FRET—also can be analyzed in living cells (Nakanishi et al. *Anal. Chem.* 73:2920-2928 (2001); Maiti, S. et al. *Proc. Natl. Acad. Sci. USA* 94: 11753-11757 (1997); Eigen and Rigler, *Proc. Natl. Acad. Sci. USA* 91:5740-5747 (1994) for example of uses of fluorescence in living cells).

Multiplex Analysis

It is also possible to monitor reaction of multiple biological target materials simultaneously using currently available single molecule detection instrumentation. Particularly advantageous is the use of an intensified charge couple device (ICCD) camera to image individual SARPs in a fluid near the surface of the glass slide. Using an ICCD, a sequence of images (movies) of fluorophores may be obtained. In one embodiment, each target material has a unique donor emission spectrum associated therewith, each being discernable from the other. A color instrument is used having multiple cameras and multiple excitation lasers to observe a plurality of reactions of the various target materials. This permits simultaneous imaging of many different target materials spread on a microscope slide. Moreover, with the use of image analysis algorithms, it is possible to track the path of single SARPs and distinguish them from fixed background fluorescence and from "accidentally excited" fluorescent conjugates moving transiently into the field of view.

The SARPs of the present invention can therefore be used, in vitro or in vivo, in fluorescence assays with "multiplex" detection, wherein a plurality of different SARPs emitting in different wavelengths are attached to a plurality of different primary molecules, molecule 1a, 1b, . . . 1n, with each primary molecule being specific for a different secondary component, 2a, 2b, . . . 2n, in order to monitor a plurality of reactions between primary molecules and secondary molecules in a single reaction mixture. According to this method of use, each of the primary molecules is separately labeled with a SARP having a different, distinguishable excitation and/or emission wavelength. The primary molecules are then reacted, as a group, with the secondary molecules, as a group, and fluorescence is monitored at each of different, distinguishable excitation and/or emission wavelengths.

The fact that SARPs may be designed having different, distinguishable excitation and emission wavelengths, makes the invention particularly important for applications involving multiplex detection.

Immobilization and Affinity Purification

It is further contemplated that the SARPs of the invention may be used for immobilization and/or affinity-purification of target-sequence-containing molecules. Immobilization may be accomplished by: (a) covalently attaching a pair of proximate fluorescent conjugates to a surface (via, for example, detectable group X or a linker), (b) contacting the surface with a solution containing a target-sequence-containing target material, and (c) optionally washing the surface to remove unbound material.

Affinity purification may be accomplished by: (a) covalently attaching a pair of fluorescent conjugates to a surface or other solid support, (b) contacting the resulting fluorescent-conjugate-containing surface or other solid support with a solution containing a target-sequence-containing molecule, (c) optionally washing the surface or other solid support to remove unbound material, and (d) eluting the target-sequence-containing molecule with a low-molecular-weight monothiol (e.g., β-mercaptoethanol) or, preferably, a low-molecular-weight dithiol (e.g., dithiothreitol or ethanedithiol) for bis-arsenical containing conjugates or nitrilotriacetic acid for transition metal containing conjugates.

One of ordinary skill in the art will appreciate various other schemes for linking target materials such as nucleic acids and proteins to support surfaces. Typical surfaces include a bead, a gel, a chromatographic matrix, and the like. Moreover, the choice of support and method of immobilization are largely a matter of convenience and depends on the practitioner's familiarity with, and preference for, various support surfaces, and the like.

DNA/Protein Interactions

Nucleotides labeled with SARPs may be used in standard blotting, immunohistochemistry, ELISA's, and hybridization procedures such as DNA sequencing including in situ hybridization. Anti-digoxigenin Fab fragments are available from Roche Diagnostics Corp., Indianapolis, Ind.

A SARP may be bound to a peptide nucleic acid (PNA) molecule for detection of a DNA sequence of interest, to which the PNA is complimentary and may be conjugated. A PNA is a pseudopeptide including a base pairing segment attached to a sugar or modified sugar backbone of DNA by molecular linkages. Examples of linkages include methylene carbonyl, ethylene carbonyl and ethyl linkages (Nielsen et al., *Peptide Nucleic Acids-Protocols and Applications*, Horizon Scientific Press, pages 1-19; Nielsen et al., *Science* 254: 1497-1500). A PNA can be chemically synthesized by methods known in the art, e.g. by modified Fmoc or tBoc peptide synthesis protocols.

Detecting a DNA strand of interest, may be accomplished by: (a) preparing a reaction mixture of (i) a PNA complimentary to the DNA of interest labeled with a SARP and (ii) a sample of the DNA of interest, and (b) detecting complex formation of the DNA and PNA. Optionally, the DNA strand or the PNA is immobilized on a surface or solid phase.

In a particularly useful aspect of the invention, a digoxigenin (DIG) may be incorporated into a target material, in particular a nucleotide. The DIG may, for example, be incorporated into a target nucleotide using generally available polymerases such as Taq polymerase. The DIG nucleotide complex may be reacted with a SARP labeled anti-DIG. The anti-DIG selectively associates with DIG. Upon introduction of the SARP labeled anti-DIG into a sample containing a DIG labeled nucleotide, presence of the nucleotide may be detected. Alternatively, the anti-DIG may be tagged with a third fluorescent conjugate which performs a detectable energy relay with the SARP. Association of the anti-DIG to the DNA/DIG complex may be detected by measuring the relayed energy.

The probe according to the invention may also be used in an assay for in vivo visualization of chromosomes using lac-operator-repressor binding. In this assay, a lac repressor acts as a tag and is labeled with a SARP according to the invention. The lac repressor selectively binds to a site on DNA containing the operator sequence for lac-repressor. Presence of the lac repressor-operator complex is detected by imaging the fluorescent energy transfer of the SARP. Mobility and conformational changes of specific amplified chromosome regions in cells may thus be observed during the interphase cell cycle. Belmont and Straight, *Cell Biology*, 8:121-123.

Use of the probe according to the present invention in gene regulation assays is also advantageous. In one assay, a systematic base pair substitution analysis may be performed in which the affinity of a regulatory gene product (i.e., a catabolite gene activator protein (CAT)) to variants in its DNA consensus site can be evaluated using SARP. In this assay, the effects of substitution of DNA base pairs on the binding site for the regulatory protein on efficiency of binding of the protein thereto may be determined by imaging.

Here, a CAP protein having high affinity for the DNA consensus site is tagged and labeled with SARP. The energy transfer in SARP will be used to determine the extent of binding of CAP to the test sites by measuring comparative amounts and duration of CAP/DNA complex formation. The change in the amount and duration of binding of the CAP to experimentally varied consensus sites will determine the effect of the variants on DNA/CAP protein binding. Gunasekera, et al., *J. Biological Chem.*, 267:14713-14720 (1992).

The following references are herein incorporated by reference and relate to the examples set forth below:

1. Fisher, N. and Hamer, F., Tricarbocyanines. *J. Chem. Soc.* 189-193 (1933).
2. Mujumdar, et al., R., "Cyanine dye labeling reagents: sulfoindocyanine succinimidyl esters," *Bioconj. Chem.* 4, 105-111 (1993).
3. Mekler, M., et al., "Structural organization of RNA polymerase holoenzyme and the RNA polymerase-promoter open complex: systematic fluorescence resonance energy transfer and distance-constrained docking, "*Cell,* 108, 599-614 (2002).
4. Niu, W., "Identification and characterization of interactions between a transcription activator and the transcription machinery, " Ph.D dissertation, Rutgers University, New Brunswick, N.J. (1999).
5. Tang, H., et al., "Location, structure, and function of the target of a transcriptional activator protein," *Genes & Dev,* 8:3058-3067 (1995).
6. Kunkel, T. "Rapid and efficient site-specific mutagenesis without phenotypic selection," *Proc. Natl. Acad. Sci. USA* 82, 488-492 (1985).
7. Tang, H., et al., "Rapid RNA polymerase genetics: one-day, no-column preparation of reconstituted recombinant *Escherichia coli* RNA polymerase," *Proc. Natl. Acad. Sci. USA* 92, 4902-4906 (1995).
8. Studier, F., et al., "Use of T7 RNA polymerase to direct expression of cloned genes,: *Methods Enzylomol.* 185, 125-138 (1990).

EXAMPLE 1

Synthesis of a $(Ni^{2+}\text{-NTA})_1$-Cy3 Transition Metal Probe

A. Preparation of $(NTA)_1$-Cy3

N-(5-amino-1-carboxypentyl)iminodiacetic acid (Dojindo; 26 mg; 80 µmol) was dissolved in 1.6 ml 0.1M sodium carbonate and was added to Cy3 mono-succinimidyl-ester ("Cy3 Mono-Reactive Dye" from Amersham-Pharmacia Biotech; 800 nmol). Following reaction for 1 hour (with vortexing at 15-min intervals) at 25° C. in the dark, the product was purified from excess N-(5-amino-1-carboxypentyl)iminodiacetic acid using a Sep-Pak C18 cartridge (Millipore; pre-washed with 10 ml of acetonitrile and 10 ml water, washed with 20 ml water; eluted with 1 ml 60% methanol), dried, re-dissolved in 500 µl water, and further purified by FlAsH chromatography [silica gel, NH$_4$OH:ethanol:water in a 55:35:10 v/v/v TLCr$_f$=0.6]. The product was dried, redissolved in 2 ml water, and quantified spectrophotometrically ($\epsilon_{550}$=150,000 M$^{-1}$ cm$^{-1}$). Yield 130 nmol, 16%.

B. Preparation of $(Ni^{2+}:NTA)_1$-Cy3

NiCl$_2$ (Aldrich; 350 nmol in 3 µl of 0.01N HCl) was added to $(Ni^{2+}:NTA)_1$-Cy3 (70 nmol in 2 ml water), and the solution was brought to pH 7 by addition of 0.8 ml 50 mM sodium acetate (pH 7), 200 mM NaCl. Following reaction for 30 min at 25° C. in the dark, the product was purified using a Sep-Pak C18 cartridge ((Millipore; procedure as above) and dried. ES-MS: m/e 928.6 (calculated 928.2). Ni$^{2+}$ content [determined by performing analogous reaction with $^{63}$NiCl$_2$ (New England Nuclear) and quantifying radioactivity by scintillation counting in Scintiverse II (Fischer)]: 0.92 mol Ni$^{2+}$ per mol.

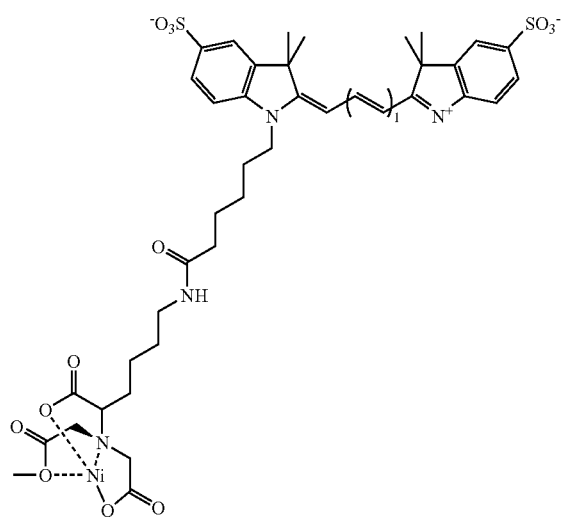

EXAMPLE 2

Synthesis of a $(Ni^{2+}\text{-NTA})_1$-Cy5 Transition Metal Probe

A. Synthesis of $(NTA)_1$-Cy5

N-(5-amino-1-carboxypentyl)iminodiacetic acid (Dojindo; 26 mg; 80 µmol) was dissolved in 800 µl 0.1M sodium carbonate and was added to Cy5 mono-succinimidyl-ester ("Cy5 Mono-Reactive Dye" from Amersham-Pharmacia Biotech; 800 mmol). Following reaction for 1 h (with vortexing at 15-min intervals) at 25° C. in the dark, the product was purified from excess N-(5-amino-1-carboxypentyl)iminodiacetic acid using a Sep-Pak C18 cartridge (Millipore; procedure as above), dried, re-dissolved in 500 µl water, and further purified by FlAsH chromatography (silica gel; ethanol TLC r$_f$=0.2). The product was dried, re-dissolved in 100 µl water and quantified spectrophotometrically ($\epsilon_{550}$=250,000 M$^{-1}$ cm$^{-1}$). Yield: 77 nmol; 9.6%. ES-MS: m/e 896.7 (calculated 896.3).

B. Synthesis of $(Ni^{2+}:NTA)_1$-Cy5

NiCl$_2$ (Aldrich; 50 nmol in 0.5 µl of 0.01 N HCl) was added to $(NTA)_1$-Cy5 (30 nmol in 1 ml water), and the solution was bought to pH 7 by addition of 0.5 ml 50 mM sodium acetate (pH 7), 200 mM NaCl. Following reaction for 30 min at 25° C. in the dark, the product was purified using a Sep-Pak C18 cartridge (Millipore; procedure as above) and dried. ES-MS: m/e 955.0 (calculated 954.2).

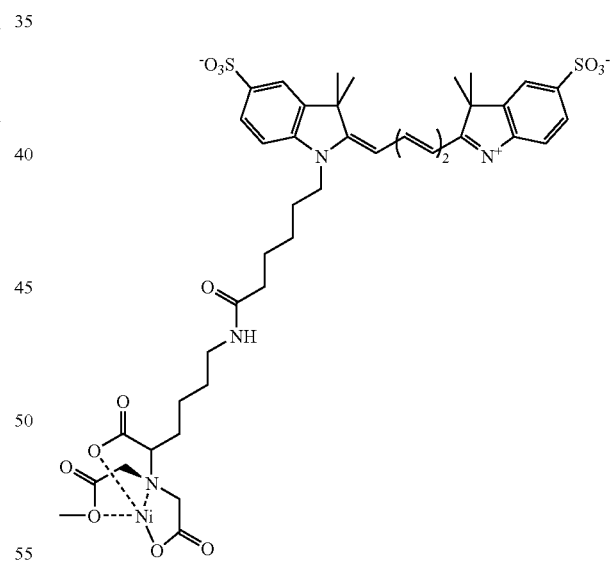

EXAMPLE 3

Synthesis of a $(Ni^{2+}\text{-NTA})_1$-Cy3 Transition Metal Probe

A. Synthesis of $(NTA)_2$-Cy3

N-(5-amino-1-carboxypentyl)iminodiacetic acid (Dojindo; 26 mg, 80 µmol) was dissolved in 1.6 ml 0.1 M sodium carbonate and was added to Cy3 bis-succinimidyl-ester ("Cy3 Reactive Dye" from Amersham-Pharmacia Biotech). Following reaction for 1 hour (with vortexing at 15-min intervals) at 25° C. in the dark, products were purified from excess N-(5-amino-1-carboxypentyl)iminodiacetic acid using a Sep-Pak C18 cartridge ((Millipore; pre-washed with 10 ml of acetonitrile and 10 ml water; washed with 20 ml water; eluted with 1 ml 60% methanol), dried, re-dissolved in 200 μl methanol, and purified by preparative TLC [1000 Å silica gel (Analtech); NH$_4$OH:ethanol:water 55:35:10 v/v/v]. Three bands were resolved, corresponding to (NTA)$_2$-Cy3 ($r_f$=0.2), (NTA)$_1$-Cy3 mono acid ($r_f$=0.5), and (NTA)$_2$-Cy3 bis acid ($r_f$=0.8). (NTA)$_2$-Cy3 was eluted using 60% methanol, dried, re-dissolved in 2 ml water and quantified spectrophotometrically ($\epsilon_{550}$=150,000 M$^{-1}$ cm$^{-1}$). The yield was 64 nmol, 8%. ES-MS: m/e 1197.0 (calculated 1197.4).

B. Synthesis of (Ni$^{2+}$:NTA)$_2$-Cy3

NiCl$_2$ (Aldrich; 350 nmol of NiCl$_2$ in 3 μl of 0.01 N HCl) was added to (NTA)$_2$-Cy3 (70 nmol in 2 ml water), and the solution was brought to pH 7 by addition of 0.8 ml 50 mM sodium acetate (pH 7), 200 mM NaCl. Following reaction for 30 min. at 25° C. in the dark, the product was purified using a Sep-Pak C18 cartridge ((Millipore; procedure as above) and dried. ES-MS: m/e 1316.8 (calculated 1315.7). Ni$^{2+}$ content [determined by performing analogous reaction with $^{63}$NiCl$_2$ (New England Nuclear) and quantifying reactivity in product by scintillation counting in Scintiverse II (Fischer)]: 1.4 mol Ni$^{2+}$ per mol.

EXAMPLE 4

Synthesis of a (Ni$^{2+}$:NTA)$_2$-Cy5 Transition Metal Probe

A. Synthesis of (NTA)$_2$-Cy5

N-(5-amino-1-carboxypentyl)iminodiacetic acid (Dojindo; 40 mg; 125 μmol) was dissolved in 0.8 ml 0.1 M sodium carbonate and was added to Cy5 bis-succinimidyl-ester ("Cy5 Reactive Dye" Amersham-Pharmacia Biotech; 800 nmol). Following reaction for 1 h (vortexed at 15 minute intervals) at 25° C. in the dark, products were purified from excess N-(5-amino-1-carboxypentyl)iminodiacetic acid using a Sep-Pak C18 cartridge ((Millipore; procedure as above), dried, re-dissolved in 200 μl methanol, and purified in 100 μm portions by preparative TLC [silica gel, 1000 Å (Analtech); NH$_4$OH:ethanol:water in a 55:35:10 v/v/v. Three bands were resolved, corresponding to (NTA)$_2$-Cy5 ($r_f$=0.2), (NTA)$_1$-Cy5 mono acid ($r_f$=0.6), and (NTA)$_2$-Cy5 bis acid ($r_f$0.8). The (NTA)$_2$-Cy5 was eluted with 60% methanol, dried, re-dissolved in 2 ml water and quantified spectrophotometrically ($\epsilon_{550}$=250,000 M$^{-1}$ cm$^{-1}$). Yield: 60 nmol; 7.5%.

B. Synthesis of (Ni$^{2+}$:NTA)$_2$-Cy5

NiCl$_2$ (Aldrich; 90 nmol in 1 μl of 0.01 N HCl) was added to (Ni$^{2+}$:NTA)$_2$-Cy5 (30 mmol in 1 ml water), and the solution was bought to pH 7 by addition of 0.5 ml 50 mM sodium acetate (pH 7), 70 mM NaCl. Following reaction for 30 min. at 25° C. in the dark, the product was purified using a Sep-Pak C18 cartridge ((Millipore; procedure as above) and dried. ES-MS: m/e 1341.0 (calculated 1341.7).

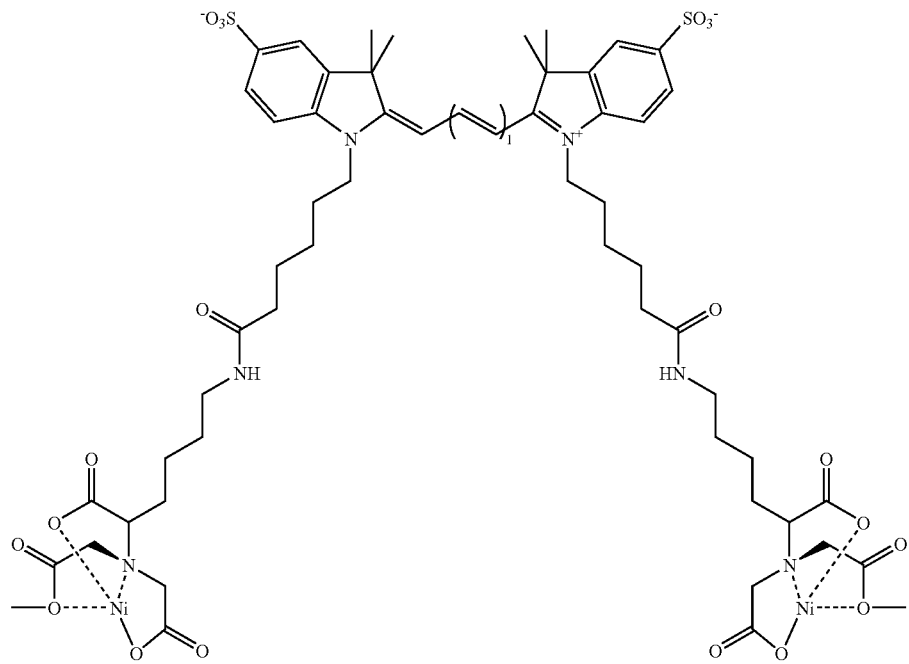

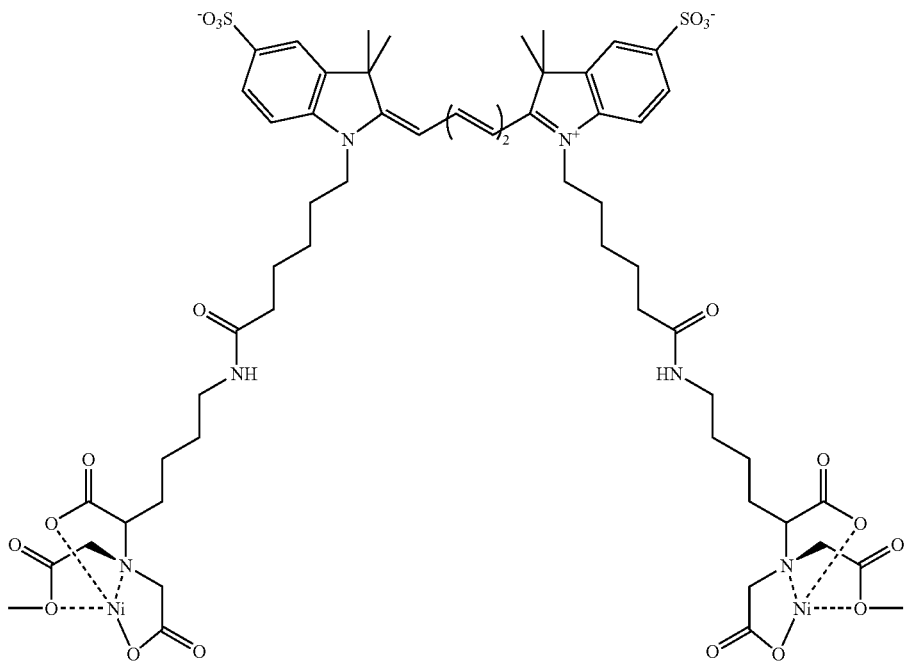

Table 2 depicts the spectroscopic properties of the bidentate fluorochrome conjugates described above. The excitation and emission maxima, and the quantum yield are listed. $Ni^{2+}$ free analogues exhibit identical $\lambda_{max,exc}$ and $\lambda_{max,em}$ and 3.8-fold higher Q (with the higher Q presumably reflecting the unavailability of nonradiative decay involving $Ni^{2+}$ d orbitals).

TABLE 2

Spectroscopic Properties of Fluorochrome Conjugates

| fluorochrome | $\lambda_{max,exc}$ (nm) | $\lambda_{max,em}$ (nm) | Quantum Yield (Q) |
| --- | --- | --- | --- |
| $(Ni^{2+}-NTA)_2-Cy3$ | 552 | 565 | 0.04 |
| $(Ni^{2+}-NTA)_2-Cy5$ | 650 | 668 | 0.05 |

EXAMPLE 5

Preparation of a C-Terminally Hexahistidine Tagged Derivative of the Transcriptional Activator CAP (CAP-$His_6$ Tag)

A. Preparation of CAPHis$_6$

Plasmid pAKCRP-His$_6$ encodes CAP-His$_6$ under the control of bacteriophage T7 gene 10 promotor. Plasmid AKCRP-His$_6$ was constructed from plasmid pAKCRP (as described in Kapanidis, A. et al., *J. Mol. Biol.* 312:453-468 (2001) by using site-directed mutagenesis (as described in Kukel, et al., *J. Meths. Enzymol.*, 204:125-138 (1991)) to insert six His codons (CAC-CAC-CAC-CAC-CAC-CAC) after codon 209 of the crp gene.

To prepare CAP-His$_6$, a culture of *E. coli* strain BL21 (DE3) (Novagen) transformed with pAKCRP-His$_6$ was shaken at 37° C. in 1 L LB (as described in Miller, J., *Experiments in Molecular Genetics*, Cold Spring Harbor Laboratory, Cold Spring Harbor, N.Y. (1972)) containing 200 mg/ml ampicillin until OD600=0.5, induced by addition of isopropyl-thio-β-D-galactoside to 1 mM, and shaken an additional 3 h at 37° C. The culture was harvested by centrifugation (4,500×g; 15 min. at 4° C.), the cell pellet was re-suspended in 15 ml buffer A [20 mM Tris-HCl (pH 7.9), 500 mM NaCl, 5 mM imidazole], cells were lysed by sonication, and the lysate was cleared by centrifugation (30,000×g; 30 min. at 4° C.). The sample was adjusted to 15 ml with buffer A, adsorbed onto 2 ml $Ni^{2+}$-NTA agarose (Qiagen) in buffer A, washed with 12 ml buffer A containing 20 mM imidazole, and eluted with 6×1 ml buffer A containing 200 mM imidazole.

Fractions containing CAP-His$_6$ were pooled, desalted twice into buffer B [40 mM Tris-HCl (pH 8), 100 mM NaCl, 1 mM dithiothreitol, 5% glycerol] by gel-filtration chromatography on NAP-10 (Amersham-Pharmacia Biotech), quantified spectrophotometrically ($\epsilon_{278, protomer}$=20,000 $M^{-1}$ $cm^{-1}$), and stored in aliquots at −80° C. Yield ~20 mg/L culture. Purity 99%.

EXAMPLE 6

Verification of Affinity and Specificity of Association of $(Ni^{2+}-NTA)_2Cy3$ and $(Ni^{2+}-NTA)_2Cy5$ with Target Material Affinity and specificity of association of the probe with target material were evaluated using fluorescence anisotropy assays (methods as in Jameson and Dwyer, *Methods Enzymol.*, 246:283-300 (1995)). Formation of a complex of the probe with a tagged protein was detected as an increase in fluorescence anisotropy, A, arising from the increase in molecular size and corresponding decrease in rotational dynamics.

A. Titration of Probe with Labeled CAP-His$_6$

Reaction mixtures [200 μl, in 100 μl quartz micro-cuvettes (Starna)] contained 50 nM of $(Ni^{2+}-NTA)_2$-Cy3 or $(Ni^{2+}-NTA)_2$-Cy5 in buffer C [40 mM Tris-HCl (pH 8), 100 mM NaCl, 1 mM dithiothreitol, 0.5 mM imidazole, 0.2 mM cAMP, 100 μg/ml bovine serum albumin, and 5% glycerol].

Reaction mixtures were titrated with 0-3 μM CAP-His$_6$ (or CAP) by successive addition of 0.5-4 μl aliquots of 2-4 μM CAP-His$_6$ (or CAP) in the same buffer. Fluorescence anisotropy was determined at the start of the titration and 5 min after each successive addition in the titration. All solutions were maintained at 25° C.

B. Detection of Fluorescence Anisotropy

Fluorescence measurements were performed using a commercial steady-state fluorescence instrument (QM-1, PTI) equipped with T-format Glan-Thompson polarizers (PTI). Excitation wavelengths were 530 nm for (Ni$^{2+}$-NTA)$_2$-Cy3 and 630 nm for (Ni$^{2+}$-NTA)$_2$-Cy 5. Emission wavelengths were 570 nm for (Ni$^{2+}$-NTA)$_2$-Cy3 and 670 nm for (Ni$^{2+}$-NTA)$_2$-Cy5. Slit widths were 10 nm. Fluorescence emission intensities were corrected for background by subtraction of fluorescence emission for control reactions containing identical concentrations of CAP-His$_6$ or CAP but not containing probe.

Fluorescence anisotropy, A, was calculated using: $A=(I_{VV}-GI_{VH})/(I_{VV}+2G_{VH})$ where $I_{VV}$ and $I_{VH}$ are the fluorescent intensities with the excitation polarizer at a vertical position and the emission polarizers at vertical and horizontal positions, respectively, and G is the grating correction factor. Data were plotted as: $(A-A_0/A_0)$ where A is the fluorescence anisotropy in the presence of the indicated concentration of CAP-His6 or CAP, and $A_0$ is the fluorescence anisotropy in the absence of CAP-His$_6$ or CAP. Equilibrium dissociation constants were calculated using linear regression.

Referring now to FIG. 4, a graphical representation of results of titration of (Ni$^{2+}$-NTA)$_2$-Cy3 with His$_6$-CAP is shown (filled circles). Specific interaction between the (NTA)$_2$-Cy3 and His$_6$-CAP as evidenced by a large, saturable increase in fluorescence anisotropy. High affinity of interaction is evidenced by a low dissociation constant ($K_D$=1.0 μM). Specificity of interaction is evidenced by the absence of a significant increase in fluorescence anisotropy in a control titration with CAP (open circles; >95% specificity)).

Referring now to FIG. 5, a graphical representation of results of titration of (Ni$^{2+}$-NTA)$_2$-Cy5 with His$_6$-CAP is shown (filled circles). Specific interaction between (Ni$^{2+}$-NTA)$_2$-Cy5 and e tagged protein and His$_6$-CAP is evidenced by a large, saturable increase in fluorescence anisotropy. High affinity of interaction is evidenced by a low equilibrium dissociation constant ($K_D$=0.4 μM). Specificity of interaction is evidenced by the absence of a significant increase in fluorescence anisotropy in a control titration with CAP (open circles; (>95% specificity)).

EXAMPLE 7

Verification of Affinity, Specificity, and Stoichiometry of Association of (Ni$^{2+}$-NTA)$_2$Cy3 and (Ni$^{2+}$-NTA)$_2$Cy5 with Target Material Using FRET The affinity, specificity, and stoichiometry of interactions between probes according to the invention and the His$_6$ tag also were verified using FRET assays. A His$_6$-tagged protein-DNA complex, (CAP-His$_6$)-DNA$^F$, was prepared. FRET assays using the probes according to the invention then were performed to verify interactions, to detect a target material, and to measure an intermolecular distance.

A. Preparation of DNA$^F$

DNA$^F$, 53 base pair fluorescein-labeled DNA fragment containing the consensus DNA site for CAP (fluorescein incorporated at position –9 relative to the consensus DNA site for CAP) was prepared as described in Ebright, R. et al., *J. Mol. Biol.* 312:453-468 (2001).

B. FRET Assays—Standard Titrations

Reaction mixtures [200 μl, in 50 μl quartz micro-cuvettes (Starna)] contained 5 nM DNA$^F$ and 50 nM CAP-His$_6$ (or CAP) in buffer C. Reaction mixtures were titrated with 0-3.2 μM 2a or 2b by successive addition of 0.3-1.2 μL aliquots of 30-300 μM of (Ni$^{2+}$-NTA)$_2$-Cy3 or (Ni$^{2+}$-NTA)$_2$-Cy5 in the same buffer. Fluorescence anisotropy was determined at the start of the titration and 5 min after each successive addition in the titration. All solutions were maintained at 25° C.

Fluorescent emission intensities, F, were measured using a commercial steady-state fluorescence instrument (QM-1, PTI) equipped with T-format Glan-Thompson polarizers (PTI) set at 54.7°. Excitation wavelength was 480 nm; emission wavelength ranges were 500-600 nm (titrations with (Ni$^{2+}$:NTA)$_2$-Cy3) or 500-700 (titrations with (Ni$^{2+}$:NTA)$_2$-Cy5); Excitation slit width was 10 nm; emission slit width was 15 nm. Fluorescence emission intensities were corrected for background (by subtraction of fluorescence emission intensities for control reaction mixtures containing identical concentrations of (Ni$^{2+}$:NTA)$_2$-Cy3 or (Ni$^{2+}$:NTA)$_2$-Cy5, but not containing CAP-HiS$_6$ or CAP) and for dilution.

Efficiencies of FRET, E, were calculated as: $E=1-(F^{520/480}/F^{520/480}_o)$ where $F^{520,480}$ is the fluorescence emission intensity of the fluorescein label at the indicated concentration of (Ni$^{2+}$:NTA)$_2$-Cy3 or (Ni$^{2+}$:NTA)$_2$-Cy5 and $F_{520/480_o}$ is the fluorescence emission intensity of the fluorescein label at 0 μM of (Ni$^{2+}$:NTA)$_2$-Cy3 or (Ni$^{2+}$:NTA)$_2$-Cy5. Data were plotted as E vs. titrant concentration, and binding curves and equilibrium dissociation constants were calculated using non-linear regression (as described in Gunasekera, A. et al., *J. Biol. Chem.*, 267:14,713-14,720 (1992)).

Referring now to FIG. 6, a graphical representation of results of titration of the (CAP-His$_6$)-DNA$^F$ complex with (Ni$^{2+}$-NTA)$_2$-Cy3 is shown (filled circles). Specific interaction between the (CAP-His$_6$)-DNA complex and (Ni$^{2+}$-NTA)$_2$-Cy3 is evidenced by a large, saturable increase in FRET. High affinity of interaction is evidenced by a low equilibrium dissociation constant ($K_D$=0.9 μM). Specificity of interaction is evidenced by the absence of a significant increase in fluorescence anisotropy in a control titration with the CAP-DNA$^F$ complex (open circles; (>95% specificity).

Referring now to FIG. 7, a graphical representation of results of titration of the (CAP-His$_6$)-DNA$^F$ complex with (Ni$^{2+}$-NTA)$_2$-Cy5 is shown (filled circles). Specific interaction between the (CAP-His$_6$)-DNA$^F$ complex and (Ni$^{2+}$-NTA)$_2$-Cy5 is evidenced by a large, saturable increase in FRET. High affinity of interaction is evidenced by a low equilibrium dissociation constant ($K_D$=0.3 μM). Specificity of interaction is evidenced by the absence of a significant increase in fluorescence anisotropy in a control titration with the CAP-DNA$^F$ complex (open circles; (>95% specificity).

C. FRET Assays—Stoichiometric Titrations

Stoichiometric titrations were performed analogously to standard titrations (as described in Example 7B), using reaction mixtures containing 0.6-2.6 μM (CAP-His$_6$)-DNA$^F$ [prepared by equilibration of DNA$^F$ with excess CAP-His$_6$ for 20 min. at 25° C., followed by removal of unbound CAP-His6 by filtration through Bio-Rex 70 (Bio-Rad) (according to methods described in Kapanidis, A. N., et al., *J. Mol. Biol.* 312:453468 (2001)], and titrating with 0-12 μM of (Ni$^{2+}$-NTA)$_2$-Cy3 or (Ni$^{2+}$-NTA)$_2$-Cy5 by successive addition of 0.3-1.2 μl aliquots of μM (Ni$^{2+}$-NTA)$_2$-Cy3 or ($Ni^{2+}$-NTA)$_2$-Cy5. Fluorescence emission intensities were corrected for dilution and background, and values of E were corrected for non-specific interactions (by subtraction of values of E for control reaction mixtures omitting CAP-His$_6$). Corrected values of E were plotted as E/E$_{sat}$ vs. titrant concentration where E$_{sat}$ is the E at saturating titrant concentrations).

Referring now to FIG. 8, a graphical representation of results of stoichiometric titration of the (CAP-His$_6$)-DNA$^F$ complex with ($Ni^{2+}$-NTA)$_2$-Cy3 is shown (filled circles). The interaction between with ($Ni^{2+}$-NTA)$_2$-Cy3 and His$_6$ has a stoichiometry of 1:1, as evidenced inflection of the titration curve at a ratio of 1 mole ($Ni^{2+}$-NTA)$_2$-Cy3 to 1 mole CAP-His$_6$ protomer.

Referring now to FIG. 9, a graphical representation of results of stoichiometric titration of the (CAP-His$_6$)-DNA$^F$ complex with ($Ni^{2+}$-NTA)$_2$-Cy5 is shown (filled circles). The interaction between with ($Ni^{2+}$-NTA)$_2$-Cy5 and HiS$_6$ has a stoichiometry of 1:1, as evidenced inflection of the titration curve at a ratio of 1 mole ($Ni^{2+}$-NTA)$_2$-Cy5 to 1 mole CAP-His$_6$ protomer.

D. FRET Assays—Distance Determinations

Donor-acceptor distances, R, were determined using the measured efficiencies of FRET at saturation, E$_{sat}$ (0.45 for titration with ($Ni^{2+}$-NTA)$_2$-Cy3; 0.25 for titration ($N^{2+}$-NTA)$_2$-Cy5; see FIGS. 6, 7), and the measured Förster parameters, R$_0$:

$$E = R_0^6/(R_0^6 + R^6)$$

$$R_0 (\text{in Å}) = (0.211 \times 10^{-5})(n^{-4} Q_{DK}^2 J)^{1/6}$$

wherein n is the refractive index of the medium (1.4 for dilute protein solutions[8]), Q$_D$ is the donor quantum yield in the absence of acceptor [0.4; measured using quinine sulfate in 0.1 N $N_2SO_4$ as standard (Q$_{QS}$=0.51)], $\kappa^2$ is the orientation factor relating the donor emission dipole and acceptor dipole [approximated as 2/3 due to the low fluorescent anisotropy of the donor], and J is the spectral overlap integral of the donor emission spectrum and the acceptor excitation spectrum:

$$J = [\int F_D(\lambda)\epsilon_A(\lambda)\lambda^4 d\lambda] / [\int F_D(\lambda) d\lambda]$$

wherein $F_D(\lambda)$ is the normalized corrected emission spectrum of donor, $\epsilon_A(\lambda)$ is the molar extinction coefficient of acceptor, and $\lambda$ is the wavelength.

Figure 10:
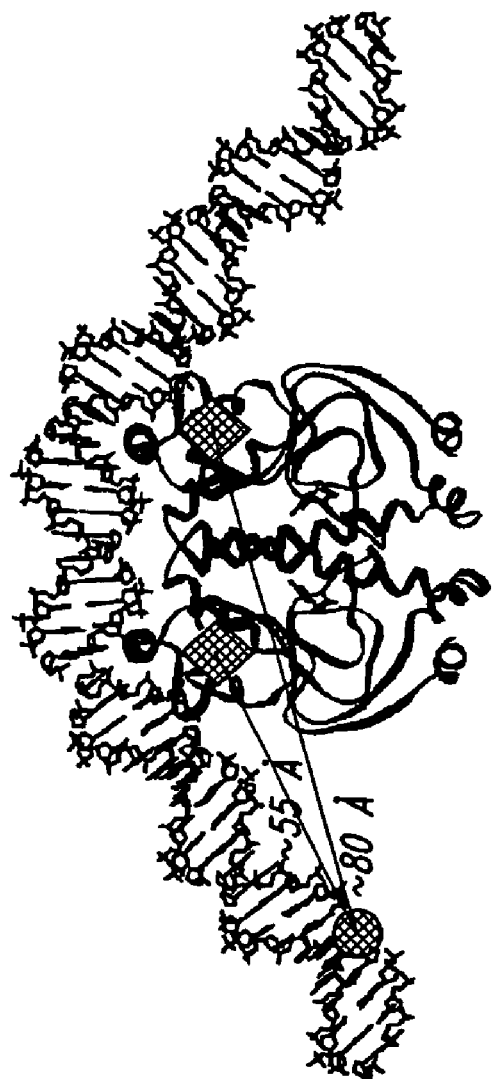
FIG. 10 is a model structure of a $DNA^F$-CAP-$HiS_6$ complex showing the position of the fluorescein of $DNA^F$ (circle), the position of the hexahistidine tag of each CAP-$His_6$ promotor (diamond), the distance between fluorescein and the hexahistidine tag of the proximal CAP-$His_6$ promotor (~55 Å), and the distance between fluorescein and the hexahistidine tag of the distal CAP-$His_6$ promotor (~80 Å).

The analysis above yields a donor-acceptor distance of 56(±4) angstroms (Å). This distance is in excellent agreement with the distance of about 55 angstroms (Å) expected based on structural information as illustrated in FIG. 10 (corresponding to the distance between the fluorescein on DNA and the His$_6$ of the proximal CAP-His$_6$ protomer).

EXAMPLE 8

Synthesis of Cy3 bis-propionamido-phenylarsineoxide [Cy3-(PAO)$_2$]

A1. Synthesis of 4-(bromopropionamido)-phenylarsineoxide

Bromopropionic acid anhydride [formed by reacting bromopropionic acid (1.66 g, 10.86 mmol) with DCC (1.12 g, 5.43 mmol) in 20 ml anhydrous dichloromethane for 15 minutes at 25° C., and filtering off the solid that precipitated] was added to a solution of aminophenylarsineoxide (1 g, 5.43 mmol, synthesized according to published protocol) in 10 ml DMF, and allowed to stir overnight. The amino phenylarsineoxide was rendered soluble by adding to it 10.86 mmol HCl/ether followed by neutralization with triethylamine and filtering away the solid that formed. The solution was quenched with 20 ml water, and filtered to remove solids. The filtrate was evaporated to an oil, and purified via FlAsH chromatography. In later preparations, 3-bromopropionyl chloride was used instead of the anhydride.

A1'a. Alternative Synthesis: 4-(bromopropionamido)-phenylarsanilic Acid

Into 20 ml water was added potassium hydroxide (1 g, 18.4 mmol), p-arsanilic acid (2.04 g, 9.4 mmol), and sodium bicarbonate (3.06 g, 28 mmol). The suspension was stirred until all the solids dissolved. Ice was added to the solution until some ice remained in the solution. Into the icy solution was added 3-bromopropionyl chloride (2.38 g, 13.9 mmol) aliquot-wise over 2 minutes. The solution was vigorously stirred for 5 minutes, then extracted with 10 ml dichloromethane in a separatory funnel. The dichloromethane layer was discarded, the aqueous layer was cooled on ice, and acidified with 50% sulfuric acid until the pH was 1. A white solid precipitated, and was collected via vacuum filtration. Yield: 2.967 g (8.4 mmol, 89% yield). (M+H$^+$): expected, 352, 354. Found, 352, 354.

A1'b. 4-(bromopropionamido)-phenylarsineoxide 20 mg of sodium iodide was added to a solution of 4-(bromopropionamido)-phenylarsanilic acid (1 g, 2.84 mmol) in 10 ml methanol and 10 ml 48% hydrobromic acid. Sulfur dioxide was bubbled into the stirred solution for 15 minutes, during which time a white solid precipitated. The gas was removed, and the suspension stirred for another 5 minutes. The solid was collected via vacuum filtration. Yield: 0.75 g, 2.23 mmol, 78% yield.

B. 4-(2,33-trimethylindolyl)-propionamido-phenylarsineoxide 4-(Bromopropionamido)-phenylarsineoxide as prepared above (0.23 g, 0.72 mmol) and 2,3,3-trimethylindolenine (Aldrich; 160 mg, 10 mmol) were mixed and heated at 80° C. in a screw-top vial for 6 hours. Upon cooling, the purple mass was triturated with copious diethyl ether. The crude product was used without further purification.

C. Cy3 bis-propionamido-phenylarsineoxide [Cy3-(PAO)$_2$]

To 4-(2,33-trimethylindolyl)-propionamido phenylarsineoxide (as prepared above, 0.72 mmol) was added triethyl orthoformate (Aldrich; 100 μl, 0.68 mmol) and 500 μl pyridine in a screw-cap vial. The mixture was heated at 80° C. for 6 hours. Upon cooling, the mixture was triturated with a copious amount of diethyl ether. The solid was collected and purified via FlAsH chromatography (silica, 240-400 mesh, 1-20% MeOH—CHCl$_3$.). Yield: 63 mg. (M+H$^+$): expected, 839.7. Found, 839.4. The mass spectrum indicated that the compound was mainly in the arsonous form. Absorbance at 550 nm and 260 nm indicate the presence of the Cy3 moiety and the phenylarsine group.

EXAMPLE 9

Synthesis of Cy5 bis-propionamido-phenylarsineoxide [Cy5-(PAO)$_2$]

A. Cy5 bis-propionamido-phenylarsineoxide [Cy5-(PAO)$_2$]

Into 4-(2,33-trimethylindolyl)-propionamido-phenylarsineoxide as prepared above, (crude 130 mg, 0.26 mmol) was added 1,3,3-trimethoxypropene (Karl Industries, Inc.; 50 μl, 0.38 mmol) in 400 μl pyridine in a screw-cap vial. The reaction was heated with a heat gun for 3 min, until a turquoise color imparted. Upon cooling, the reaction mixture was triturated with diethyl ether and ethyl acetate. The solid was collected and purified via FlAsH chromatography (silica, 240-400 mesh, 1-20% MeOH—CHCl$_3$.). Yield: 3 mg. M+H+ (after dissolution in methanol in the presence of trace acetic acid): expected, 865.7. Found, 921.3 (arsonous methyl ether).

EXAMPLE 10

Synthesis of Cy3 bis-propionamido-phenylarsine-ethanedithiol [Cy3-(PAEDT)$_2$], method A A. 4-(bromopropionamido)-phenylarsine-EDT 1,2-Ethanedithiol (Aldrich; 25 µl, 0.30 mmol) was added to 4-(bromopropionamido)-phenylarsineoxide as prepared above(100 mg, 0.30 mol) dissolved in 1 ml of hot methanol. After 5 min, a white solid precipitated and was collected. Yield: 63.7 mg, 0.16 mmol, 53%.

B. 4-(2,3,3-trimethylindolyl)-propionamido-phenylarsine-EDT 4-(Bromopropionamido)-phenylarsine-EDT as prepared above(34 mg, 0.086 mmol) and 2,3,3-trimethylindolenine (Aldrich; 50 mg, 0.3 mmol) and were mixed and heated at 90° C. in a screw-top vial for 6 hours. Upon cooling, the purple mass was triturated with copious diethyl ether. Yield: 40 mg. The crude product was used without further purification.

C. Cy3 bis-propionamido-phenylarsine-ethanedithiol [Cy3-(PAEDT)$_2$]

4-(2,33-trimethylindolyl)-propionamido-phenylarsine-EDT as prepared above, (crude, 19 mg, 0.034 mmol) was suspended in 200 µl pyridine and triethyl orthoformate (50 µl, 0.34 mmol) in a screw cap glass vial. The mixture was heated with a heat gun until the deep violet color of the dye stayed constant. Upon cooling to room temperature, the pyridine was evaporated to yield a deep purple solid. It was dissolved in 1 ml methanol and precipitated with ether to yield 23 mg of crude product. FIG. 2, method A, depicts the method of synthesis of [Cy3-(PAEDT)$_2$].

EXAMPLE 11

Synthesis of Cy3 bis-propionamido-phenylarsine-ethanedithiol [Cy3-(PAEDT)$_2$], method B A. Cy3 bis-propionamido-phenylarsine-ethanedithiol [Cy3-(PAEDT)$_2$]

Into a solution of Cy3-(PAO)$_2$ as prepared above (300 nmol in 100 µl DMF), was added 1 µl 1,2-ethanedithiol (Aldrich, 12 µmol). After 10 min at room temperature, the sample was evaporated under high vacuum (yielding an oil), dissolved in chloroform, and purified via FlAsH chromatography (silica, 240-400 mesh, 1-20% MeOH—CHCl$_3$.). Yield: 220 nmol, 73%. (M+H$^+$): expected, 955.2. Found, 955.4. FIG. 2, method B depicts this method of synthesis of Cy3-(PAEDT)$_2$.

EXAMPLE 12

Synthesis of Cy5 bis-propionamido-phenylarsine-ethanedithiol [Cy5-(PAEDT)$_2$], method A A. Cy5 bis-propionamido-phenylarsine-ethanedithiol; Cy5-(PAEDT)$_2$ 4-(2,33-trimethylindolyl)-propionamido-phenylarsine-EDT (crude, 17 mg, 0.031 mmol) was suspended in 200 µl pyridine and 1,3,3-trimethoxypropene (50 µl, 0.38 mmol) in a screw cap glass vial. The mixture was heated with a heat gun until the deep blue color of the dye stayed constant. Upon cooling to room temperature, the pyridine was evaporated to yield a deep blue solid. It was redissolved in 1 ml chloroform and purified using silica chromatography (straight chloroform followed by gradual increase of methanol to 10% methanol). Yield: 7.26 mg, 8.15 µmol, 54%. (M+H$^+$): expected, 981.13. Found, 981.3. FIG. 2, method A, depicts this method of synthesis of Cy5-(PAEDT)$_2$.

EXAMPLE 13

Synthesis of Cy5 bis-propionamido-phenylarsine-ethanedithiol [Cy5-(PAEDT)$_2$], method B A. Cy5 bis-propionamido-phenylarsine-ethanedithiol; Cy5-(PAEDT)$_2$.

Into a solution of Cy5-(PAO)$_2$ as prepared above(300 nmol in 100 µl DMF), was added 1 µl 1,2-ethanedithiol (Aldrich, 12 µmol). After 10 min at room temperature, the sample was evaporated under high vacuum (yielding an oil), dissolved in chloroform, and purified via FlAsH chromatography (silica, 240-400 mesh, 1-20% MeOH—CHCl$_3$.). Yield: 108 nmol, 36%. (M+H$^+$): expected, 981.13. Found, 981.3. FIG. 2, method B, depicts this method of synthesis of Cy5-(PAEDT)$_2$

EXAMPLE 14

Synthesis of Cy7 bis-propionamido-phenylarsine-ethanedithiol [Cy7-(PAEDT)$_2$]

A. Cy7 bis-propionamido-phenylarsine-ethanedithiol; Cy7-(PAEDT)$_2$.

Into 4-(2,3,3-trimethylindolyl)-propionamido-phenylarsine-EDT as prepared above (5.5 mg, 10 µmol) was added glutacoldnadehyde dianil HCl (5.68 mg, 20 µmol, synthesized according to Fisher, N. and Hamer, F. "Tricarbocyanines," *J. Chem. Soc.* 189-193 (1933)) in 50 µl pyridine in a screw-cap vial. The reaction mixture was heated with a heat gun for 3 min until a dark blue color appeared. Upon cooling, the reaction mixture was triturated with diethyl ether, dissolved in the smallest volume MeOH and again triturated with diethyl ether. The solid was collected and purified via FlAsH chromatography (silica, 240-400 mesh, 1-10% MeOH—CHCl$_3$.). The slowest green fraction was collected and gave the correct UV-VIS absorbance (270 nm for the phenylarsine-ethanedithiol moiety and 765 nm for Cy7). Yield: 0.16 µmol (3.2%). (M+H$^+$): expected, 1007.2. Found, 1007.2.

EXAMPLE 15

Synthesis of Cy3 bis-sulfonato bis-propionamido-phenylarsine-ethanedithiol[sulfo-Cy 3-(PAEDT)₂]

A. 4-(2,3,3-trimethylindolyl-5-sulfonato)-propionamido-phenylarsine-ethanedithiol 4-(Bromopropionamido)-phenylarsine-EDT as prepared above (50 mg, 0.127 mmol) and the potassium salt of 2,3,3-trimethyl-indoleninium-5-sulfonate (30 mg, 10.8 mmol; synthesized according to Mujumdar, et al., "Cyanine dye labeling reagents: sulfoindocyanine succinimidyl esters," *Bioconj. Chem.* 4, 105-111 (1993)) were suspended in 500 µl dichlorobenzene and heated at 90° C. in a screw-top vial for 6 hours. Upon cooling, the dichlorobenzene was decanted, the solid was triturated with copious diethyl ether, redissolved in the smallest volume of hot methanol, and upon cooling, reprecipitated with ether. Yield: 50 mg. The crude product was used without further purification.

B. Cy3 bis-sulfonato bis-propionamido-phenylarsine-ethanedithiol: sulfo-Cy3-(PAEDT)₂].

To 4-(2,3,3-trimethyl-5-sulfoindolyl)-propionamido-phenylarsine-EDT as prepared above (crude, 50 mg) was added 200 µl pyridine and triethyl orthoformate (100 µl, 0.67 mmol) in a screw cap glass vial. The mixture was heated with a heat gun until the deep purple color of the dye stayed constant. Upon cooling to room temperature, the pyridine was evaporated to yield a deep purple solid, which was triturated with ether. About 25% of the crude solid was purified by reverse-phase C18 HPLC, and the main peak collected. Yield: 1 mg. (M⁻): expected, 1114.12. Found, 1114.1.

EXAMPLE 16

Synthesis of Cy5 bis-sulfonato bis-propionamido-phenylarsine-ethanedithiol [sulfo-Cy 5-(PAEDT)₂]

Cy5 bis-sulfonato bis-propionamido-phenylarsine-ethanedithiol; [sulfo-Cy5-(PAEDT)₂]

To 4-(2,3,3-trimethyl-5-sulfoindolyl)-propionamido-phenylarsine-EDT as prepared above (crude, 12 mg) was added 100 µl pyridine and 1,3,3-trimethoxypropene (25 µl, 0.19 mmol) in a screw cap glass vial. The mixture was heated with a heat gun until the deep blue color of the dye stayed constant. Upon cooling to room temperature, the pyridine was evaporated to yield a deep blue solid. The solid was triturated with ether to give 20 mg of a deep blue solid. The solid was purified by reverse-phase C18 HPLC, and the last main peak collected. Yield: 600 nmol (M⁻): expected, 1140: 1. Found 1140.4.

Table 3 depicts the spectroscopic properties of the fluorochrome conjugates described above in methanol. The excitation and emission maxima are listed.

TABLE 3

Spectroscopic Properties of Fluorochrome Conjugates in Methanol

| fluorochrome | $\lambda_{max,exc}$ (nm) | $\lambda_{max,em}$ (nm) |
|---|---|---|
| Cy3-(PAO)₂ | 552 | 566 |
| Cy3-(PAEDT)₂ | 552 | 567 |
| sulfo-Cy3-(PAEDT)₂ | 558 | 572 |
| Cy5-(PAO)₂ | 647 | 665 |
| Cy5-(PAEDT)₂ | 648 | 666 |
| sulfo-Cy5-(PAEDT)₂ | 650 | 673 |
| Cy7-(PAEDT)₂ | 743 | 774 |

EXAMPLE 16a

Synthesis of Cy7 bis-sulfonato bis-propionamido-phenylarsine-ethanedithiol [Cy7-(SO3)₂-(PAEDT)₂]

Cy7 bis-sulfonato bis-propionamido-phenylarsine-ethanedithiol; [Cy7-(SO3)₂-(PAEDT)₂]

Glutaconaldehyde dianil hydrochloride (3.6 mg, 12.5 µmol) was heated in DMF (300 µl), acetic anhydride (20 µl) and pyridine (15 µL) in a small capped-vial till the solution turned colorless. The hot solution was added to 4-(2,3,3-trimethyl-5-sulfoindolyl)-propionamido-phenylarsine-EDT (Example 15A; cleaned by triturating with methanol till supernatant was clear, 15 mg, 25 µmol) and further heated until the suspension obtained a deep green color. The reaction mixture was evaporated to dryness, and the solid was triturated copiously with methanol. The solid was dissolved in 20% DMF and purified on a semi-prep C18 reverse phase column. Yield: 234 nmol, (M⁻): expected, 1166.2. Found, 1166.5.

EXAMPLE 16b

Synthesis of Cy3 bis-sulfonato bis-propionamido-phenylarsine-propanedithiol-sulfonic acid [Cy3-(SO3)₂-(PAEDT-SO3)₂]

Cy3 bis-sulfonato bis-propionamido-phenylarsine-propanedithiol-sulfonic acid [Cy3-(SO3)₂(PAEDT-SO3)₂]

To Cy3 bis-sulfonato bis-propionamido-phenylarsine-ethanedithiol (Example 15B; 200 nmol dissolved in 200 µl DMF) was added 2,3-dimercapto-1-propanesulfonic acid (1 mg in 100 µl MeOH). The reaction was allowed to proceed for 2 hours at room temperature after which the solvents were evaporated under high vacuum. The reaction mixture was re-dissolved in 200 water, loaded onto a Sep-Pak C18 cartridge which was then washed with 20 ml water to remove excess 2,3-dimercapto-1-propanesulfonic acid. The dye was eluted with 1 ml 50% acetonitrile, evaporated to dryness, re-dissolved in water, and purified by reverse phase C18 HPLC. Yield: 160 nmol, (M⁻²): expected, 650.1. Found, 650.1.

EXAMPLE 16c

Synthesis of Cy5 bis-sulfonato bis-propionamido-phenylarsine-propanedithiol-sulfonic acid [Cy5-(SO3)₂-(PAEDT-SO3)₂]

Cy5 bis-sulfonato bis-propionamido-phenylarsine-propanedithiol-sulfonic acid [Cy5-(SO3)₂-(PAEDT-SO3)₂]

To Cy5 bis-sulfonato bis-propionamido-phenylarsine-ethanedithiol (100 nmol dissolved in 100 µl DMF) was added 2,3-dimercapto-1-propanesulfonic acid (0.5 mg in 50 µl MeOH). The reaction was allowed to proceed for 2 hours at room temperature after which the solvents were evaporated under high vacuum. The reaction mixture was purified as in example 16b. Yield: 80 nmol. (M$^{-2}$): expected, 663.5. Found 665.1.

EXAMPLE 17

Site-Specific Labeling

A. Plasmids encoding untagged and tagged α derivatives

Plasmid pHTf1α-Bam encodes *Escherichia coli* RNA polymerase α subunit under control of the lpp-'lacPUV5 tandem promoter (Mekler et al., *Cell,* 108, 599-614 (2002); Niu, W., Ph.D dissertation, Rutgers University, New Brunswick, N.J. (1999); Tang et al., *Genes & Dev,* 8:3058-3067 (1995)). The following plasmids encoding tetracysteine-tagged a derivatives were constructed by use of site-directed mutagenesis (methods as in Kunkel, *Proc. Natl. Acad. Sci. USA* 82, 488-492 (1985)):

pHTf1α-Bam(CGPCN), encodes α-CGPCN
pHTf1α-Bam(CGPCCGPCN), encodes α-CGPCCGPCN
pHTf1α-Bam(CGPCGCGPCN), encodes α-CGPCGCGPCN
pHTf1α-Bam(CGPCGGCGPCN), encodes α-CGPCGGCGPCN
pHTf1α-Bam(CPGCN), encodes α-CPGCN
pHTf1α-Bam(CPGCCPGCN), encodes α-CPGCCPGCN
pHTf1α-Bam(CPGCGCPGCN), encodes α-CPGCGCPGCN
pHTf1α-Bam(CPGCGGCPGCN), encodes α-CPGCGGCPGCN
pHTf1α-Bam(CCGPCCN), encodes α-CCGPCCN
pHTf1α-Bam(CCPGCCN), encodes α-CCPGCCN
pHTf1α-Bam(CCPGPCCN), encodes α-CCPGPCCN
pHTf1α-Bam(CCGPGCCN), encodes α-CCGPGCCN
pHTf1α-Bam(CCPGPGCCN), encodes α-CCPGPGCCN
pHTf1α-Bam(CCGPGPCCN), encodes α-CCGPGPCCN Plasmid pHTT7f1-NHα encodes *Escherichia coli* RNA polymerase α subunit with an N-terminal hexahistidine tag under control of the bacteriophage T7 gene 10 promoter (Tang et al., *Proc. Natl. Acad. Sci. USA* 92, 4902-4906 (1995)). pHTT7f1-NHα derivatives were constructed by replacing the ClaI-BamHI rpoA segment of plasmid pHTf1T7-NHα with corresponding segments of plasmid pHTf1α-Bam derivatives.

B. Labeling of Untagged and Tagged α Derivatives, Crude Cell Lysates

Transformants of *E. coli* strain BL21(DE3)) (Novagen; Studier et al., *Methods Enzylomol.* 185, 125-138 (1990)) with pHTT7f1-NHα derivatives were shaken at 37° C. in 10 ml LB containing 2 mg/ml ampicillin until $OD_{600}$=0.7, induced by addition of IPTG to 1 mM, and further shaken for another 3 h at 37° C. Cells were harvested by centrifugation (4,600×g; 5 min, 4° C.), and stored at −80° C. Immediately before use, cells were re-suspended in 600 µl 100 mM Tris-HCl, pH 7.9, 200 mM NaCl, 1 mM β-mercaptoethanol, 1 mM phenylmethylsulfonyl fluoride, 7 µM pepstatin A, and 23 µg/ml lysozyme, incubated 5 min at 4° C., and lysed by sonication. Lysates were cleared by centrifugation (16,000× g; 5 min at 4° C.).

To 100 µl cleared lysate, was added 0, 1, or 10 µl 1 M dithiothreitol (DTT), and bis-arsenical to 20 µM (added as 2 µl of 1 mM solution in dimethylformamide). Following 20 min at 25° C., 15 µl aliquots were mixed with 5 µl 0.25 M Tris-HCl, pH 6.8, 2% SDS, 0.01% bromophenol blue, and 30% glycerol and analyzed by SDS-PAGE on 4-20% gradient gels (Criterion, Bio-Rad, Inc.), followed by x/y fluorescence scanning (for Cy3: Molecular Dynamics FluorImager 595, with excitation=514 nm and emission>610 nm; for Cy5: Molecular Dynamics Storm 860, with excitation=635 nm and emission>650 nm).

Labeling of tagged a derivatives was specific; thus, in reactions in the presence of 10 mM DTI, fewer than ten other proteins in the cell lysates were labeled detectably, and, in reactions in the presence of 100 mM DTT, only one other protein in the cell lysate was labeled detectably. Labeling of tagged α derivatives was tag-dependent and required specific tetracysteine tags; thus, in reactions in the presence of 10 mM or 100 mM DTT, labeling was observed with α-CCPGCCN, α-CCGPCCN and, to a lesser degree, α-CGPCCGPCN, but no labeling was observed with untagged α or α-CGPCN, α-CGPCGCGPCN, and α-CGPCGGCGPCN.

Labeling of tagged a derivatives was specific; thus, in reactions in the presence of 10 and 100 mM DTT, only one other protein in the cell lysate was labeled detectably. Labeling of tagged a derivatives was tag-dependent and required specific tetracysteine tags; thus, in reactions in the presence of 10 mM or 100 mM DTT, labeling was observed with α-CCPGCCN, but no labeling was observed with untagged α or α-CGPCN.

C. Labeling of tagged α, purified protein

To cleared lysates (1.4 ml prepared as above, but from 50 ml cultures), was added 2.8 µl 1 M imidazole and 0.2 ml Ni2+-NTA agarose (Qiagen). Following 15 min at 25° C., samples were transferred to 2 ml columns (Poly-Prep, Bio-Rad, Inc.), washed with 10 ml buffer A (100 mM Tris-HCl, pH 7.9, 200 mM NaCl, 2 mM imidazole, and 5% glycerol), washed with 2 ml buffer A containing 10 mM imidazole, and eluted with 2×1 ml buffer A containing 40 mM imidazole. Samples were dialyzed against 100 mM Tris-HCl, pH 7.9, 200 mM NaCl, 1 mM β-mercaptoethanol, 1 mM DTT, and 5% glycerol. Yield: ~300 µg. Purity: ~85%.

Labeling reactions contained (11 µl): 10 µM α derivative, 450 µM bis-arsenical, 100 mM Tris-HCl, pH 7.9, 200 mM NaCl, 1, 10, or 100 mM DTT, 1 mM β-mercaptoethanol, 9% dimethylormamide, and 5% glycerol. Following 20 min at 25° C., 15 µl aliquots were mixed with 5 µl 0.25 M Tris-HCl, pH 6.8, 2% SDS, 0.01% bromophenol blue, and 30% glycerol and analyzed by SDS-PAGE as described above.

Labeling with bis-arsenicals Cy3-$(PAO)_2$, Cy3-$(PA-EDT)_2$, and Cy5-$(PAO)_2$, Cy5-$(PA-EDT)_2$ was tag-dependent; thus, in reactions in the presence of 1 mM or 5 mM DTT, labeling was observed with α-CCPGCCN, but no labeling was observed with untagged α.

EXAMPLE 18

Immobilization/Affinity-Chromatography

A. Immobilization/Affinity-Chromatography of Untagged and Tagged α Derivatives

Cleared lysates (1 ml, prepared as described above, but from 20 ml cultures) were equilibrated with 1 ml phenylarsine oxide agarose (Thiobond resin; Invitrogen, Inc.; re-suspended and charged per manufacturer's procedures) for 30 min at 25° C. with gentle rocking. Samples were transferred to disposable columns (Poly-Prep, Bio-Rad, Inc.), washed with 3×2 ml buffer B (100 mM Tris-HCl, pH 7.9, 200 mM NaCl, 1 mM EDTA, 1 mM β-mercaptoethanol, and 5% glycerol), washed with 3×2 ml buffer B containing 1 mM DTT, washed with 3×2 ml buffer B containing 10 mM DTT, and eluted with 3×2 ml buffer B containing 100 mM mM DTT. Aliquots (20 µl) were analyzed by SDS-PAGE as described above.

Tagged α could be immobilized on phenylarsine oxide agarose in the absence of DTT, could be retained in the presence of 1 mM DTT and could be eluted in the presence of 10 and 100 mM DTT resulting in ~10-fold purification (α-CCGPCCN and α-CCPGCCN; yield, ~200 µg; purity, >95%). Immobilization and retention was specific; thus, fewer than ten other proteins in the cell lysates were detectably immobilized and retained in the presence of 10 mM DTT. Immobilization was tag-dependent; thus, untagged α could not be retained in the presence of 10 mM DTT.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

EXAMPLE 19

Tagged Peptides

Synthesis of Tagged Peptides

The following tetracysteine-tagged peptides were synthesized and HPLC-purified. Peptides were synthesized in three sets: set A (one tetracysteine tag, charge=0), set B (two tetracysteine tags, charge=-1) and set C (two tetracysteine tags):

Set A: (one tetracysteine tag, charge=0)
Ac-WNCCCCN-CONH$_2$ ("0$^{0}$")
Ac-WNCCGCCN-CONH$_2$ ("G1$^{0}$")
Ac-WNCCGGCCN-CONH$_2$ ("G2$^{0}$")
Ac-WNCCGGGCCN-CONH$_2$ ("G3$^{0}$")
Ac-WNCCGGGGCCN-CONH$_2$ ("G4$^{0}$")
Ac-WNCCGPCCN-CONH$_2$ ("GP$^{0}$")
Ac-WNCCGPGCCN-CONH$_2$ ("GPG$^{0}$")
Ac-WNCCPGCCN-CONH$_2$ ("PG$^{0}$")
Ac-WNCCPGPCCN-CONH$_2$ ("PGP$^{0}$")
Ac-WNCGCCGCN-CONH$_2$
Ac-WNCGCGCGCN-CONH$_2$
Ac-WNCGGCCGGCN-CONH$_2$
Ac-WNCGPCCGPCN-CONH$_2$
Ac-WNCPGCCPGCN-CONH$_2$
Ac-WNCGPCGCGPCN-CONH$_2$
Ac-WNCPGCGCPGCN-CONH$_2$
Ac-WNCGPCGGCGPCN-CONH$_2$
Ac-WNCPGCGGCPGCN-CONH$_2$
Set B: (one tetracysteine tag, charge =-1)
Ac-EWNCCCCN-CONH$_2$ ("0")
Ac-EWNCCGCCN-CONH$_2$ ("G1")
Ac-EWNCCGGCCN-CONH$_2$ ("G2")
Ac-EWNCCGGGCCN-CONH$_2$ ("G3")
Ac-EWNCCGGGGCCN-CONH$_2$ ("G4")
Ac-EWNCCPCCN-CONH$_2$ ("P1")
Ac-EWNCCPPCCN-CONH$_2$ ("P2")
Ac-EWNCCPPPCCN-CONH$_2$ ("P3")
Ac-EWNCCPPPPCCN-CONH$_2$ ("P4")
Ac-EWNCCPPPPPCCN-CONH$_2$ ("P5")
Ac-EWNCCPPPPPPCCN-CONH$_2$ ("P6")
Ac-EWNCCGPCCN-CONH$_2$ ("GP")
Ac-EWNCCGPGCCN-CONH$_2$ ("GPG")
Ac-EWNCCGPPGCCN-CONH$_2$ ("GP2G")
Ac-EWNCCGPPPGCCN-CONH$_2$ ("GP3G")
Ac-EWNCCGPPPPGCCN-CONH$_2$ ("GP4G")
Ac-EWNCCGPPPPPGCCN-CONH$_2$ ("GP5G")
Ac-EWNCCGPPPPPPGCCN-CONH$_2$ ("GP6G")
Ac-EWNCCPGCCN-CONH$_2$ ("PG")
Ac-EWNCCPGPCCN-CONH$_2$ ("PGP")
Ac-EWNCCPPGPPCCN-CONH$_2$ ("P2GP2")
Ac-EWNCCPPPGPPPCCN-CONH$_2$ ("P3GP3")
Set C: (two tetracysteine tags)
Ac-EWNCCPPPCCN-PPPPPPPPP-NCCGCCN-CONH$_2$ ("SARP-P3/G1-PP9")
Ac-EWNCCPPPCCN-PPPPPPPPPPPP-NCCGCCN-CONH$_2$ ("SARP-P3/G1-PP12")
Ac-EWNCCPPPCCN-AE-AAAKEAAAKEAAAKEAAAKA-NCCGCCN-CONH$_2$ ("SARP-P3/G1-HL4X")
Ac-EWNCCPPPPCCN-PPPPPPPPP-NCCGCCN-CONH$_2$ ("SARP-P4/G1-PP9")
Ac-EWNCCPPPPCCN-PPPPPPPPPPPP-NCCGCCN-CONH$_2$ ("SARP-P4/G1-PP12")
Ac-EWNCCPPPPCCN-AE-AAAKEAAAKEAAAKEAAAKA-NCCGCCN-CONH$_2$ ("SARP-P4/G1-HL4X")

EXAMPLE 20

Tagged proteins

A. Plasmids

Plasmid pHTT7f1-NHα encodes *Escherichia coli* RNA polymerase α subunit with an N-terminal hexahistidine tag under control of the bacteriophage T7 gene 10 promoter (Studier, et al. (1990) Methods Enzymol. 185, 125-138). The following pHTTf1-NHα derivatives were constructed by use of site-directed mutagenesis (methods as in Tang, et al. (1995) Genes Dev. 8, 3058-3067):
pHTT7f1-NHα(CCCCN), encodes α-CCCCN ("α-0")
pHTT7f1-NHα(CCGCCN), encodes α-CCGCCN ("α-G1")
pHTT7f1-NHα(CCGGCCN), encodes α-CCGGCCN ("α-G2")
pHTT7f1-NHα(CCGGGCCN), encodes α-CCGGGCCN ("α-G3")
pHTT7f1-NHα(CCGGGGCCN), encodes α-CCGGGGCCN ("α-G4")
pHTT7f1-NHα(CCPCCN), encodes α-CCPCCN ("α-P1")
pHTT7f1-NHα(CCPPCCN), encodes α-CCPPCCN ("α-P2")
pHTT7f1-NHα(CCPPPCCN), encodes α-CCPPPCCN ("α-P3")
pHTT7f1-NHα(CCPPPPCCN), encodes α-CCPPPPCCN ("α-P4")
pHTT7f1-NHα(CCPPPPPCCN), encodes α-CCPPPPPCCN ("α-P5")
pHTT7f1-NHα(CCPPPPPPCCN), encodes α-CCPPPPPPCCN ("α-P6")
pHTT7f1-NHα(CGPCN), encodes α-CGPCN
pHTT7f1-NHα(CGPCCGPCN), encodes α-CGPCCGPCN
pHTT7f1-NHα(CGPCGCGPCN), encodes α-CGPCGCGPCN
pHTT7f1-NHα(CGPCGGCGPCN), encodes α-CGPCGGCGPCN
pHTT7f1-NHα(CPGCN), encodes α-CPGCN
pHTT7f1-NHα(CPGCCPGCN), encodes α-CPGCCPGCN
pHTT7f1-NHα(CPGCGCPGCN), encodes α-CPGCGCPGCN pHTT7f1-NHα(CPGCGGCPGCN), encodes α-CPGCG-GCPGCN pHTT7f1-NHα(CCGPCCN), encodes α-CCGPCCN ("α-GP")

pHTT7f1-NHα(CCPGCCN), encodes α-CCPGCCN ("α-PG")

pHTT7f1-NHα(CCPGPCCN), encodes α-CCPGPCCN ("α-PGP")

pHTT7f1-NHα(CCGPGCCN), encodes α-CCGPGCCN ("α-GPG")

pHTT7f1-NHα(CCPGPGCCN), encodes α-CCPGPGCCN ("α-PGPG")

pHTT7f1-NHα(CCGPGPCCN), encodes α-CCGPGPCCN ("α-GPGP")

pHTT7f1-NHα-(SARP-P3/0-PP9), encodes α-CCPPPCC-PPPPPPPPP-CCCCN ("α-SARP-P3/0-PP9")

pHTT7f1-NHα-(SARP-P3/G1-PP9), encodes α-CCPP-PCC-PPPPPPPPP-CCGCCN ("α-SARP-P3/G1-PP9")

pHTT7f1-NHα-(SARP-P3/G1-PP12), encodes α-CCPP-PCC-PPPPPPPPPPPP-CCGCC ("α-SARP-P3/G1-P 3/G1-PP12")

pHTT7f1-NHα-(SARP-P4/G1-PP9), encodes α-CCPPP-PCC-PPPPPPPPP-CCGCCN ("α-SARP-P4/G1-P4/G1-PP9 ")

pHTT7f1-NHα-(SARP-P3/G1-HL4X), encodes α-CCPP-PCC-ANAAAKNAAAKNAAAKNAAAKA-CCGCCN ("α-SARP-P3/G1-HL4X")

pHTT7f1-NHα-(SARP-P3/G1-HL5X), encodes α-CCPP-PCC-ANAAAKNAAAKNAAAKNAAAKNAAAKA-CCGCCN ("α-SARP-P3/G1-HL5X")

B. Crude Lysates

Transformants of *E. coli* strain BL21(DE3) (Novagen) with pHTT7f1-NHα derivatives were shaken at 37° C. in 10 ml LB containing 2 mg/ml ampicillin until $OD_{600}=0.7$, induced by addition of IPTG to 1 mM, and further shaken for another 3 h at 37° C. Cells were harvested by centrifugation (4600×g; 5 min, 4° C.), and stored at −80° C. Immediately before use, cells were re-suspended in 600 µl 100 mM Tris-HCl, pH 7.9, 200 mM NaCl, 1 mM β-mercaptoethanol, 40 µl/ml 25× EDTA-free protease inhibitor cocktail (Roche Diagnostics, Inc.), and 20 µg/ml lysozyme, incubated 5 min at 4° C., and lysed by sonication. Lysates were cleared by centrifugation (16,000×g; 5 min at 4° C.). Concentration of a derivative: ~1 µM. Purity of α derivative: ~10%.

C. Purified Proteins

To cleared lysates (prepared as above, but from 50 ml cultures) was added 1 µl benzonase nuclease (Novagen), 2.8 µl 1 M imidazole and 0.2 ml Ni2+-NTA agarose (Qiagen). Following 15 min at 25° C., samples were transferred to 2 ml columns (Poly-Prep, BioRad, Inc.), washed with 10 ml buffer A (100 mM Tris-HCl, pH 7.9, 200 mM NaCl, 2 mM imidazole, and 5% glycerol), washed with 2 ml buffer A containing 10 mM imidazole, and eluted with 2×1 ml buffer A containing 40 mM imidazole. Samples were dialyzed against 100 mM Tris-HCl, pH 7.9, 200 mM NaCl, 1 mM β-mercaptoethanol, and 5% glycerol. Yield: ~300 µg. Purity: ~85%. Samples were stored at −80° C.

EXAMPLE 21

Multicolor, Multisite Labeling: Pairs of Peptides

A. Assay

Multicolor, multisite labeling was assessed in electrophoretic-mobility-shift assays. Pairs of tetracysteine-tagged peptides—one neutral tetracysteine-tagged peptide, and one negatively-charged tetracysteine-tagged peptide (the charge difference resulting in different electrophoretic mobilities on the gel, thus allowing the two tetracysteine-tagged peptides to be distinguished)—were analyzed. For each combination of probe and pair of tetracysteine-tagged peptides, three reactions were performed in parallel: one reaction at 5 mM DTT, one reaction at 10 mM DTT, and one reaction at 20 mM DTT. Reaction mixtures contained (7 µl): 50 µM neutral tetracysteine-tagged peptide (Example 19, set A), 50 µM negatively-charged tetracysteine-tagged peptide (Example 19, set B), 25 mM sodium phosphate (pH 7.4), 100 mM KCl, 1 mM tri(2-carboxyethyl)phosphine hydrochloride, 1 mM 2-mercaptoethanesulfonic acid, and 10% DMF. DTT (1 µl of 50 mM DTT for reactions at 5 mM DTT, 1 µl of 100 mM DTT for reactions at 10 mM DTT, and 1 µl of 200 mM DTT for reactions at 20 mM DTT) was added, and samples were incubated 30 min at 25° C. Cy5-(SO3)$_2$-(PAEDT)$_2$ (Example 16, 2 µl of 0.1 et al. (2000) Methods Enzymol. 327, 565-578; 2 µl of 0.1 mM solution in DMF) was then added, and samples were further incubated 20 min at 25° C. Non-denaturing loading buffer (BioRad, Inc.; 5 µl) was added, and 5 µl aliquots were analyzed by non-denaturing PAGE on 15% TBE gels (BioRad, Inc.) followed by x/y fluorescence scanning (for FlAsH detection, Molecular Dynamics FluorImager 595, with excitation=488 nm and emission=515-545 nm; for Cy5 detection, Molecular Dynamics Storm 860, with excitation=635 nm and emission≥650 nm).

B. Results: FlAsH and Cy5-(SO3)$_2$-(PAEDT)$_2$ with "G1$^0$" and "P3"

Figure 11:
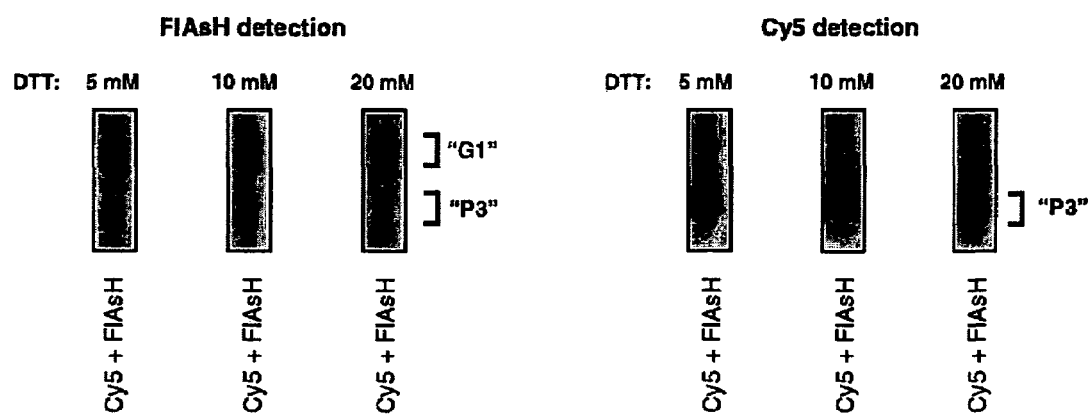
FIG. 11 shows the results for multicolor, multisite labeling with probes FlAsH and Cy5-$(SO_3)_2$-$(PAEDT)_2$ and tetracysteine-tagged peptides "G1°" and "P3".

Results for multicolor, multisite labeling with probes FlAsH and Cy5-(SO3)$_2$-(PAEDT)$_2$ and tetracysteine-tagged peptides "G1$^0$" and "P3" are presented in FIG. 11. FlAsH and Cy5-(SO3)$_2$-(PAEDT)$_2$ exhibited orthogonal specificities. FlAsH labeled "G1$^0$" and did not significantly label "P3" (<<10% level of labeling of "G1$^0$"). Cy5-(SO3)$_2$-(PAEDT)$_2$ labeled "P3" and did not significantly label "G1$^0$" (<<10% level of labeling of "P3").

C. Results: FlAsH and Cy5-(SO3)$_2$-(PAEDT)$_2$ with "G1$^0$" and "P4"

Results for multicolor, multisite labeling with probes FlAsH and Cy5-(SO3)$_2$-(PAEDT)$_2$ and tetracysteine-tagged peptides "G1$^0$" and "P4" were comparable to results for multicolor, multisite labeling with probes FlAsH and Cy5-(SO3)$_2$-(PAEDT)$_2$ and tetracysteine-tagged peptides "G1$^0$" and "P3" (Example 21B; FIG. 11). FlAsH and Cy5-(SO3)$_2$-(PAEDT)$_2$ exhibited orthogonal specificities. FlAsH labeled "G1$^0$" and did not significantly label "P4" (<<10% level of labeling of "G1$^0$"). Cy5-(SO3)$_2$-(PAEDT)$_2$ labeled "P4" and did not significantly label "G1$^0$" (<<10% level of labeling of "P4").

D. Results: FlAsH and Cy5-(SO3)$_2$-(PAEDT)$_2$ with "G1$^0$" and "P5"

Results for multicolor, multisite labeling with probes FlAsH and Cy5-(SO3)$_2$-(PAEDT)$_2$ and tetracysteine-tagged peptides "G1$^0$" and "P5" were comparable to results for multicolor, multisite labeling with probes FlAsH and Cy5-(SO3)$_2$-(PAEDT)$_2$ and tetracysteine-tagged peptides "G1$^0$" and "P3" (Example 21B; FIG. 11). FlAsH and Cy5-(SO3)$_2$-(PAEDT)$_2$ exhibited orthogonal specificities. FlAsH labeled "G1$^0$" and did not significantly label "P5" (<<10% level of labeling of "G1$^0$"). Cy5-(SO3)$_2$-(PAEDT)$_2$ labeled "P5" and did not significantly label "G1$^0$" (<<10% level of labeling of "P5").

E. Results: FlAsH and Cy5-(SO3)$_2$-(PAEDT)$_2$ with "G1$^O$" and "P6"

Results for multicolor, multisite labeling with probes FlAsH and Cy5-(SO3)$_2$-(PAEDT)$_2$ and tetracysteine-tagged peptides "G1$^O$" and "P6" were comparable to results for multicolor, multisite labeling with probes FlAsH and Cy5-(SO3)$_2$-(PAEDT)$_2$ and tetracysteine-tagged peptides "G1$^O$" and "P3" (Example 21B; FIG. 11). FlAsH and Cy5-(SO3)$_2$-(PAEDT)$_2$ exhibited orthogonal specificities. FlAsH labeled "G1$^O$" and did not significantly label "P6" (<<10% level of labeling of "G1$^O$"). Cy5-(SO3)$_2$-(PAEDT)$_2$ labeled "P6" and did not significantly label "G1$^O$" (<<10% level of labeling of "P6").

EXAMPLE 22

Multicolor, Multisite Labeling: Single Peptides (Self-Assembled Relay Probes, SARPs)

A. Assay

Multicolor, multisite labeling of doubly-tetracysteine-tagged peptides—yielding self-assembled relay probes, SARPs—was assessed in electrophoretic-mobility-shift assays. Reaction mixtures contained (16 µl): 100 µM doubly-tetracysteine-tagged peptide (Example 19, set C), 25 mM sodium phosphate (pH 7.4), 100 mM KCl, 1 mM tri(2-carboxyethyl)phosphine hydrochloride, 1 mM 2-mercaptoethanesulfonic acid, and 10% DMF. DTT (2 µl of 50 mM solution) was added, and samples were incubated 30 min at 25° C. Cy5-(SO3)$_2$-(PAEDT)$_2$ (Example 16; 1 µl of 1 mM solution in DMF) was added, and samples were incubated 10 min at 25° C. FlAsH (Griffin, et al. (2000) Methods Enzymol. 327, 565-578; 1 µl of 1 mM solution in DMF) was then added, and samples were further incubated 20 min at 25° C. 5 µl aliquots were mixed with 5 µl non-denaturing loading buffer (BioRad, Inc.) and analyzed by PAGE on 4-20% TBE gels (BioRad, Inc.) followed by x/y fluorescence scanning [for FlAsH detection, Molecular Dynamics FluorImager 595, with excitation at 488 nm and emission 515-545 nm; for Cy5 detection, Molecular Dynamics Storm 860, with excitation=635 nm and emission≧650 nm; for FlAsH-Cy5-FRET-dependent detection (SARP detection), Molecular Dynamics FluorImager 595 and Chroma D680/30M filter, with excitation=488 nm and emission≧680 nm)].

B. Results: FlAsH and Cy5-(SO3)$_2$-(PAEDT)$_2$ with "SARP-P4/G1-PP9"

Figure 12:
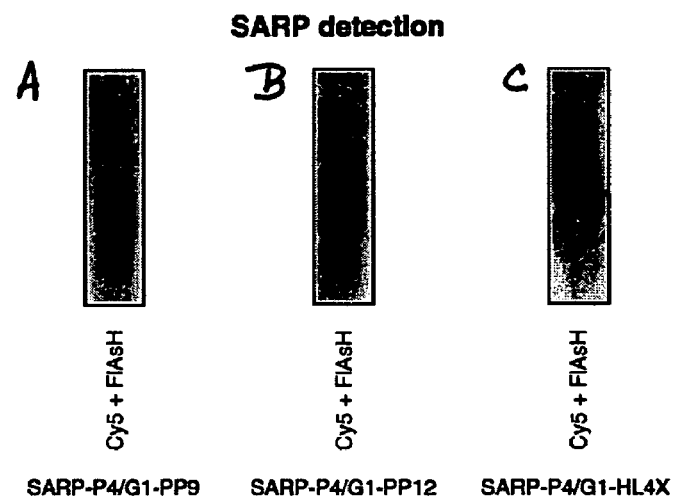
FIG. 12 A. shows the results for multicolor, multisite labeling with probes FlAsH and Cy5-$(SO_3)_2$-$(PAEDT)_2$ and doubly-tetracysteine-tagged peptides "SARP-P4/G1-PP9"; B. shows the results for multicolor, multisite labeling with probes FlAsH and Cy5-$(SO_3)_2$-$(PAEDT)_2$ and doubly-tetracysteine-tagged peptides "SARP-P4/G1-PP12"; C. shows the results for multicolor, multiside labeling with probes FlAsH and Cy5-$(SO3)_2$-$(PAEDT)_2$ and doubly-tetracysterine-tagged peptides "SARP-P4/G1-HL4X".

Results for multicolor, multisite labeling with probes FlAsH and Cy5-(SO3)$_2$-(PAEDT)$_2$ and doubly-tetracysteine-tagged peptides "SARP-P4/G1-PP9" are presented in FIG. 12A. FlAsH and Cy5-(SO3)$_2$-(PAEDT)$_2$ co-labeled "SARP-P4/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

C. Results: FlAsH and Cy5-(SO3)$_2$-(PAEDT)$_2$ with "SARP-P4/G1-PP12"

Results for multicolor, multisite labeling with probes FlAsH and Cy5-(SO3)$_2$-(PAEDT)$_2$ and doubly-tetracysteine-tagged peptides "SARP-P4/G1-PP12" are presented in FIG. 12B. FlAsH and Cy5-(SO3)$_2$-(PAEDT)$_2$ co-labeled "SARP-P4/G1-PP12" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

D. Results: FlAsH and Cy5-(SO3)$_2$-(PAEDT)$_2$ with "SARP-P4/G1-HL4X"

Results for multicolor, multisite labeling with probes FlAsH and Cy5-(SO3)$_2$-(PAEDT)$_2$ and doubly-tetracysteine-tagged peptides "SARP-P4/G1-HL4X" are presented in FIG. 12C. FlAsH and Cy5-(SO3)$_2$-(PAEDT)$_2$ co-labeled "SARP-P4/G1-HL4X" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively.

EXAMPLE 23

Multicolor, Multisite Labeling: Single Proteins (Self-Assembled Relay Probes, SARPs)

A. Assay

Multicolor, multisite labeling of doubly-tetracysteine-tagged proteins—yielding self-assembled relay probes, SARPs—was assessed in electrophoretic-mobility-shift assays. DTT (1 µl of 125 mM solution) was added to 23 µl crude lysate containing doubly-tetracysteine-tagged protein (~1 µM; Example 20B), and samples were incubated 30 min at 25° C. Cy5-(SO3)$_2$-(PAEDT)$_2$ (Example 16; 0.5 µl of 1 mM solution in DMF) was added, and samples were incubated 20 min at 25° C. FlAsH (Griffin, et al. (2000) Methods Enzymol. 327, 565-578; 0.5 µl of 0.1 mM solution in DMF) was then added, and samples were further incubated 5 min at 25° C. 5 µl aliquots were mixed with 5 µl 0.25 M Tris-HCl, pH 6.8, 2% SDS, 0.01% bromophenol blue, and 30% glycerol, and analyzed by SDS-PAGE on 4-20% gradient gels (BioRad, Inc.) followed by x/y fluorescence scanning [for FlAsH detection, Molecular Dynamics FluorImager 595, with excitation=488 nm and emission≧645 nm; for Cy5 detection, Molecular Dynamics Storm 860, with excitation=635 nm and emission≧650 nm; for FlAsH-Cy5-FRET-dependent detection (SARP detection), Molecular Dynamics FluorImager 595 and Chroma D680/30M filter, with excitation=488 nm and emission≧680 nm].

B. Results: FlAsH and Cy5-(SO3)$_2$-(PAEDT)$_2$ with "α-SARP-P3/G1-PP9"

Results for multicolor, multisite labeling with probes FlAsH and Cy5-(SO3)$_2$-(PAEDT)$_2$ and doubly-tetracysteine-tagged protein "α-SARP-P3/G1-PP9" are presented in FIG. 13A. FlAsH and Cy5-(SO3)$_2$-(PAEDT)$_2$ co-labeled "α-SARP-P3/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively. FlAsH and Cy5-(SO3)$_2$-(PAEDT)$_2$ co-labeling and FlAsH-Cy5-FRET-dependent detection was highly specific. Thus, no other protein in the crude lysate was detectably labeled.

C. Results: FlAsH and Cy5-(SO3)$_2$-(PAEDT)$_2$ with "α-SARP-P4/G1-PP9"

Results for multicolor, multisite labeling with probes FlAsH and Cy5-(SO3)$_2$-(PAEDT)$_2$ and doubly-tetracysteine-tagged protein "α-SARP-P4/G1-PP9" are presented in FIG. 13B. FlAsH and Cy5-(SO3)$_2$-(PAEDT)$_2$ co-labeled "α-SARP-P4/G1-PP9" and participated in FlAsH-Cy5 FRET within the resulting complex, as documented by x/y fluorescence scanning with FlAsH-Cy5-FRET-dependent detection (SARP detection). Control experiments omitting FlAsH or omitting Cy5-(SO3)$_2$-(PAEDT)$_2$ yielded no signal or a significantly lower signal, respectively. FlAsH and Cy5-(SO3)$_2$-(PAEDT)$_2$ co-labeling and FlAsH-Cy5-FRET-dependent detection was highly specific. Thus, no other protein in the crude lysate was detectably labeled.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

What is claimed is:

1. A self-assembled relay probe for detecting a target material, comprising:
   (a) a first peptide tag bound to said target material;
   (b) a second peptide tag bound to said target material, wherein said second peptide tag is different from said first peptide tag;
   (c) a first fluorescent conjugate including a first fluorochrome and a first tag binding group; wherein said first fluorescent conjugate selectively associates with said first peptide tag; and
   (d) a second fluorescent conjugate including a second fluorochrome having a longer wavelength and excitation and emission maxima than said first fluoroabrome and a second tag binding group, wherein said second fluorescent conjugate selectively associates with said second peptide tag, whereby upon exposure to said target material, said first and second fluorescent conjugates independently associate with said first and second peptide tags, respectively, so as to be a distance apart represented by about 0.1 $R_0$ to about 2 times $R_0$, such that upon excitation of said first fluorescent conjugate, fluorescence resonance energy transfer results in excitation of said second fluorescent conjugate, yielding detectable emission from said second fluorescent conjugate;

wherein said first fluorescent conjugate is represented by the general structural Formula (IB)

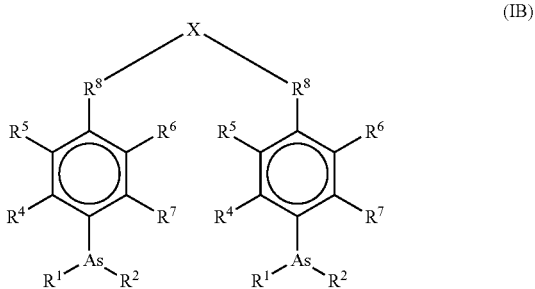

wherein:
(i) $R^1$ and $R^2$, together with the arsenic atom, form a ring according to the general structural Formulae (II)

wherein Z represents a hydrocarbon chain comprising 2-4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thiol, halo (fluoro, obloro, bromo, or fluoro), $(CH_2)_n$-$SO_3$- and $(CH_2)_n$-$SO_3H$, wherein n " is 1 or 2;
(ii) $R^4$, $R^5$, $R^6$ and $R^7$ are each independently H, F, $OR^c$,$R^c$, OAc, $NR^c$, $NH_2$, $N(C_1$-$C_4$ alkyl$)_2$ wherein $R^c$ is H, $CH(OH)CH_2$ OH or $(CH_2)_q$—Y, wherein q is 1-4 and Y is H, OH, $NH_2$, SH, COOH, OAc, $CONH_2$ or CN; or $R^4$with $R^5$, or $R^6$ together with $R^7$, or both, form a ring;
(iii) $R^8$ is a linear or branched optionally substituted spacer having a minimum length of approximately 1.5Ångstroms and a maximum length of approximately 15Ångstroms; and
(iv) X is a cyanine dye.

2. The probe of claim 1, wherein said first fluorescent conjugate and said second fluorescent conjugate do not emit a detectable signal before said detectable energy transfer occurs.

3. The probe of claim 1, wherein said target material is a polypeptide and each of said tags is a tetxa cysteine-containing sequence.

4. The probe of claim 1, wherein at least one of said first and second fluorescent conjugates is a bis-arsenical fluorochrome compound, which selectively associates with a tag including a tetra-cysteine-containing sequence.

5. The probe of clalin 1, wherein at least one of said first and second fluorescent conjugates selectively associates with a tag including a fluoroobrome-blnding sequence.

6. The probe of claim 1, wherein said first and second fluoroebromes are different.

7. The probe of claim 1, wherein said second peptide tag is bound to said target material within less than about 100 angstroms (Å) from said first tag.

8. The probe of claim 1, wherein said first peptide tag and said second peptide tag axe sepanted by a spacer.

9. The probe of claim 8, wherein said spacer includes residues endogenous to said target material and is selected from the group consisting of: a plurality of residues with an oligomeric or monomeric target material, a plurality of residues within a promoter region of an oligorneric target material, and a plurality of residues within different promoter regions of an oligomeric target material.

10. The probe of claim 8, wherein said spacer includes residues exogenous to said target material and is selected from the group consisting of a flexible spacer, a rigid spacer, an alpha-helix, and a protein domain.

11. The probe of claim 8, wherein the spacer is selected from the group consisting of PPPPPPPP (SEQ ID NO:27); PPPPPPPPPPP (SEQ ID NO:28); AEAAAKEAAAKEAAAKEAAAKA. (SEQ ID NO:29); and AEAAAKEAAAKEAAAKEAAAKEAAAKA (SEQ ID NO:30).

12. The probe of claim 1, futher comprising a third peptide tag, and a third fluorescent conjugate, wherein said third fluorescent conjugate selectively associates with said third tag and is capable of participating in a relay energy transfer with one of said first and second fluorescent conjugates, wherein each of said first, second and third tags are different.

13. The probe of claim 1, wherein said first fluorescent conjugate includes a donor dye and said second fluorescent conjugate includes an acceptor dye.

14. The probe of claim 1, wherein at least one of said first and second fluorescent conjugates includes a cyanine dye.

15. The probe of claim 1, wherein said first and second fluorescent conjugates, respectively, are selected from the group consisting of:
(a) Cy5 bis-sulfonato bis-propionamido-pheny1 arsine-ethaneditbiol or Cy5 bis-propionamido -phenylarsine-ethanedithiol /FlAsH-$EDT_2$ (4',5'-bis(1,3,2-ditbioarsolan-2-yl) fluorescein-(1,2-ethanedithiol)$_2$;
(b) Cy5 bis-sulfonato bis-propionamido-phenylarsine-ethanedithiol or Cy5 bis-propionamido -phenylamine-ethanedithiol/ReAsH-$EDT_2$;
(c) Cy3 bis-sulfonato bis-propionamido-phenylarsine-ethanedithiol or Cy3 bis-prapionamido -phenylarsine-ethanedithiol /FlAsH-EDT (4',5'-bis(1,3,2-ditbioarsolan-2-yl) fluorescein-(1,2-ethenedithiol)$_2$; and
(d) Cy3 bis-sulfonato bis-propionamido-phenylarsine-ethanedithiol or Cy3bis-propionamido -phenylarsine-ethanedithiol/ReAsH-$EDT_2$.

16. The probe of claim 1, wherein at least one of said tags is an amino acid sequence of the form: $C(X)_iC(X)_jC(X)_kC$, wherein C is cysteine, X is an amino acid, and i, j, and k are each independently 0 or an integer of from 1 to 8; provided that i, j, and k are all not zero.

17. The probe of claim 1, wherein at least one of said peptide tags and the fluorescent conjugate that selectively associates therewith are selected from the group consisting of a), b) and c):

a) wherein at least one of said peptide tags is selected from the group consisting of: CCGPCC (SEQ ID NO: 2), CCPPPCC (SEQ ID NO:19), CCPPPPCC (SEQ ID NO:20), CCPPPPPCC (SEQ ID NO:21) and CCPGPCC (SEQ ID NO:18), and the fluorescent conjugate is represented by the formula:

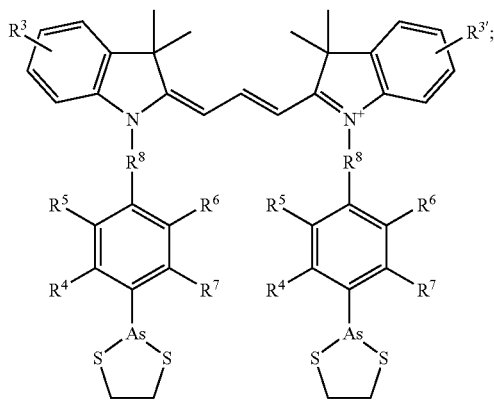

b) wherein at least one of said peptide tags is selected from the group consisting of: CGPCCGP(SEQ ID NO:4), CGPCGCGPC (SEQ ID NO:5), CGPCGGCGPC (SEQ ID NO:6), CCPPPCC (SEQ ID NO:19), CCPPPCC (SEQ ID NO:20), CCPPPPPCC (SEQ ID NO:21), CCPPPPPPCC (SEQ ID NO:22), CCPGPCC (SEQ ID NO:18) and CGCGCGC (SEQ ID NO:23), and the fluorescent conjugate is represented by the formula:

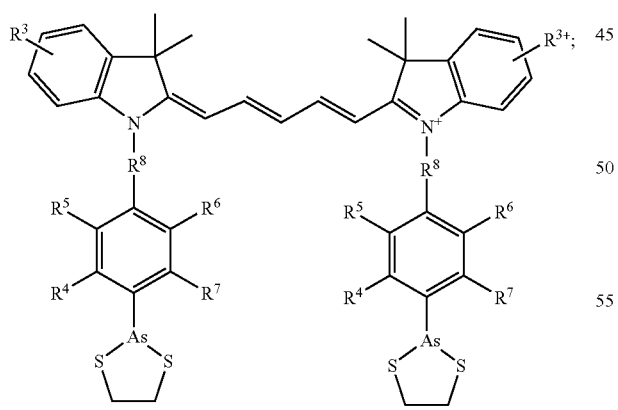

c) wherein at least one of said peptide tags is selected from the group consisting of: CCCC (SEQ ID NO:27) and CCGCC (SEQ ID NO:28), and the fluorescent conjugate is represented by the formula:

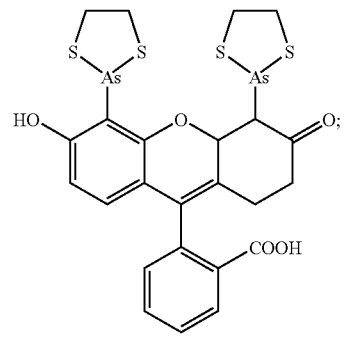

wherein R4,R5,R6,and R7 are each independently H, F, ORc, Rc, OAc,NRc, NH2, or N(C1-C4 alkyl)2; Rc is H ,CH(OH) CH2OH, or (CH2)q-Y, where q is 1-4 and Y is H, OH, NH2, SH, COOH, OAC, CONH2, OAc, CONH2, or CN; R8 is a linear of ranched optionally subsitiuted spacer from about 3 angstroms (Å) to about 15Ålong; and R3 and R3' are each independently H or sulfonate.

18. The probe of claim 1, wherein said first fluorescent conjugate and second fluorescent conjugate are selected from the group consisting of a), b), c), and d):

a) wherein said first fluorescent conjugate is represented by the formula:

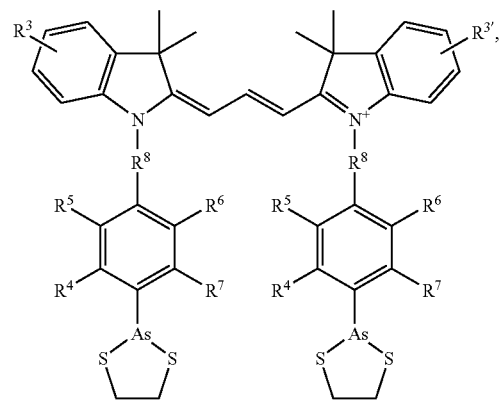

and said second fluorescent conjugate is represented by the formula:

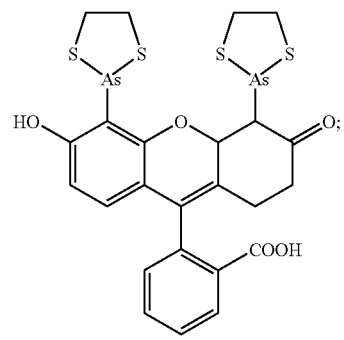

b) wherein said first fluorescent conjugate is represented by the formula:

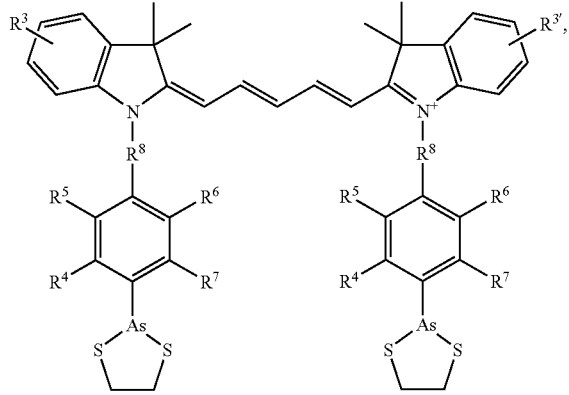

and said second fluorescent conjugate is represented by teh formula:

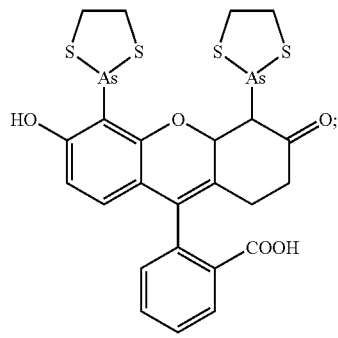

c) where said first fluorescent conjugate is represented by the formula:

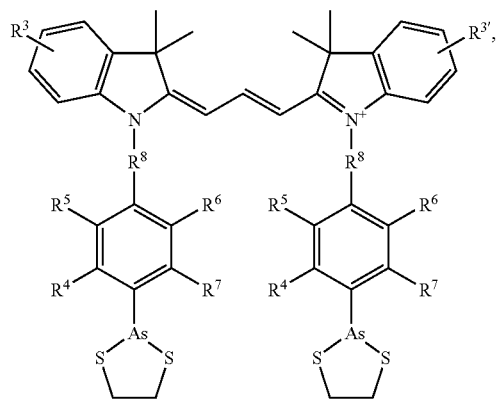

and said second fluorescent conjgate is represented by the formula:

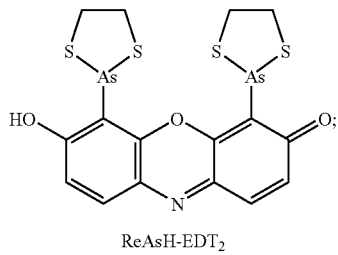

ReAsH-EDT$_2$ d) wherein said first flourescent conjugate is represented by the formula:

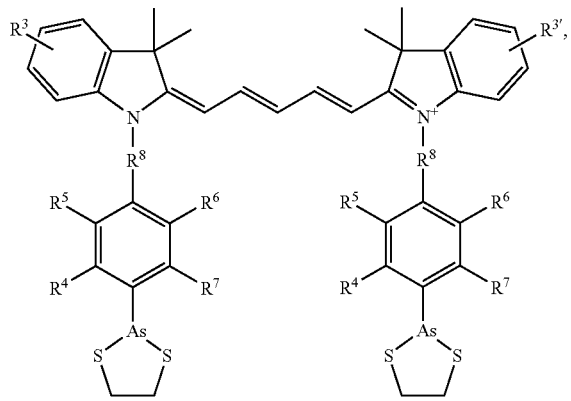

and said second fluorescent conjugate is represented by the formula:

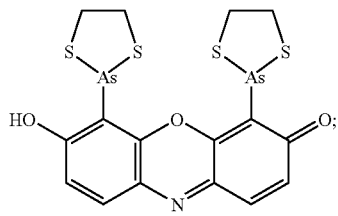

ReAsH-EDT$_2$ wherein R4,R5,R6,and R7 are each independently H, F, ORc, Rc, OAc,NRc, NH2, or N(C1-C4 alkyl)2; Rc is H ,CH(OH) CH2OH, or (CH2)q-Y, where q is 1-4 and Y is H, OH, NH2, SH, COOH, OAc, CONH2, or CN; R8 is a linear of ranched optionally subsitiuted spacer from about 3 angstroms (Å) to about 15Å long; and R3 and R3' are each independently H or sulfonate.

19. The probe of claim 1, wherein $R^1$ and $R^2$, together with the arsenic atom, form a ring according to the general Formulae (II) when Z is CH$_2$SO$_3$— or CH$_2$SO$_3$H.

20. The probe of claim 1, wherein the first peptide tag to which said first fluorescent conjugate selectively binds is of the form: C(X)$_j$C(X)$_i$C(X)$_k$C, wherein C is Cysteine, X is an amino said, and i, j, and k are each independently 0 or an integer of from 1 to 8; provided that i, j, and k are all not zero.

21. The probe of claim 20, wherein said first peptide tag is of the form CC(P)$_n$CC, where C is Cysteine, P is Praline, and n is an integer from 3 to 8.

22. The probe of claim 20, wherein said first peptide tag is selected from the group consisting of CCPPPCC (SEQ ID NO:19); CCPPPPCC (SEQ ID NQ:20); CCPPPPPCC(SBQ ID NO:21); CCPPPPPPCC (SEQ ID NO:22); CCPGPCC (SEQ ID NO:18); CGCGCGC (SEQ ID NO:23) and CGPC-CGPC (SEQ ID NO4).

23. The probe of claim 20, wherein said first fluorescent conjugate is selected from the group consisting of Cy3 bis-sulfonato bis-propionamido-phanylarsifle ethanedithiol, Cy3 bis-propionamido-phenylarsine-ethanedithiol, Cy5 bis-sulfonato bis-propionarnido -phenylarsine-ethanedithiol, and Cy5 bis-propionamido-phenylarsine-ethanedithiol.

24. The probe of claim 1, wherein said first conjugate is represented by the general structural Formula (IB), and wherein said second conjugate is represented by the general structural Formula (VI):

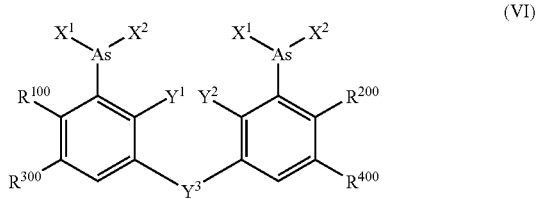

(VI)

wherein each $X^1$ or $X^2$, independently is Cl, Br, I, $OR^\alpha$, or $SR^\alpha$, or $X^1$ and $X^2$ together with the arsenic atom form a ring having the structure:

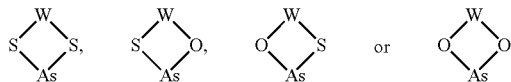

$R^\alpha$ is H, $C_1$-$C_4$ alkyl, $CH_2CH_2OH$, $CH_2COOH$, or CN;

w is 1,2-ethanedlyl, 1,2-propanedlyl, 2,3-butanediyt 1,3-propanediyl, 1,2-beuzenedlyl, 4-methyl-1,2-benzenediyl, 1,2-cyclopentanediyl, 1,2-cyclohexaaediyl, 3-hydroxy-1,2-propenediyl, 3-sulfo-1,2-propanediyl, or 1,2, is (carboxy)-1,2-ethanediyl;

$Y^1$ and $Y_2$, independently, arc H or $CH_3$; or $Y^1$ and $^9$, together form a ring such tbat the biarsenical molecule has the general structure formula:

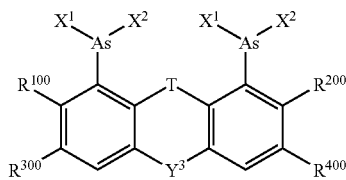

wherein T is O, S, $CH_2$, $C(CH_3)_2$, or NH;

$R^{100}$ and $R^{200}$, independently, are $OR^\alpha$, OAc, $NR^\alpha R^b$, or H;

$R^{300}$ and $R^{400}$, independently, are H, F, Cl, Br, I, $OR^\alpha$, or $R^\alpha$; or $R^{100}$ together with $R^{300}$, or $R^{200}$ together with $R^{400}$, or both, form a ring in which (i) one of $R^{100}$ or $R^{300}$ is $C_2$-$C_3$ alkyl and the other is $NR^\alpha$ and (ii) one of $R^{200}$ and $R^{400}$ is $C_2$-$C_3$ alkyl and the other is $NR^\alpha$;

$R^b$ is H, $C_1$-$C_4$ alkyl, $CH_2CH_2$, OH, $CH_2COOH$, or CN;

$Y^3$ is $CR^\alpha$, $R^b$, $Cr^\alpha OR^b$, C=O, or a spirolactone having one of the structures:

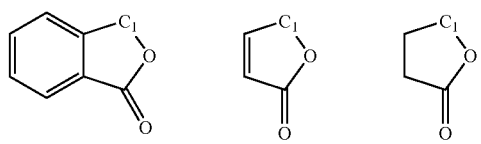

wherein the spiro linkage is formed at $C_1$.

25. The probe of claim 24, wherein said second conjugate is substituted at one or more positions of Formula VI so as to add a signal generating detectable group selected from fluorescein, resorufin and derivatives thereof.

26. The probe of claim 24, wherein said second fluoresent conjugate does not interact substantially with a first peptide tag of the form: $C(X)_iC(X)_jC(X)_kC$, wherein C is Cysteine, X is an amino acid, and i, j, and k are each independently 0 or an integer of from 1 to 8; provided that i, j, and k are all not zero.

27. The probe of claim 24, wherein said second peptide tag is of the form $C(X_i)C$, wherein X is any amino acid, C is Cysteine and i is provided that said second peptide tag includes at least four Cystein 0-6.

28. The probe of claim 27, wherein said second peptide tag is CCGCC (SEQ ID NO:25) or CCCC (SEQ ID NO:24).

29. The probe according to claim 1, wherein said target material is selected from the group consisting of a protein, a peptide, a polypeptide, an antibody, a Lac repressor, and a protein nucleic acid (PNA).

30. The probe of claim 24, wherein said second fluorescent conjugate selectively associates with a tag including a tetra-cysteine-containing sequence.

* * * * *

UNITED STATES PATENT AND TRADEMARK OFFICE
CERTIFICATE OF CORRECTION

| | | |
|---|---|---|
| PATENT NO. | : 7,282,373 B2 | |
| APPLICATION NO. | : 11/257292 | |
| DATED | : October 16, 2007 | |
| INVENTOR(S) | : Ebright et al. | |

It is certified that error appears in the above-identified patent and that said Letters Patent is hereby corrected as shown below:

ON THE TITLE PAGE ITEM 74:

now reads "Hoffman"
        should read --Hoffmann--

IN THE SPECIFICATION:

In Column 7, Line 39,     now reads "Part B of this figure shows the synthesis of $(N_i^{2+}\text{-NTA})_2\text{-Cy3(2a)}$ and $(N_i^{2+}\text{-NTA})_2\text{-Cy5 (2b)}$. Part B of this figure shows the"

should read --Part B of this figure shows the synthesis of $(N_i^{2+}\text{-NTA})_2\text{-Cy3(2a)}$ and $(N_i^{2+}\text{-NTA})_2\text{-Cy5 (2b)}$.--

In Column 8, Line 4,     now reads "doubly-tetracysterine-tagged"
    should read --doubly-tetracysteine-tagged--

In Column 17, Line 2,     now reads "(IA), (IB), (VI), (VI) and (VIII),"
    should read --(IA), (IB), (VI), (VII) and (VIII),--

In Column 23, Line 11,     now reads "quantum yields (O)"
    should read --quantum yields (Q)--

In Column 26, Line 64,     now reads "general structure Formula (II)"
    should read --general structure Formula (IB)--

In Column 27, Line 7,     now reads "molecule of Formula (II)"
    should read --molecule of Formula (IB)--

In Column 28, Line 55,     now reads "SEQ BD NO:36;"
    should read --SEQ ID NO:36;--

UNITED STATES PATENT AND TRADEMARK OFFICE
CERTIFICATE OF CORRECTION

PATENT NO. : 7,282,373 B2
APPLICATION NO. : 11/257292
DATED : October 16, 2007
INVENTOR(S) : Ebright et al.

It is certified that error appears in the above-identified patent and that said Letters Patent is hereby corrected as shown below:

IN THE SPECIFICATION:

In Column 42, Line 33,     now reads "bis –propionamido-phenylsrsine"
should read --bis – propionamido-phenylarsine--

In Column 52, Line 21,     now reads "bis acid ($r_f 0.8$)."
should read --bis acid ($r_f=0.8$).--

In Column 54, Line 46,     now reads "Purity 99%."
should read --Purity $\geq$ 99%.--

In Column 56, Line 27,     now reads "($F^{520/480}/F^{520/480}_o$)"
should read --($F^{520,480}/F^{520/480}_o$)--

In Column 56, Line 65,     now reads "*Mol. Biol.* 312:453468"
should read --*Mol. Biol.* 312:453-468--

In Column 57, Line 25,     now reads "for titration" ($N^{2+}$-NTA)$_2$"
should read --($Ni^{2+}$-NTA)$_2$--

In Column 63, Line 19,     now reads "a derivatives were"
should read --α derivatives were--

In Column 64, Line 8,     now reads "a derivatives was"
should read --α derivatives was--

In Column 64, Line 20,     now reads "a derivatives was"
should read --α derivatives was--

In Column 64, Line 23,     now reads "a derivatives was"
should read --α derivatives was--

UNITED STATES PATENT AND TRADEMARK OFFICE
CERTIFICATE OF CORRECTION

PATENT NO. : 7,282,373 B2
APPLICATION NO. : 11/257292
DATED : October 16, 2007
INVENTOR(S) : Ebright et al.

It is certified that error appears in the above-identified patent and that said Letters Patent is hereby corrected as shown below:

IN THE CLAIMS:

In Column 88, Line 67,      now reads "first fluoroabrome"
should read --first fluorochrome--

In Column 89, Line 46,      now reads "(fluoro, obloro, bromo, or fluoro)"
should read --(fluoro, chloro, bromo, or fluoro)--

In Column 89, Line 64,      now reads "texta-cysteine-containing"
should read --tetra cysteine-containing--

In Column 90, Line 5,      now reads "fluorobrome-binding"
should read --fluorochrome-binding)--

In Column 90, Line 8,      now reads "fluorobromes"
should read --fluorochromes--

In Column 90, Line 13,      now reads "axe sepanted by"
should read --are separated by--

In Column 90, Line 29,      now reads "AEAAAKEAAAKEAAAKEAAAKA"
should read --AEAAAKEAAAKEAAAKEAAAKA--

In Column 90, Line 49,      now reads "Cy5 bis-sulfonato bis-propionamido-phenyl arsine-ethanedibiol"
should read --Cy5 bis-sulfonato bis-propionamido-phenylarsine-ethanedithiol--

In Column 90, Line 50,      now reads "(1,3,2-dibioarsolan-2-yl)"
should read --(1,3,2-dithioarsolan-2-yl)--

In Column 90, Line 52,      now reads "Cy5 bis-sulfonato bis-propionamido-phenyl arsine-ethanedibiol"
should read --Cy5 bis-sulfonato bis-propionamido-phenylarsine-ethanedithiol--

UNITED STATES PATENT AND TRADEMARK OFFICE
CERTIFICATE OF CORRECTION

PATENT NO.         : 7,282,373 B2
APPLICATION NO.    : 11/257292
DATED              : October 16, 2007
INVENTOR(S)        : Ebright et al.

It is certified that error appears in the above-identified patent and that said Letters Patent is hereby corrected as shown below:

IN THE CLAIMS:

In Column 90, Line 59,   now reads "(c) Cy3 bis-sulfonato bis-propionamido-phenylarsine-ethanedibiol or Cy3 bis-prapionamido-phenylarsine-ethanedithiol /FlAsH-EDT (4', 5'-bis(1,3,2-ditbioarsolan-2-yl) fluorescein-(1,2-etheneditbiol)$_2$; and"

should read --(c) Cy3 bis-sulfonato bis-propionamido-phenylarsine-ethanedibiol or Cy3 bis-prapionamido-phenylarsine-ethanedithiol /FlAsH-EDT (4', 5'-bis(1,3,2-dithioarsolan-2-yl) fluorescein-(1,2-etheneditbiol)$_2$; and--

In Column 90, Line 60,   now reads "1,2-etheneditbiol"
should read --1,2-ethanedithiol--

In Column 91, Line 36,   now read "CCPPPCC (SEQ ID NO:20)"
should read --CCPPPPCC (SEQ ID NO:20)--

In Column 94, Line 67,   now reads "SBQ ID NO: 21"
should read --SEQ ID NO: 21--

In Column 95, Line 6,    now reads "bis-sulfonato bis-propionamido-phenylarsifle"
should read --bis-sulfonato bis-propionamido-phenylarsine--

In Column 95, Line 36,   now reads "w is 1,2-ethanedlyl, 1,2-propanedlyl, 2,3-butanediyt 1,3-propanediyl, 1,2-beuzenedlyl, 4-methly-1,2-benzenediyl, 1,2-cyclopentanediyl, 1,2-cyclohexaediyl, 3-hydroxy-1,2-propenediyl, 3-sulfo-1,2-propanediyl, or 1,2, is (carboxy)-1,2-ethanediyl;"

should read --w is 1,2-ethanediyl, 1,2-propanediyl, 2,3-butanediyl, 1,3-propanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl;--

UNITED STATES PATENT AND TRADEMARK OFFICE
CERTIFICATE OF CORRECTION

PATENT NO. : 7,282,373 B2
APPLICATION NO. : 11/257292
DATED : October 16, 2007
INVENTOR(S) : Ebright et al.

It is certified that error appears in the above-identified patent and that said Letters Patent is hereby corrected as shown below:

IN THE CLAIMS:

In Column 95, Line 37,     now reads "1,2-beuzenedlyl"
should read --1,2-benzenediyl--

In Column 95, Line 38,     now reads "1,2-cyclohexaaediyl"
should read --1,2-cyclohexanediyl--

In Column 95, Line 39,     now reads "1,2 is (carboxy)"
should read --1,2-bis (carboxy)--

In Column 95, Lines 40,     now reads "$Y^1$ and $Y_2$, independently, arc H or $CH_3$;"
should read --$Y^1$ and $Y_2$, independently, are H or $CH_3$;--

In Column 95, Line 41,     now reads "$Y^1$ and $^9$,"
should read --$Y^1$ and $Y^2$,--

Signed and Sealed this

Sixth Day of January, 2009

JON W. DUDAS
*Director of the United States Patent and Trademark Office*

```
                          SEQUENCE LISTING

<160> NUMBER OF SEQ ID NOS: 46

<210> SEQ ID NO 1
<211> LENGTH: 6
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (3)..(3)
<223> OTHER INFORMATION: Any amino acid at all Xaa locations
<220> FEATURE:
<221> NAME/KEY: MISC_FEATURE
<222> LOCATION: (4)..(4)
<223> OTHER INFORMATION: Any amino acid at all Xaa locations

<400> SEQUENCE: 1

Cys Cys Xaa Xaa Cys Cys
1               5

<210> SEQ ID NO 2
<211> LENGTH: 6
<212> TYPE: PRT
<213> ORGANISM: Artificial sequence
<220> FEATURE:
<223> OTHER INFORMATION: Target sequence

<400> SEQUENCE: 2

Cys Cys Gly Pro Cys Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Target sequence.

<400> SEQUENCE: 3

Cys Cys Pro Gly Cys Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Target sequence.

<400> SEQUENCE: 4

Cys Gly Pro Cys Cys Gly Pro Cys
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Target sequence.

<400> SEQUENCE: 5

Cys Gly Pro Cys Gly Cys Gly Pro Cys
1               5

<210> SEQ ID NO 6
<211> LENGTH: 10
<212> TYPE: PRT
<213> ORGANISM: Artificial Sequence
<220> FEATURE:
<223> OTHER INFORMATION: Target sequence.

<400> SEQUENCE: 6

Cys Gly Pro Cys Gly Gly Cys Gly Pro Cys
1               5                   10

<210> SEQ ID NO 7
<211> LENGTH: 5
<212> TYPE: PRT
<213> ORGANISM: Artificial sequence
<220> FEATURE:
<223> OTHER INFORMATION: spacer repeat

<400> SEQUENCE: 7

Glu Ala Ala Ala Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Target sequence.

<400> SEQUENCE: 8

His His His His His His
1               5

<210> SEQ ID NO 9
<211> LENGTH: 3
<212> TYPE: PRT
<213> ORGANISM: Artificial sequence
<220> FEATURE:
<223> OTHER INFORMATION: Target sequence.

<400> SEQUENCE: 9

His His His
1

<210> SEQ ID NO 10
<211> LENGTH: 4
<212> TYPE: PRT
<213> ORGANISM: Artificial sequence
<220> FEATURE:
<223> OTHER INFORMATION: Target sequence.

<400> SEQUENCE: 10

His His His His
1

<210> SEQ ID NO 11
```

```
<211> LENGTH: 5
<212> TYPE: PRT
<213> ORGANISM: Artificial sequence
<220> FEATURE:
<223> OTHER INFORMATION: Target sequence.

<400> SEQUENCE: 11

His His His His His
1               5

<210> SEQ ID NO 12
<211> LENGTH: 7
<212> TYPE: PRT
<213> ORGANISM: Artificial sequence
<220> FEATURE:
<223> OTHER INFORMATION: Target sequence.

<400> SEQUENCE: 12

His His His His His His His
1               5

<210> SEQ ID NO 13
<211> LENGTH: 8
<212> TYPE: PRT
<213> ORGANISM: Artificial sequence
<220> FEATURE:
<223> OTHER INFORMATION: Target sequence.

<400> SEQUENCE: 13

His His His His His His His His
1               5

<210> SEQ ID NO 14
<211> LENGTH: 9
<212> TYPE: PRT
<213> ORGANISM: Artificial sequence
<220> FEATURE:
<223> OTHER INFORMATION: Target sequence.

<400> SEQUENCE: 14

His His His His His His His His His
1               5

<210> SEQ ID NO 15
<211> LENGTH: 10
<212> TYPE: PRT
<213> ORGANISM: Artificial sequence
<220> FEATURE:
<223> OTHER INFORMATION: Target sequence.

<400> SEQUENCE: 15

His His His His His His His His His His
1               5                   10

<210> SEQ ID NO 16
<211> LENGTH: 7
<212> TYPE: PRT
<213> ORGANISM: Artificial sequence
<220> FEATURE:
<223> OTHER INFORMATION: target sequence
<220> FEATURE:
<221> NAME/KEY: MISC_FEATURE
<222> LOCATION: (3)..(5)
<223> OTHER INFORMATION: Xaa can be any amino acid

<400> SEQUENCE: 16

Cys Cys Xaa Xaa Xaa Cys Cys
1               5
```

-continued

```
<210> SEQ ID NO 17
<211> LENGTH: 7
<212> TYPE: PRT
<213> ORGANISM: Artificial sequence
<220> FEATURE:
<223> OTHER INFORMATION: Target sequence

<400> SEQUENCE: 17

Cys Cys Gly Pro Cys Cys Cys
1               5

<210> SEQ ID NO 18
<211> LENGTH: 7
<212> TYPE: PRT
<213> ORGANISM: Artificial sequence
<220> FEATURE:
<223> OTHER INFORMATION: Target sequence

<400> SEQUENCE: 18

Cys Cys Pro Gly Pro Cys Cys
1               5

<210> SEQ ID NO 19
<211> LENGTH: 7
<212> TYPE: PRT
<213> ORGANISM: Artificial sequence
<220> FEATURE:
<223> OTHER INFORMATION: Target sequence

<400> SEQUENCE: 19

Cys Cys Pro Pro Pro Cys Cys
1               5

<210> SEQ ID NO 20
<211> LENGTH: 8
<212> TYPE: PRT
<213> ORGANISM: Artificial sequence
<220> FEATURE:
<223> OTHER INFORMATION: Target sequence

<400> SEQUENCE: 20

Cys Cys Pro Pro Pro Pro Cys Cys
1               5

<210> SEQ ID NO 21
<211> LENGTH: 9
<212> TYPE: PRT
<213> ORGANISM: Artificial sequence
<220> FEATURE:
<223> OTHER INFORMATION: Target sequence

<400> SEQUENCE: 21

Cys Cys Pro Pro Pro Pro Pro Cys Cys
1               5

<210> SEQ ID NO 22
<211> LENGTH: 10
<212> TYPE: PRT
<213> ORGANISM: Artificial sequence
<220> FEATURE:
<223> OTHER INFORMATION: Target sequence

<400> SEQUENCE: 22

Cys Cys Pro Pro Pro Pro Pro Pro Cys Cys
1               5                   10
```

```
<210> SEQ ID NO 23
<211> LENGTH: 7
<212> TYPE: PRT
<213> ORGANISM: Artificial sequence
<220> FEATURE:
<223> OTHER INFORMATION: Target sequence

<400> SEQUENCE: 23

Cys Gly Cys Gly Cys Gly Cys
1               5

<210> SEQ ID NO 24
<211> LENGTH: 4
<212> TYPE: PRT
<213> ORGANISM: Artificial sequence
<220> FEATURE:
<223> OTHER INFORMATION: Target sequence

<400> SEQUENCE: 24

Cys Cys Cys Cys
1

<210> SEQ ID NO 25
<211> LENGTH: 5
<212> TYPE: PRT
<213> ORGANISM: Artificial sequence
<220> FEATURE:
<223> OTHER INFORMATION: Target sequence

<400> SEQUENCE: 25

Cys Cys Gly Cys Cys
1               5

<210> SEQ ID NO 26
<211> LENGTH: 6
<212> TYPE: PRT
<213> ORGANISM: Artificial sequence
<220> FEATURE:
<223> OTHER INFORMATION: Target sequence

<400> SEQUENCE: 26

Cys Cys Pro Pro Cys Cys
1               5

<210> SEQ ID NO 27
<211> LENGTH: 9
<212> TYPE: PRT
<213> ORGANISM: Artificial sequence
<220> FEATURE:
<223> OTHER INFORMATION: Spacer

<400> SEQUENCE: 27

Pro Pro Pro Pro Pro Pro Pro Pro Pro
1               5

<210> SEQ ID NO 28
<211> LENGTH: 12
<212> TYPE: PRT
<213> ORGANISM: Artificial sequence
<220> FEATURE:
<223> OTHER INFORMATION: Spacer

<400> SEQUENCE: 28

Pro Pro Pro Pro Pro Pro Pro Pro Pro Pro Pro Pro
1               5                   10
```

<210> SEQ ID NO 29
<211> LENGTH: 22
<212> TYPE: PRT
<213> ORGANISM: Artificial sequence
<220> FEATURE:
<223> OTHER INFORMATION: spacer

<400> SEQUENCE: 29

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 30
<211> LENGTH: 27
<212> TYPE: PRT
<213> ORGANISM: Artificial sequence
<220> FEATURE:
<223> OTHER INFORMATION: Spacer

<400> SEQUENCE: 30

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 31
<211> LENGTH: 19
<212> TYPE: PRT
<213> ORGANISM: Artificial sequence
<220> FEATURE:
<223> OTHER INFORMATION: tag-spacer-tag module

<400> SEQUENCE: 31

Cys Cys Cys Cys Pro Pro Pro Pro Pro Pro Pro Pro Cys Cys Pro
1               5                   10                  15

Pro Cys Cys

<210> SEQ ID NO 32
<211> LENGTH: 21
<212> TYPE: PRT
<213> ORGANISM: Artificial sequence
<220> FEATURE:
<223> OTHER INFORMATION: tag-spacer-tag module

<400> SEQUENCE: 32

Cys Cys Cys Cys Pro Pro Pro Pro Pro Pro Pro Pro Cys Cys Pro
1               5                   10                  15

Pro Pro Pro Cys Cys
            20

<210> SEQ ID NO 33
<211> LENGTH: 21
<212> TYPE: PRT
<213> ORGANISM: Artificial sequence
<220> FEATURE:
<223> OTHER INFORMATION: tag-spacer-tag module

<400> SEQUENCE: 33

Cys Cys Gly Cys Cys Pro Pro Pro Pro Pro Pro Pro Pro Cys Cys
1               5                   10                  15

Pro Pro Pro Cys Cys
            20

<210> SEQ ID NO 34
<211> LENGTH: 22
<212> TYPE: PRT
<213> ORGANISM: Artificial sequence
<220> FEATURE:
<223> OTHER INFORMATION: tag-spacer-tag module

<400> SEQUENCE: 34

Cys Cys Gly Cys Cys Pro Pro Pro Pro Pro Pro Pro Pro Cys Cys
1               5                   10                  15

Pro Pro Pro Pro Cys Cys
            20

<210> SEQ ID NO 35
<211> LENGTH: 22
<212> TYPE: PRT
<213> ORGANISM: Artificial sequence
<220> FEATURE:
<223> OTHER INFORMATION: tag-spacer-tag module

<400> SEQUENCE: 35

Cys Cys Cys Cys Pro Pro Pro Pro Pro Pro Pro Pro Pro Pro Pro
1               5                   10                  15

Cys Cys Pro Pro Cys Cys
            20

<210> SEQ ID NO 36
<211> LENGTH: 24
<212> TYPE: PRT
<213> ORGANISM: Artificial sequence
<220> FEATURE:
<223> OTHER INFORMATION: tag-spacer-tag module

<400> SEQUENCE: 36

Cys Cys Cys Cys Pro Pro Pro Pro Pro Pro Pro Pro Pro Pro Pro
1               5                   10                  15

Cys Cys Pro Pro Pro Pro Cys Cys
            20

<210> SEQ ID NO 37
<211> LENGTH: 24
<212> TYPE: PRT
<213> ORGANISM: Artificial sequence
<220> FEATURE:
<223> OTHER INFORMATION: tag-spacer-tag module

<400> SEQUENCE: 37

Cys Cys Gly Cys Cys Pro Pro Pro Pro Pro Pro Pro Pro Pro Pro
1               5                   10                  15

Pro Cys Cys Pro Pro Pro Cys Cys
            20

<210> SEQ ID NO 38
<211> LENGTH: 25
<212> TYPE: PRT
<213> ORGANISM: Artificial sequence
<220> FEATURE:
<223> OTHER INFORMATION: tag-spacer-tag module

<400> SEQUENCE: 38

Cys Cys Gly Cys Cys Pro Pro Pro Pro Pro Pro Pro Pro Pro Pro
1               5                   10                  15

Pro Cys Cys Pro Pro Pro Pro Cys Cys
            20                  25

```
<210> SEQ ID NO 39
<211> LENGTH: 32
<212> TYPE: PRT
<213> ORGANISM: Artificial sequence
<220> FEATURE:
<223> OTHER INFORMATION: tag-spacer-tag module

<400> SEQUENCE: 39

Cys Cys Cys Cys Ala Glu Ala Ala Ala Lys Glu Ala Ala Ala Lys Glu
1               5                   10                  15

Ala Ala Ala Lys Glu Ala Ala Ala Lys Ala Cys Cys Pro Pro Cys Cys
            20                  25                  30

<210> SEQ ID NO 40
<211> LENGTH: 34
<212> TYPE: PRT
<213> ORGANISM: Artificial sequence
<220> FEATURE:
<223> OTHER INFORMATION: tag-spacer-tag module

<400> SEQUENCE: 40

Cys Cys Cys Cys Ala Glu Ala Ala Ala Lys Glu Ala Ala Ala Lys Glu
1               5                   10                  15

Ala Ala Ala Lys Glu Ala Ala Ala Lys Ala Cys Cys Pro Pro Pro Pro
            20                  25                  30

Cys Cys

<210> SEQ ID NO 41
<211> LENGTH: 34
<212> TYPE: PRT
<213> ORGANISM: Artificial sequence
<220> FEATURE:
<223> OTHER INFORMATION: tag-spacer-tag module

<400> SEQUENCE: 41

Cys Cys Gly Cys Cys Ala Glu Ala Ala Ala Lys Glu Ala Ala Ala Lys
1               5                   10                  15

Glu Ala Ala Ala Lys Glu Ala Ala Ala Lys Ala Cys Cys Pro Pro Pro
            20                  25                  30

Cys Cys

<210> SEQ ID NO 42
<211> LENGTH: 35
<212> TYPE: PRT
<213> ORGANISM: Artificial sequence
<220> FEATURE:
<223> OTHER INFORMATION: tag-spacer-tag module

<400> SEQUENCE: 42

Cys Cys Gly Cys Cys Ala Glu Ala Ala Ala Lys Glu Ala Ala Ala Lys
1               5                   10                  15

Glu Ala Ala Ala Lys Glu Ala Ala Ala Lys Ala Cys Cys Pro Pro Pro
            20                  25                  30

Pro Cys Cys
        35

<210> SEQ ID NO 43
<211> LENGTH: 37
<212> TYPE: PRT
<213> ORGANISM: Artificial sequence
<220> FEATURE:
<223> OTHER INFORMATION: tag-spacer-tag module
```

```
<400> SEQUENCE: 43

Cys Cys Cys Cys Ala Glu Ala Ala Ala Lys Glu Ala Ala Lys Glu
1               5                   10                  15

Ala Ala Ala Lys Glu Ala Ala Lys Glu Ala Ala Lys Ala Cys
            20                  25                  30

Cys Pro Pro Cys Cys
        35

<210> SEQ ID NO 44
<211> LENGTH: 39
<212> TYPE: PRT
<213> ORGANISM: Artificial sequence
<220> FEATURE:
<223> OTHER INFORMATION: tag-spacer-tag module

<400> SEQUENCE: 44

Cys Cys Cys Cys Ala Glu Ala Ala Ala Lys Glu Ala Ala Lys Glu
1               5                   10                  15

Ala Ala Ala Lys Glu Ala Ala Lys Glu Ala Ala Lys Ala Cys
            20                  25                  30

Cys Pro Pro Pro Pro Cys Cys
        35

<210> SEQ ID NO 45
<211> LENGTH: 39
<212> TYPE: PRT
<213> ORGANISM: Artificial sequence
<220> FEATURE:
<223> OTHER INFORMATION: tag-spacer-tag module

<400> SEQUENCE: 45

Cys Cys Gly Cys Cys Ala Glu Ala Ala Ala Lys Glu Ala Ala Lys
1               5                   10                  15

Glu Ala Ala Ala Lys Glu Ala Ala Lys Glu Ala Ala Lys Ala
            20                  25                  30

Cys Cys Pro Pro Pro Cys Cys
        35

<210> SEQ ID NO 46
<211> LENGTH: 40
<212> TYPE: PRT
<213> ORGANISM: Artificial sequence
<220> FEATURE:
<223> OTHER INFORMATION: tag-spacer-tag module

<400> SEQUENCE: 46

Cys Cys Gly Cys Cys Ala Glu Ala Ala Ala Lys Glu Ala Ala Lys
1               5                   10                  15

Glu Ala Ala Ala Lys Glu Ala Ala Lys Glu Ala Ala Lys Ala
            20                  25                  30

Cys Cys Pro Pro Pro Pro Cys Cys
        35                  40
```